(12) United States Patent
Makriyannis et al.

(10) Patent No.: US 12,054,480 B2
(45) Date of Patent: Aug. 6, 2024

(54) COMPOUNDS FOR TREATING CANNABINOID TOXICITY AND ACUTE CANNABINOID OVERDOSE

(71) Applicant: MAKScientific, LLC, Burlington, MA (US)

(72) Inventors: Alexandros Makriyannis, Watertown, MA (US); Kiran Vemuri, Boston, MA (US)

(73) Assignee: MAKScientific, LLC, Burlington, MA (US)

( * ) Notice: Subject to any disclaimer, the term of this patent is extended or adjusted under 35 U.S.C. 154(b) by 0 days.

(21) Appl. No.: 17/392,191

(22) Filed: Aug. 2, 2021

(65) Prior Publication Data
US 2022/0033393 A1 Feb. 3, 2022

Related U.S. Application Data

(60) Provisional application No. 63/059,293, filed on Jul. 31, 2020.

(51) Int. Cl.
| | | |
|---|---|---|
| C07D 417/12 | (2006.01) | |
| A61P 39/02 | (2006.01) | |
| C07D 205/04 | (2006.01) | |
| C07D 207/273 | (2006.01) | |
| C07D 231/14 | (2006.01) | |

(52) U.S. Cl.
CPC ............ *C07D 417/12* (2013.01); *A61P 39/02* (2018.01); *C07D 205/04* (2013.01); *C07D 207/273* (2013.01); *C07D 231/14* (2013.01)

(58) Field of Classification Search
CPC ...... C07D 417/12; C07D 231/14; A61P 39/02
See application file for complete search history.

(56) References Cited

U.S. PATENT DOCUMENTS

| | | |
|---|---|---|
| 4,256,727 A | 3/1981 | Triplett et al. |
| 4,732,900 A | 3/1988 | Weber et al. |
| 5,155,124 A | 10/1992 | Kimata et al. |
| 5,208,231 A | 5/1993 | Kimata et al. |
| 5,462,960 A | 10/1995 | Barth et al. |
| 5,624,941 A | 4/1997 | Barth et al. |
| 5,925,768 A | 7/1999 | Barth et al. |
| 6,028,084 A | 2/2000 | Barth et al. |
| 6,288,061 B1 | 9/2001 | Sueoka et al. |
| 6,344,474 B1 | 2/2002 | Maruani et al. |
| 6,432,984 B1 | 8/2002 | Barth et al. |
| 6,509,367 B1 | 1/2003 | Martin et al. |
| 7,119,108 B1 | 10/2006 | Makriyannis et al. |
| 7,393,842 B2 | 7/2008 | Makriyannis et al. |
| 7,521,471 B2 | 4/2009 | Barth et al. |
| 7,572,785 B2 | 8/2009 | Finke et al. |
| 7,745,440 B2 | 6/2010 | Makriyannis et al. |
| 7,872,006 B2 | 1/2011 | Moritani et al. |
| 8,084,451 B2 | 12/2011 | Makriyannis et al. |
| 8,410,097 B2 | 4/2013 | Makriyannis et al. |
| 8,853,205 B2 | 10/2014 | Makriyannis et al. |
| 10,053,444 B2 | 8/2018 | Makriyannis et al. |
| 2004/0248956 A1 | 12/2004 | Hagmann et al. |
| 2005/0054679 A1 | 3/2005 | Kruse et al. |
| 2007/0117858 A1 | 5/2007 | Xia et al. |
| 2008/0146614 A1 | 6/2008 | Cheng |

FOREIGN PATENT DOCUMENTS

| | | |
|---|---|---|
| EP | 0656354 B1 | 6/1997 |
| WO | 0069848 A1 | 11/2000 |
| WO | 03027076 A2 | 4/2003 |
| WO | 03040107 A1 | 5/2003 |
| WO | 03063781 A2 | 8/2003 |
| WO | 2004060367 A1 | 7/2004 |
| WO | 2004094407 A1 | 11/2004 |
| WO | 2005000820 A2 | 1/2005 |

(Continued)

OTHER PUBLICATIONS

Bergman, Jack et al., "Some effects of CB1 antagonists with inverse agonist and neutral biochemical properties," Physiol Behav. 93, 666-670 (2008).

Chambers, Adam P. et al., "A neutral CB1 receptor antagonist reduces weight gain in rat," Am J Physiol Regul Integr Comp Physiol. 293, R2185-2193 (2007).

Cluny, Nina L. et al., "The neutral cannabinoid CB receptor antagonist AM4113 regulates body weight through changes in energy intake in the rat," Pharmacol Biochem Behav. 97, 537-543 (2011).

Cluny, NL et al., "A novel peripherally restricted cannabinoid receptor antagonist, AM6545, reduces food intake and body weight, but does not cause malaise, in rodents," Br J Pharmacol. 161, 629-642 (2010).

Crocker, Peter J. et al., "The role of fluorine substitution in the structure-activity relationships (SAR) of classical cannabinoids," Bioorganic & Medicinal Letters 17, 1504-1507 (2007).

(Continued)

*Primary Examiner* — Kamal A Saeed
(74) *Attorney, Agent, or Firm* — Alix, Yale & Ristas, LLP

(57) ABSTRACT

The present invention relates to novel compounds that can act as antidotes for treating "Acute Cannabinoid Overdose" produced by classical cannabinoids such as $\Delta^9$-tetrahydrocannabinol (THC) and several synthetic psychoactive cannabinoids (SPCs). The cannabis constituent THC exerts its psychotropic effects via CB1 receptor activation and SPCs mimic the effects of THC with higher potency and severe neurotoxicity. Compounds disclosed in this invention, their enantiomers, diastereomers, geometric isomers, racemates, tautomers, rotamers, atropisomers, metabolites, N-oxides, salts, solvates, hydrates, isotopic variations and their polymorphic forms can be therapeutically useful in an emergency setting for counteracting the intoxicating effects of acute THC ingestion and SPC overdose. Also, aspects of the invention are concerned with pyrazoles, imidazoles, triazoles, thiazoles, oxazoles, dihydropyrazoles, pyrrolidinones, azetidines, oxyazetidines and azaspiro[3.3]heptanes with unique pharmacokinetic and pharmacodynamic properties for treating "Acute Cannabinoid Overdose".

11 Claims, 3 Drawing Sheets

(56) References Cited

FOREIGN PATENT DOCUMENTS

WO 2010104488 A1 9/2010

OTHER PUBLICATIONS

Fan, Hong et al., "Analogs of JHU75528, a PET ligand for imaging of cerebral cannabinoid receptors (CB1): Development of ligands with optimized lipophilicity and binding affinity," European J of Med Chem 44, 593-608 (2009).

Hodge, Janel et al., "The cannabinoid CB1 receptor inverse agonist AM 251 and antagonist AM 4113 produce similar effects on the behavioral satiety sequence in rats," Behav Brain Res. 193, 298-305 (2008).

Holla, B. Shivarama et al., "Studies in biheterocycles. Part VI. A novel transformation during acid-catalyzed indolization of ethyl alpha-(arylhydrazono)furan-2-propionates," Indian J Chem 21B(7), 638-641, CAPLUS, doc. No. 97:216073 (1982).

Howlett, Allyn C. et al., "Azido- and Isothiocyanato-Substituted Aryl Pyrazoles Bind Covalently to the CB1 Cannabinoid Receptor and Impair Signal Transduction," J Neurochem, vol. 74, No. 5, 2176-2180 (2000).

Jarbe, Torbjorn U. C. et al., "Central mediation and differential blockade by cannabinergics of the discriminative stimulus effects of the cannabinoid CB(1) receptor antagonist rimonabant in rats," Psychopharmacology, Mar. 3, 2011.

Jarbe, T.U.C. et al., "Intrinsic effects of AM4113, a putative neutral CB1 receptor selective antagonist, on open-field behaviors in rats," Pharmacol Biochem Behav. 91, 84-90 (2008).

Kubinyi, H. "3D QSAR in Drug Design. Theory Methods and Applications. Ligand-Protein Interactions and Molecular Similarity," vol. 2-3, Springer, p. 243-244, (1998).

Lange, Jos H. M. et al., "Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists," J Med Chem 48, 1823-1838 (2005).

Lange, Jo H. M. et al., "Synthesis, SAR and intramolecular hydrogen bonding pattern of 1,3,5-trisubstituted 4,5-dihydropyrazoles as potent cannabinoid CB1 receptor antagonists," Bioorganic and Medicinal Chemistry Letters 20, p. 1752-1757 (2010).

Limebeer, CL et al., "Inverse agonism of cannabinoid CB1 receptors potentiates LiCl-induced nausea in the conditioned gaping model in rats," Br J Pharmacol. 161, 336-349 (2010).

Patani George A. et al., "Bioisosterism: A Rational Approach in Drug Design," Chem. Rev. 96, 3147-3176 (1996).

Ranatunge Ramani R. et al., "Synthesis and Selective Cyclooxygenase-2 Inhibitory Activity of a Series of Novel, Nitric Oxide Donor-Containing Pyrazoles," J. Med. Chem. 47, 2180-2193 (2004).

Randall, P. A. et al., "The novel cannabinoid CB1 antagonist AM6545 suppresses food intake and food-reinforced behavior," Pharmacol Biochem Behav. 97, 179-184 (2010).

Sink, K.S. et al., "Oral bioavailability of the novel cannabinoid CB1 antagonist AM6527: effects on food-reinforced behavior and comparisons with AM4113," Pharmacol Biochem Behav. 91, 303-306 (2009).

Sink, K.S. et al. "The CB1 inverse agonist AM251, but not the CB1 antagonist AM4113, enhances retention of contextual fear conditioning in rats," Pharmacol Biochem Behav. 95, 479-484 (2010).

Sink, K.S. et al., "Potential anxiogenic effects of cannabinoid CB1 receptor antagonists/inverse agonists in rats: comparisons between AM4113, AM251, and the benzodiazepine inverse agonist FG-7142," European Neuropsychopharmacol. 20, 112-122 (2010).

Sink, Kelly S. et al., "The novel cannabinoid CB1 receptor neutral antagonist AM4113 suppresses food intake and food-reinforced behavior but does not induce signs of nausea in rats," Neuropsychopharmacology. 33, 946-955 (2008).

Storr, M. A. et al., "Differential effects of CB(1) neutral antagonists and inverse agonists on gastrointestinal motility in mice," Neurogastroenterol Motil. 22, 787-796, e223 (2010).

Tam, Joseph et al., "Peripheral CB1 cannabinoid receptor blockade improves cardiometabolic risk in mouse models of obesity," J Clin Invest. 120, 2953-2966 (2010).

Terfloth, Lothar et al., "Electronic Screening: Lead Finding from Database Mining," in The Practice of Medicinal Chemistry, Ch. 9, Wermuth, 2nd Ed. (2003).

Polinsky, Alex "High-Speed Chemistry Libraries: Assessment of Drug-Likeness," in The Practice of Medicinal Chemistry, Ch. 10, Wermuth, 2nd Ed. (2003).

COMPOUNDS FOR TREATING CANNABINOID TOXICITY AND ACUTE CANNABINOID OVERDOSE

STATEMENT REGARDING FEDERALLY SPONSORED RESEARCH

Certain aspects of this invention disclosure have been funded by National Institute on Drugs of Abuse grants R21/R33 $DA_{045882}$ and R41 $DA_{044048}$.

BACKGROUND

The present technology generally relates to pharmacological tools or biologically active novel cannabinergic compounds of the Formula I-XI. In a specific embodiment, the invention disclosed relates to compounds that can be rapidly metabolized in vivo upon producing the required physiological effects. The invention refers to new compounds of the Formula I-XI, their enantiomers, diastereomers, geometric isomers, racemates, tautomers, rotamers, atropisomers, metabolites, N-oxides, salts, solvates, hydrates, isotopic variations, polymorphic forms (crystalline or amorphous) or pro-drugs. In particular, the present technology is also related to novel cannabinergic compounds of the Formula I-XI that possess specific functional groups such as carboxylic ester and oximes that can be metabolized rapidly in vivo into inactive metabolites, while exerting beneficial effects. The compounds of the present invention notably have highly improved safety profiles compared to known CB1 antagonists/inverse agonists such as rimonabant, surinabant, drinabant, ibipinabant, otenabant, rosonabant and taranabant and will be particularly be more effective in reversing the toxicity associated in a patient who has overdosed on synthetic CB1 agonists such as JWH-018, $AM_{2201}$, UR-144, XLR-11, 5F-AKB-48, APICA, STS-135, AB-PINACA, AB-FUBINACA, MDMB-FUBINACA and their next generation analogs.

Marijuana is the one of the most commonly used illicit drugs in the United States. The most common form of marijuana use in humans is inhalation of the smoke of marijuana cigarettes, followed by oral ingestion. Compared to THC and other classical cannabinoids, the synthetic psychoactive cannabinoids (SPCs) such as the aminoalkylindoles represented by JWH-018 and $AM_{2201}$, thus far, have been the more prevalent psychoactive compounds among the abused synthetic cannabinoids that are illegally available for consumption. In contrast to the classical cannabinoids, these and the next generation analogs such as UR-144, XLR-11, 5F-AKB-48, APICA, STS-135, AB-PINACA and AB-FUBINACA have all been relatively easy to synthesize. SPCs have been available through the internet and from "head-shops" and convenience stores at relatively low cost. As of 2020, more than 50 synthetic cannabinoids have been controlled either through legislation or regulatory action and have been confiscated by foreign agencies. As identified by the DEA, frequent, simple, and subtle chemical modifications have led to over 100 additional synthetic cannabinoids that are not controlled, are ever evolving, and are currently appearing in the domestic marketplace, or promulgate over the internet. For users, the exact composition of such products is typically unknown. Many of these cannabimimetics are manufactured in unregulated non-GMP environments, imported into the country as chemical intermediates with no specific pharmaceutical use, and are packaged as consumables along with fillers (e.g., dried, plant material), perhaps with the disclaimer "Not for Human Consumption".

Though all the neuropharmacological mechanisms by which cannabinoids produce their psychoactive effects have not been identified, CB1 activation is still believed to be the main pathway through which THC produces these effects. While THC acts as a CB1 partial agonist, in contrast, SPCs act as full CB1R agonists in cellular assays and in certain animal studies. SPC metabolites retain affinity for and exhibit a range of intrinsic activities at CB1 receptors and CB2 receptors.

Although THC has an onset of 30-60 minutes with peak effects occurring at 2-4 hours, its precise pharmacokinetics in humans depends on the composition of the *cannabis* products, the manner in which the natural drug is smoked or ingested, dose, experience of user and the body-mass index. Evidence from animal studies and human case reports have indicated that the ratio of lethal dose to effective dose of THC is quite large. Although the drug has a high margin of safety, side effects have been reported after acute ingestion leading to various neurological effects.

SPCs detected in humans generally display a peak onset within 5 minutes with half-lives as short as 1.5-2 hours. However, their deleterious effects are much stronger than those of THC which has an apparent plasma elimination half-life of >4 days, in some cases. While long-term use of THC can lead to tolerance and dependence, its short-term use may cause alterations in motor behavior, perception, cognition, memory, learning, endocrine function, food intake and body temperature, with acute consumption leading to hospitalization in some cases. Patients who ingest SPCs on the other hand display symptoms that are more severe and include seizures, hallucinations, psychosis, motions of the extremities, altered mental status, somnolence and cardiac toxicity coupled with tachycardia/bradycardia. Ingestion of SPCs can lead to permanent or long-lasting injury and even death. While patients in the emergency rooms may differ upon presentation, there is no targeted treatment other than standard adjunct therapy for both THC and SPC intoxication. Treatment of acute THC or SPC ingestion in humans is largely supportive and the suggested pharmacological interventions include use of beta-blockers, antiarrhythmic agents, antipsychotics, and GABA-benzodiazepines. Most patients experience withdrawal symptoms that include restlessness, irritability, mild agitation, hyperactivity, insomnia, nausea, cramping, decreased appetite, sweating, and increased dreaming. While CB1 inverse agonists/antagonists (rimonabant and drinabant) are being suggested as alternative treatments, there are currently no pharmaceutical interventions available for directly reversing the toxicity associated in a patient who has overdosed on synthetic CB1 agonists such as JWH018, $AM_{2201}$, UR-144, XLR-11, 5F-AKB-48, APICA, STS-135, AB-PINACA, AB-FUBINACA, MDMB-FUBINACA and their next generation analogs.

SUMMARY OF THE INVENTION

Figure 1:
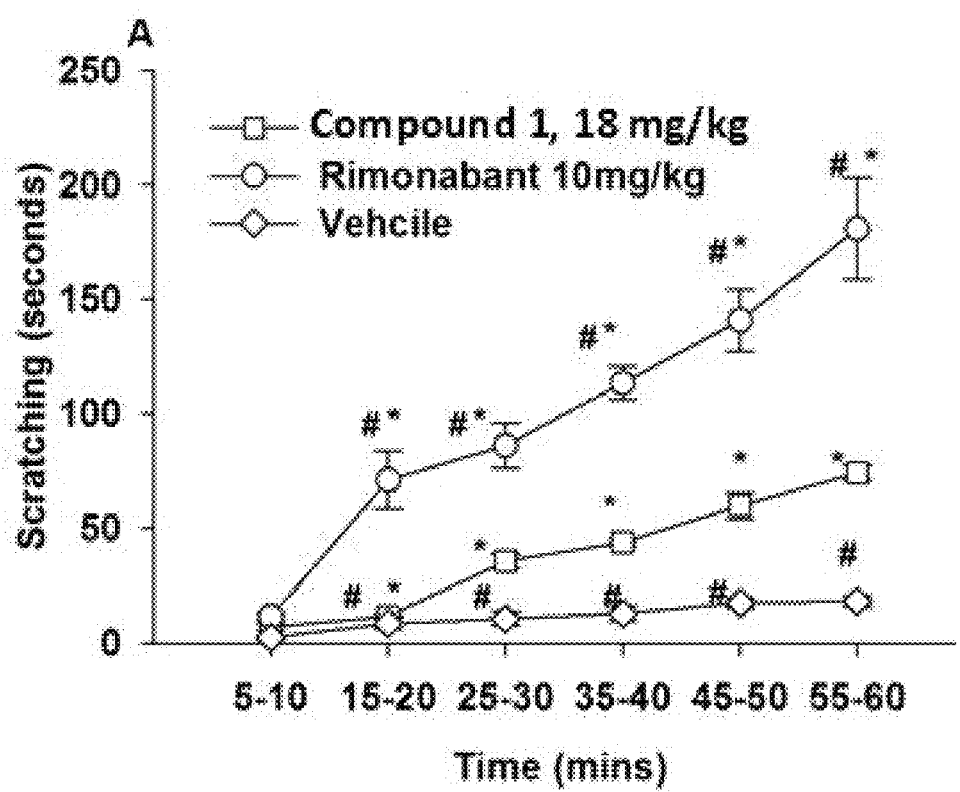
FIG. 1 is a graph showing that Compound 1 produced lesser side effects (scratching episodes) as compared to rimonabant.
Figure 2A:
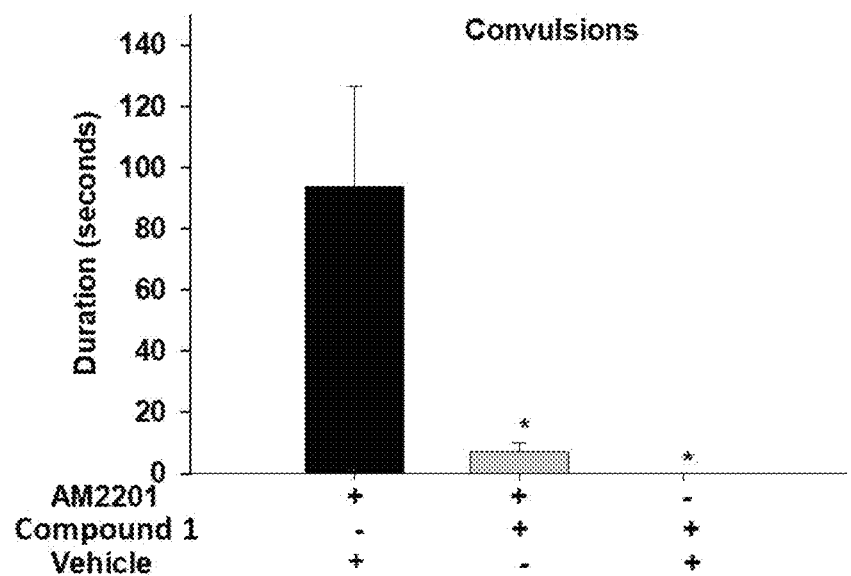
FIGS. 2A-2B are graphs showing that Compound 1 blocks the neurotoxic effects (convulsions and tremors) induced by "suprapharmacological" doses of the CB1 SPC agonist $AM_{2201}$.
Figure 2B:
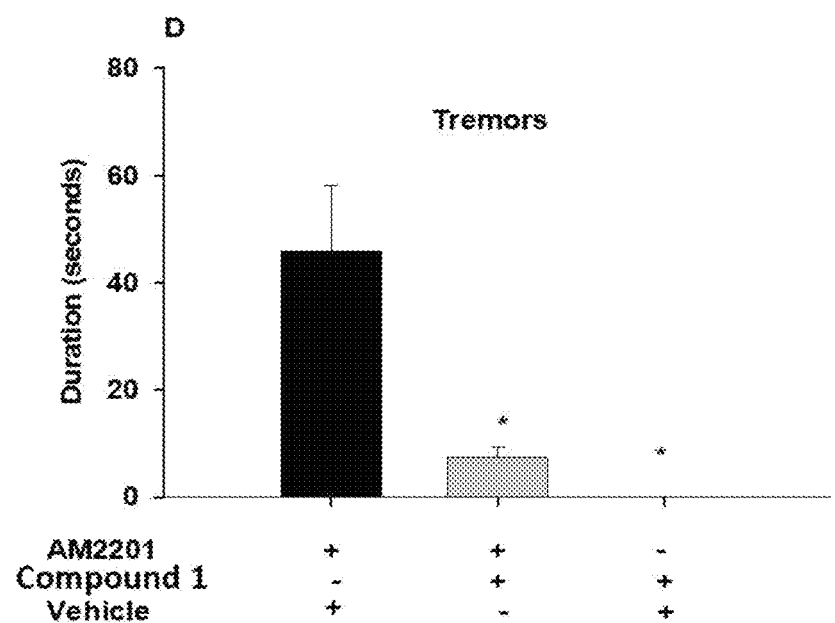
Figure 3A:
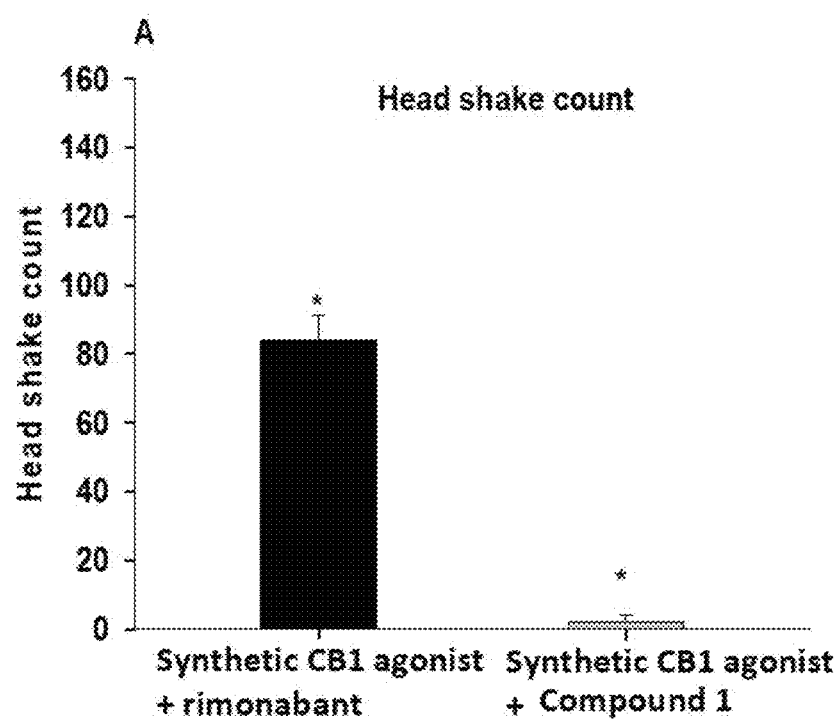
FIG. 3A-B are graphs showing that Compound 1 shows significantly less somatic withdrawal symptoms (head shakes) and paw tremors compared to rimonabant after repeated administration of an CB1 SPC agonist.
Figure 3B:
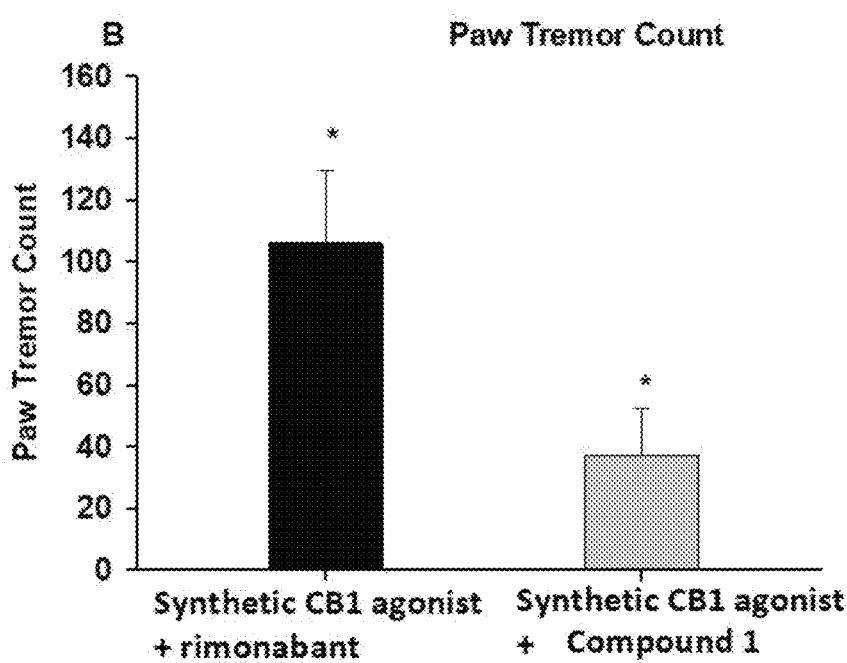

The present technology generally relates to biologically active novel cannabinergic compounds that can behave as short acting CB1 antagonists with controlled deactivation properties and act as medication strategies for treating cannabinoid intoxication that is derived from the ingestion of THC and/or SPCs.

Depending on the clinical goals, agonist-based strategies have been employed to pharmacologically manage drug abuse. For example, the opioid full and partial agonists methadone and buprenorphine, respectively, are used as replacement therapeutics in opioid-addicted individuals. Antagonist-based therapies have been very effective for treating drug abuse and overdose. While naltrexone, a long-acting opioid antagonist is used to reduce relapse liability and help maintain a drug-free state, it can also induce severe withdrawal-like symptoms, especially in opioid-dependent patients and people who overdose. In this regard, the short-acting antagonist naloxone acts as a perfect antidote and a life-saver medication for treating overdose. When administered appropriately, naloxone has been the most effective antidote to date at reversing the symptoms of opioid overdose without inducing severe withdrawal symptoms.

To date, the treatment for cannabinoid intoxication has been based upon case reports presented in an emergency room, and as described by ER professionals and by doctors. Early clinical trials using low doses of rimonabant, a CB1 inverse agonist, yielded mixed results when measuring physical withdrawal syndrome in cannabis-dependent subjects. However, this data did not preclude the possibility of antagonist-elicited withdrawal at higher doses. Rimonabant and drinabant are known to have a long terminal half-life which allows it to segregate in fatty tissues and cell membranes and diffuse slowly into plasma. In vivo data indicates that such compounds display long half-lives and because of this, it is highly possible that a withdrawal reaction can be precipitated by CB1 antagonists/inverse agonists such as rimonabant and drinabant wherein the severity symptoms can vary with the dose, the routes of administration and the degree and type of cannabis intoxication, if ever approved and used.

The concept of a short acting CB1 antagonist as an antidote for cannabinoid intoxication is analogous to using naloxone as a lifesaver on the street vs. naltrexone. As in the case of opioid overdose, treatment of a patient intoxicated on cannabinoids in the ER should include recognition of other substance use disorders, including comorbid psychiatric disorders. All these considerations indicate the value of short-acting CB1 antagonist-based strategies for treating acute cannabinoid intoxication. As in the case of short-acting naloxone, the problem of antagonist-elicited withdrawal can be successfully addressed in individuals admitted into ER and raises the realistic possibility that similar strategies could be employed by using short acting CB1 antagonists to manage acute THC (herbal or synthetic) and SPC intoxication.

A very successful method for controlling the time-course of a drug is through the soft drug approach wherein a labile moiety (e.g. carboxyester group, oxime functionality) is incorporated into the drug molecule for achieving a facile and rapid one-step inactivation via enzymatic action (ex. carboxylesterase, aryl esterase, cholinesterase, paraoxonase or albumin).

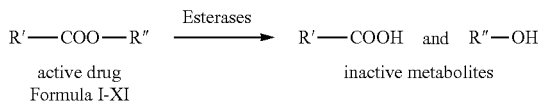

R'—COO—R" (active drug Formula I-XI) →[Esterases]→ R'—COOH and R"—OH (inactive metabolites)

This labile moiety can be targeted by ubiquitous and fairly nonselective enzymes expressed throughout body organs and in blood. The nature and the position of the functional group primarily define the time course of drug action and half-lives. By definition, soft drugs are isosteric variations of their longer acting prototypes that can accommodate all of the key pharmacophoric features required for biological activity. This is coupled with suitable structural modifications to allow for the enzymatic transformation of the biologically active soft drug to inactive or nearly inactive product(s). The concept has been applied towards well-known drugs such as remifentanil (Ultiva™), etomidate (Amidate™), and esmolol (Brevibloc™). By incorporating features that can be modulated by endogenous enzyme action, these novel compounds of the present invention are expected to display considerably much shorter half-lives while displaying equal or greater potency for the CB1 receptor than their parent non-hydrolysable analogs.

Briefly stated, an embodiment of the invention is concerned with new and improved esters and oximes that can be metabolized in vivo and act on the cannabinoid receptors. The inventive ligands of this embodiment can be represented by general formula I and their enantiomers, diastereomers, geometric isomers, racemates, tautomers, rotamers, atropisomers, isotopic variations, salts, N-oxides, hydrates and polymorphic forms (crystalline or amorphous):

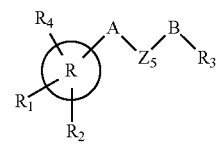

I wherein:
R is a heteroaromatic, heterocyclic or heterobicyclic ring;
A, Z5, B if present, each independently comprise >C(=O), >N(R$_6$), —C(=Nalkyl), or a direct bond,
R$_6$ is hydrogen, —OH, —S(O$_2$)alkyl, alkyl or substituted alkyl;
In a variation of formula I, R1 and R2 each independently comprise —(CH$_2$)$_n$-Z.
n is an integer from 0 to about 7.
Z comprises H, halogen, ester, CF$_3$, CF$_2$H, N$_3$, NCS, CN, NO$_2$, NX$_1$X$_2$, OX$_3$, SX$_3$, OAc, OSO$_2$X$_3$, —C(=O)N—O-X$_1$, —C(=N—O-X$_1$)X$_2$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$NX$_1$X$_2$, alkyl-CN, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, NO, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or $-CX_9=CHX_{10}$ wherein $X_9$ and $X_{10}$ each independently comprise H or alkyl Wherein m is an integer from 0 to 7 j is an integer from 0 to about 6, or k is an integer from 0 to about 2

In a variation of formula I, R1 and R2 each independently comprise $-(CH_2)_n$-Z.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom.

In a variation of formula I, R1 and R2 each independently comprise $-(CH_2)_n$-Z.

n is an integer from 0 to about 7.

Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the $-(CH_2)_n-$ group and the Z group can be any available ring carbon atom or any available ring nitrogen atom.

In a variation of formula I, R1 and R2 each independently comprise $-(CH_2)_n$-Z.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom.

In a variation of formula I, R1 and R2 each independently comprise $-(CH_2)_n$-Z.

n is an integer from 0 to about 7.

Z comprises

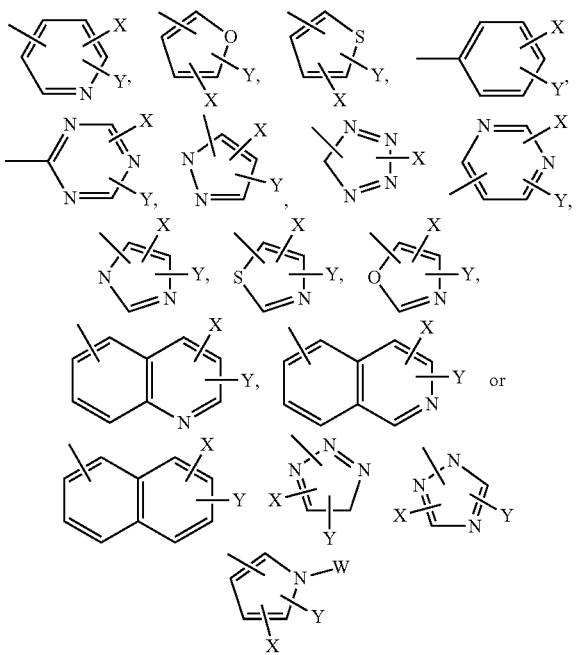

wherein X and Y each independently comprise, H, halogen, ester, $CF_3$, $CF_2H$, $N_3$, NCS, CN, $NO_2$, $NX_1X_2$, $-C(=O)N-O-X_1$, $-C(=N-O-X_1)X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, $-C≡CX_8$;

$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, $(CH_2)_mCN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$ wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or

W comprises H or alkyl k is an integer from 0 to about 2

In a variation of formula I, R1 and R2 each independently —$(CH_2)_n$-Z.

n is an integer from 0 to about 7.

Z comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a Variation of Formula I, R1 and R2 Each Independently Comprise —$(CH_2)_n$-Z;

n comprises an integer from 0 to about 7;

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I, R1 and R2 each independently comprise —$(CH_2)_m$-$Q_1$-$(CH_2)_n$-Z;

$Q_1$ comprises NH, O, S, —CH=CH—, —C≡C—, —CO, $SO_2$ or $OSO_2$;

m is an integer from 1 to about 7;

n is an integer from 0 to about 7;

Z comprises H, halogen, ester, $CF_3$, $CF_2H$, $N_3$, NCS, CN, $NO_2$, $NX_1X_2$, $OX_3$, $SX_3$, OAc, $OSO_2X_3$, —C(=O)N—O-$X_1$, —C(=N—O-$X_1$)$X_2$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_jNX_1X_2$, alkyl-CN, NH-acyl, NH-aroyl, CHO, C(halogen)$_3$, $COOX_8$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members;

$X_3$ comprises H, alkyl, $NO_2$, NO, $(CH_2)_mCN$, hydroxyloweralkyl, or alkyl-$NX_1X_2$;

$X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6, and k is an integer from 0 to about 2.

In a variation of formula I, R1 and R2 each independently comprise-$Q_2$-$(CH_2)_n$-Z;

$Q_2$ is optionally present and if present comprises —$CH_2$—NH, —$CH_2$—O, —$CH_2$—S, —$CH_2$—$SO_2$ or —$CH_2$—$OSO_2$;

n is an integer from 0 to about 7;

Z comprises H, halogen, ester, $CF_3$, $CF_2H$, $N_3$, NCS, CN, $NO_2$, $NX_1X_2$, $OX_3$, $SX_3$, OAc, $OSO_2X_3$, —C(=O)N—O-$X_1$, —C(=N—O-$X_1$)$X_2$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_jNX_1X_2$, alkyl-CN, NH-acyl, NH-aroyl, CHO, C(halogen)$_3$, $COOX_8$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, NO, $(CH_2)_mCN$, hydroxyloweralkyl, or alkyl-$NX_1X_2$;

$X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R1 and R2 each independently comprise —(CH$_2$)$_m$-Q$_1$-(CH$_2$)$_n$-Z;
Q$_1$ comprises NH, O, S, CH=CH, C≡C, CO, SO$_2$ or OSO$_2$;
m is an integer from 1 to about 7;
n is an integer from 0 to about 7; and
Z comprises a bicyclic ring, a heterobicyclic ring, a tricyclic ring, a heterotricyclic ring, a polycyclic ring or a heteropolycyclic ring.

In a variation of formula I, R1 and R2 each independently comprise —(CH$_2$)$_m$-Q$_1$-(CH$_2$)$_n$-Z;
Q$_1$ comprises NH, O, S, CH=CH, C≡C, CO, SO$_2$ or OSO$_2$;
m is an integer from 1 to about 7;
n is an integer from 0 to about 7;
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I, R1 and R2 each independently comprise —(CH$_2$)$_m$-Q$_1$-(CH$_2$)$_n$-Z;
Q$_1$ comprises N, O, S, CH=CH, C≡C, CO, SO$_2$ or OSO$_2$;
m is an integer from 1 to about 7;
n is an integer from 0 to about 7; and
Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom.

In a variation of formula I R1 and R2 each independently comprise —(CH$_2$)$_m$-Q$_1$-(CH$_2$)$_n$-Z;
Q$_1$ comprises NH, O, S, CH=CH, C≡C, CO, SO$_2$ or OSO$_2$;
m is an integer from 1 to about 7;
n is an integer from 0 to about 7; and
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise —(CH$_2$)$_m$-Q$_1$-(CH$_2$)$_n$-Z;
Q$_1$ comprises N, O, S, CH=CH, C≡C, CO, SO$_2$ or OSO$_2$;
m is an integer from 1 to about 7;
n is an integer from 0 to about 7;
Z comprises

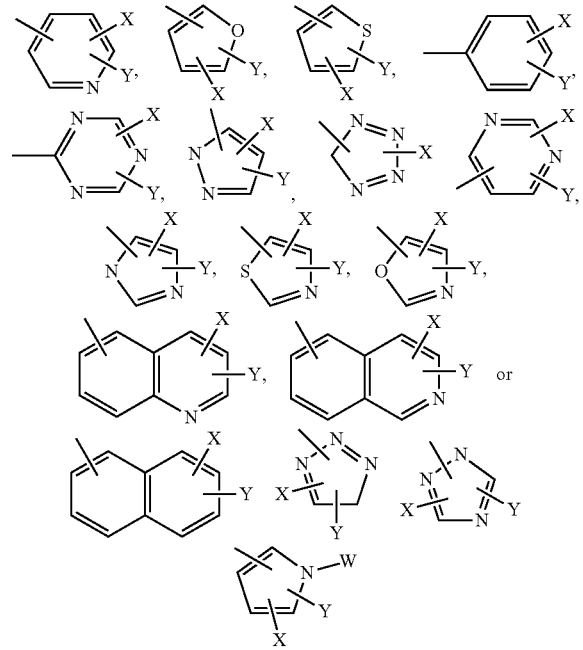

wherein X and Y each independently comprise, H, ester, halogen, CF$_3$, CF$_2$H, N$_3$, NCS, CN, NO$_2$, —C(=O)N—O-X$_1$, —C(=N—O-X$_1$)X$_2$, NX$_1$X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$, X$_1$ and X$_3$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxylower-alkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein $X_9$ and $X_{10}$ each independently comprise H or alkyl;
m is an integer from 0 to 7;
j is an integer from 0 to about 6;
k is an integer from 0 to about 2; and
W comprises H or alkyl In a variation of formula I R1 and R2 each independently comprise. —$(CH_2)_m$-$Q_1$-$(CH_2)_n$-Z;
$Q_1$ comprises NH, O, S, CH=CH, C≡C, CO, $SO_2$ or $OSO_2$;
m is an integer from 1 to about 7;
n is an integer from 0 to about 7; and
Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members.

In a variation of formula I R1 and R2 each independently comprise —$(CH_2)_m$-$Q_1$-$(CH_2)_n$-Z;
$Q_1$ comprises NH, O, S, CH=CH, C≡C, CO, $SO_2$ or $OSO_2$;
m is an integer from 1 to about 7;
n is an integer from 0 to about 7; and
Z comprises

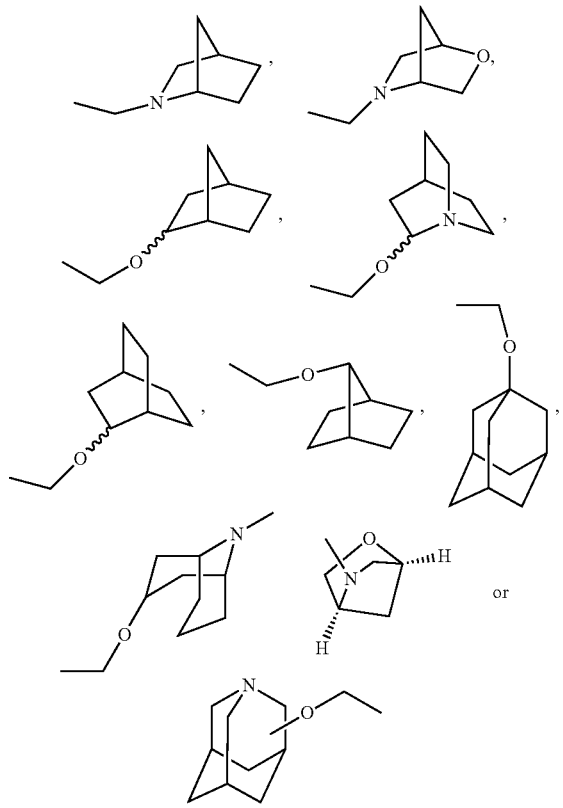

In a variation of formula I R1 and R2 each independently comprise -T-$(CH_2)_n$-Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
Z comprises H, ester, halogen, $CF_3$, $CF_2H$, $N_3$, NCS, CN, $NO_2$, $NX_1X_2$, $OX_3$, $SX_3$, OAc, $OSO_2X_3$, —C(=O)N—O-$X_1$, —C(=N—O-$X_1$)$X_2$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=CH$X_8$, —C≡C$X_8$;
$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S
$X_1$ and $X_2$ together comprise part of a heterocyclic ring having about 4 to about 7 ring members and optionally one additional heteroatom selected from O, N or S, or
$X_1$ and $X_2$ together comprise part of an imide ring having about 5 to about 6 members,
$X_3$ comprises H, alkyl, $NO_2$, NO, $(CH_2)_mCN$, hydroxyloweralkyl, or alkyl-$NX_1X_2$,
$X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein
$X_7$ comprises H, alkyl, $NO_2$, NO, $P(O)(OX_8)_2$, PH(O)$(OX_8)$, $S(O)_kN$(alkyl)$_2$, $S(O)_kX_8$, $S(O)_kOX_8$, $COOX_8$, $CONX_8$, $SO_3H$, $COX_8$, wherein
$X_8$ comprises H, alkyl, carbocyclic ring, heterocyclic ring, aromatic ring, heteroaromatic ring, or —$CX_9$=CH$X_{10}$, wherein
$X_9$ and $X_{10}$ each independently comprise H or alkyl;
m is an integer from 0 to 7;
j is an integer from 0 to about 6; and
k is an integer from 0 to about 2

In a variation of formula I R1 and R2 each independently comprise -T-$(CH_2)_n$-Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_n$-Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring; and
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_n$-Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
Z comprises

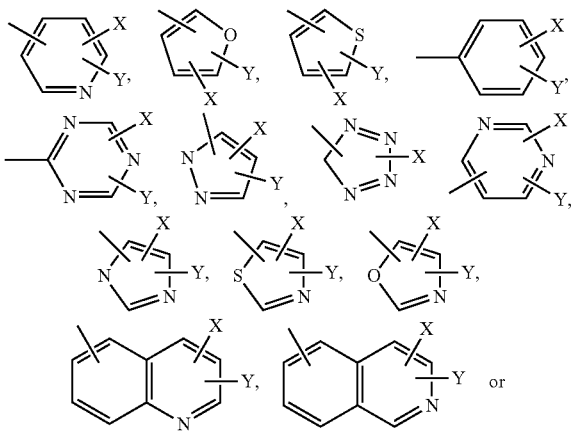

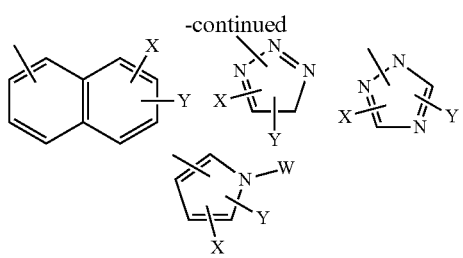

wherein X and Y each independently comprise, H, halogen, ester, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$, X$_1$ and X$_3$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$ wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl;
m is an integer from 0 to 7;
j is an integer from 0 to about 6;
k is an integer from 0 to about 2; and
W comprises H or alkyl.

In a variation of formula I R1 and R2 each independently comprise -T-(CH$_2$)$_n$-Z;
n comprises an integer from 0 to about 7;
T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;
Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I R1 and R2 each independently comprise -T-(CH$_2$)$_m$-Q$_1$-(CH$_2$)$_n$-Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$;

Z comprises H, halogen, ester, CF$_3$, CF$_2$H, N$_3$, NCS, CN, NO$_2$, NX$_1$X$_2$, OX$_3$, SX$_3$, OAc, OSO$_2$X$_3$, —C(=O)N—O-X$_1$, —C(=N—O-X$_1$)X$_2$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$NX$_1$X$_2$, alkyl-CN, NH-acyl, NH-aroyl, CHO, C(halogen)$_3$, COOX$_8$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$, X$_1$ and X$_3$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, NO, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$, wherein X$_9$ and X$_{10}$ each independently comprise H or alkyl;

m is an integer from 0 to 7;

j is an integer from 0 to about 6; and k is an integer from 0 to about 2.

In a variation of formula I R1 and R2 each independently comprise -T-(CH$_2$)$_m$-Q$_1$-(CH$_2$)$_n$-Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$;

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_m$-Q$_1$-(CH$_2$)$_n$-Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$;

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R1 and R2 each independently comprise -T-(CH$_2$)$_m$-Q$_1$-(CH$_2$)$_n$-Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

Q$_1$ comprises NH, O, S, CH=CH, C≡C, CO, SO$_2$ or OSO$_2$;

Z comprises

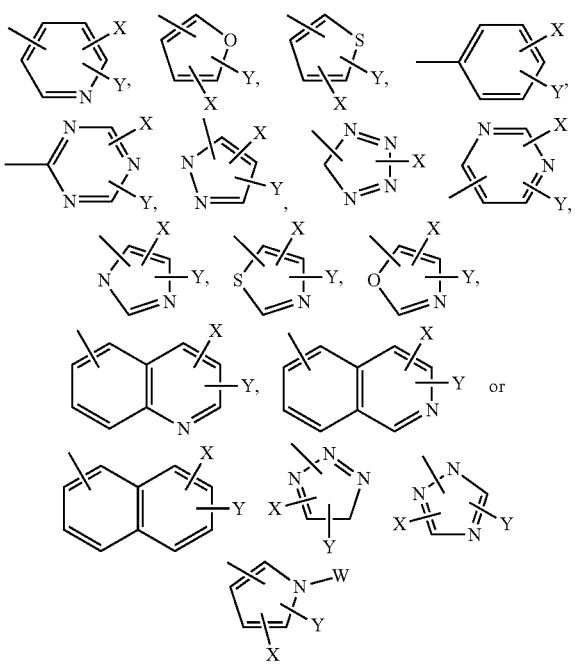

wherein X and Y each independently comprise, H, halogen, ester, $CF_3$, $CF_2H$, $N_3$, NCS, CN, $NO_2$, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$, $X_1$ and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_mCN$, hydroxylower-alkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, or O-alkyl-$X_7$, wherein $X_7$ comprises H, alkyl, $NO_2$, NO, P(O)($OX_8$)$_2$, PH(O)($OX_8$), S(O)$_k$N(alkyl)$_2$, S(O)$_kX_8$, S(O)$_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;
m is an integer from 0 to 7;
j is an integer from 0 to about 6;
k is an integer from 0 to about 2; and
W comprises H or alkyl.

In a variation of formula I R1 and R2 each independently comprise -T-(CH$_2$)$_m$-$Q_1$-(CH$_2$)$_n$-Z;

m and n independently comprises an integer from 0 to about 7;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

$Q_1$ comprises NH, O, S, CH=CH, C≡C, CO, $SO_2$ or $OSO_2$; and Z comprises an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members.

In a variation of formula I, R1 and R2 each independently comprise -T-(CH$_2$)$_m$-$Q_1$-(CH$_2$)$_n$-Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

$Q_1$ comprises NH, O, S, CH=CH, C≡C, CO, $SO_2$ or $OSO_2$;

Z comprises:

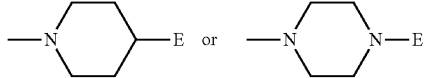

wherein E comprises a C1 to about C4, linear or branched alkyl group, a phenyl group, a substituted phenyl group, a benzyl group or a substituted benzyl group.

In a variation of formula I, R1 and R2 each independently comprise -T-(CH$_2$)$_m$-$Q_1$-(CH$_2$)$_n$-Z;

T comprises a carbocyclic ring having 3 to about 8 ring members, an unsaturated ring having 3 to about 8 carbon atoms as ring members, an aromatic ring having 5 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring;

m and n independently comprises an integer from 0 to about 7;

$Q_1$ comprises NH, O, S, CH=CH, C≡C, CO, $SO_2$ or $OSO_2$;

Z comprises

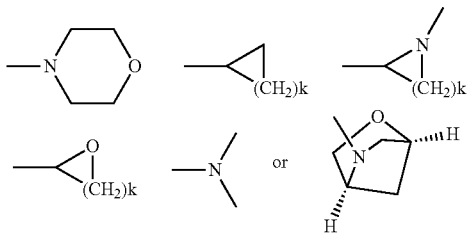

wherein k is an integer from 1 to about 5. $A_1$ and $A_2$ each independently comprise a C1 to about C4 alkyl group, a phenyl group or a substituted phenyl group.

In a variation of formula I, R1 and R2 each independently comprise -T-($CH_2$)$_m$-Q-($CH_2$)$_n$—(C($X_1$)($X_2$))$_p$-Z;

m, n and p are an integer from 0 about 7;

T comprises an aromatic ring having 5 to about 8 carbon atoms as ring members or a heteroaromatic ring having 5 to about 8 ring members;

Q comprises C≡C; and

Z comprises CN, alkyl-CN, OH, $CONX_1X_2$ or $ONO_2$.

In a variation of formula I, R1 is represented by the formula XII

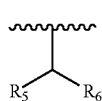

wherein R5 and R6 each independently comprise —($CH_2$)-Z or -T-($CH_2$)-Q-($CH_2$)—Z or -T-($CH_2$)$_n$-Z T an aromatic or a heteroaromatic ring having 5 to about 8 carbon atoms as ring members Q comprises NH, O, S, CH=CH, C≡C, CO, $SO_2$ or $OSO_2$;

m and n are independently an integer from 0 to about 7;

Z comprises H, halogen, ester, $CF_3$, $CF_2H$, $N_3$, NCS, CN, $NO_2$, $NX_1X_2$, $OX_3$, $SX_3$, OAc, $OSO_2X_3$, —C(=O)N—O-$X_1$, —C(=N—O-$X_1$)$X_2$, O-acyl, S-acyl, $SO_2$-alkyl, SO-alkyl, SC($CH_3$)$_2COOX_8$, OC($CH_3$)$_2COOX_8$, C($CH_3$)$_2COOX_8$, Si(alkyl)$_3$, O-aroyl, O($CH_2$)$_jOX_3$, O($CH_2$)$_jNX_1X_2$, alkyl-CN, NH-acyl, NH-aroyl, CHO, C(halogen)$_3$, $COOX_8$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$, $X_2$, and $X_3$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, aryl, $NO_2$, NO, ($CH_2$)$_m$CN, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, or O-alkyl-$X_7$ wherein $X_7$ comprises H, alkyl, $NO_2$, NO, P(O)($OX_8$)$_2$, PH(O)($OX_8$), S(O)$_kN$(alkyl)$_2$, S(O)$_kX_8$, S(O)$_kOX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$ wherein $X_9$ and $X_{10}$ each independently comprise H or alkyl Wherein m is an integer from 0 to 7 j is an integer from 0 to about 6, or k is an integer from 0 to about 2.

In a variation of formula I, R1 is represented by the formula XII

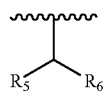

wherein;

R5 and R6 each independently comprise -T-($CH_2$)$_m$-Q-($CH_2$)$_n$-Z or -T-($CH_2$)$_n$-Z and T is an aromatic or a heteroaromatic ring having 5 to about 8 carbon atoms as ring members, m and n are independently an integer from 0 to about 7;

Z is $COOX_8$, —C(=O)N—O-$X_1$ or Z is —C(=N—O-$X_1$) $X_1$ $X_1$ and $X_1$ comprise H or alkyl, Q is CH=CH or C≡C;

m and n are independently an integer from 0 to about 7;

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S and R2 and R4 are each independently H or alkyl with the proviso that when either of R5 or R6 is -T-($CH_2$)$_m$-Q-($CH_2$)$_n$-Z or -T-($CH_2$)$_n$-Z, the other group is an aromatic or a heteroaromatic ring having 5 to about 8 carbon atoms as ring members.

In a variation of formula I, R1 is represented by the formula XII

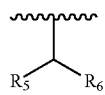

wherein;

R5 and R6 each independently comprise —($CH_2$)$_n$-$Z_6$ or -T-($CH_2$)$_m$-Q-($CH_2$)$_n$-$Z_6$ or -T-($CH_2$)$_n$-$Z_6$ n is independently an integer from 0 to about 7;

$Z_6$ is C4-C7 alkyl, $COOX_8$, —C(=O)N—O-$X_1$ or Z is —C(=N—O-$X_1$) $X_1$ $X_1$ and $X_1$ comprise H or alkyl, Q is CH=CH or C≡C;

m and n are independently an integer from 0 to about 7;

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S and R2 and R4 are each independently H or alkyl with the proviso that, when either of R5 or R6 is —(CH$_2$)$_n$-Z$_6$, the other group is -T-(CH$_2$)$_m$-Q-(CH$_2$)$_n$-Z$_6$ or -T-(CH$_2$)$_n$-Z$_6$ wherein T is an aromatic or a heteroaromatic ring having 5 to about 8 carbon atoms as ring members and m and n are an integer from 4 to about 7.

In a variation of formula I, R3 comprises a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring.

In a variation of formula I, R3 comprises

wherein G comprises CH, C(CH$_3$), C(CN) or N;

L, K and J each independently comprise (CH$_2$)$_n$, (CH$_3$)$_2$, C=O, O, —CHOH, C(CH$_3$)OM$_1$, C(CH$_2$)$_n$(X)Y, NM$_1$, SO$_2$SO or S;

n is an integer from 0 to about 7;

M$_1$ is H, alkyl, C(O)M$_2$, wherein

M$_2$ is H, alkyl, NM$_3$M$_4$, OM$_5$ and M$_3$, M$_4$ and M$_5$ are independently H, OH or alkyl, and X and Y each independently comprise, H, halogen, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_8$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxylower-alkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$=CHX$_{10}$ wherein X$_9$ and X$_{10}$ each independently comprise H or alkyl;

m is an integer from 0 to 7;

j is an integer from 0 to about 6; and k is an integer from 0 to about 2.

In a variation of formula I, R3 comprises

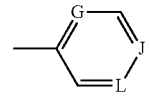

wherein G, L and J each independently comprise CH or N.

In a variation of formula I, R3 comprises

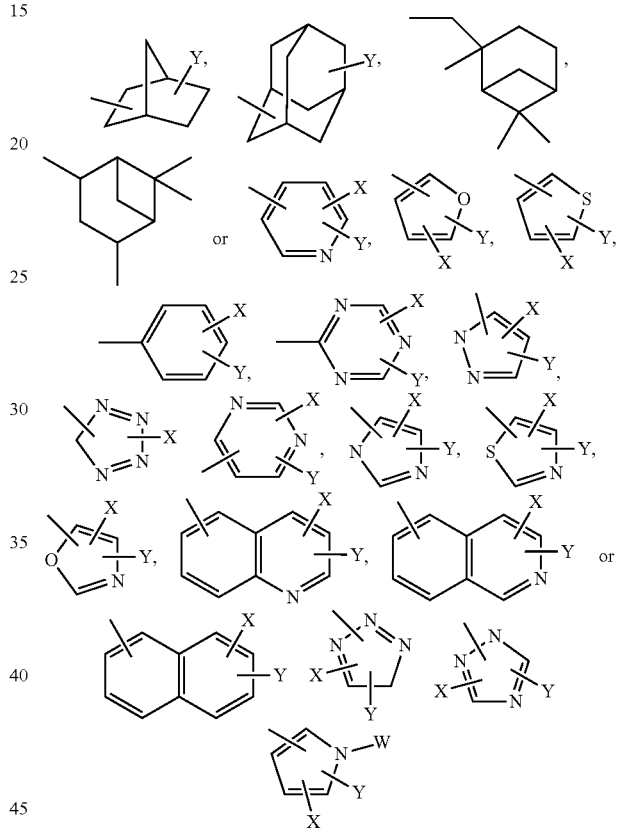

wherein X and Y each independently comprise, H, halogen, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

X$_1$ and X$_2$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, NO$_2$, (CH$_2$)$_m$CN, hydroxylower-alkyl, or alkyl-NX$_1$X$_2$, $X_4$, $X_5$, and $X_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein $X_7$ comprises H, alkyl, NO$_2$, NO, P(O)(OX$_8$)$_2$, PH(O) (OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —CX$_9$=CHX$_{10}$, wherein $X_9$ and $X_{10}$ each independently comprise H or alkyl;

m is an integer from 0 to 7;

j is an integer from 0 to about 6;

k is an integer from 0 to about 2; and

W comprises H or alkyl.

In a variation of formula I, R3 comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In a variation of formula I, R4
comprises H, halogen, CF$_3$, CF$_2$H, N$_3$, NCS, CN, NO$_2$, phenyl, NX$_1$X$_2$,
—C(=O)N—O-X$_1$, —C(=N—O-X$_1$)X$_2$, OX$_3$, SX$_3$, OAc, OSO$_2$X$_3$, O-acyl, S-acyl, 8O2-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

$X_1$ and $X_2$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, NO$_2$, (CH$_2$)$_m$CN, hydroxylower-alkyl, or alkyl-NX$_1$X$_2$, $X_4$, $X_5$, and $X_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein $X_7$ comprises H, alkyl, NO$_2$, NO, P(O)(OX$_8$)$_2$, PH(O) (OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein $X_8$ comprises H, alkyl, carbocyclic ring, heterocyclic ring, aromatic ring, heteroaromatic ring, or —CX$_9$=CHX$_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R4 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring.

In an advantageous variation of formula I, R4 comprises

In a variation of formula I, R4 comprises —(CH$_2$)$_d$-Z;

d is an integer from 1 to about 6;

comprises H, halogen, CF$_3$, CF$_2$H, N$_3$, NCS, CN, NO$_2$, phenyl, NX$_1$X$_2$,
—C(=O)N—O-X$_1$, —C(=N—O-X$_1$)X$_2$, OX$_3$, SX$_3$, OAc, OSO$_2$X$_3$, O-acyl, S-acyl, 8O2-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$, —C≡CX$_8$;

$X_1$ and $X_2$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_m CN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_k N(alkyl)_2$, $S(O)_k X_8$, $S(O)_k OX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R4 comprises —$CH_2OH$ or —$CH_2Oalkyl$.

In a variation of formula I, R4 comprises —$(CH_2)_d$-Z;

d is an integer from 1 to about 6; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_d$— group and the Z group can be any available ring carbon atom or any available ring nitrogen atom.

In a variation of formula I, R4 comprises —$(CH_2)_d$-Z;

d is an integer from 1 to about 6; and

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_d$— group and the Z group can be any available ring carbon atom or any available ring nitrogen atom.

In a variation of formula I, R4 comprises —$(CH_2)_m$-$Q_1$-$(CH_2)_n$-Z;

$Q_1$ comprises NH, O, S, CH=CH, C≡C, CO, $SO_2$ or $OSO_2$;

m is an integer from 1 to about 7;

n is an integer from 0 to about 7;

Z comprises H, halogen, $CF_3$, $CF_2H$, $N_3$, NCS, CN, $NO_2$, phenyl, $NX_1X_2$, —$C(=N-O-X_1)X_1$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, —C≡$CX_8$;

$X_1$ and $X_2$ each independently comprise H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members, $X_3$ comprises H, alkyl, $NO_2$, $(CH_2)_m CN$, hydroxyloweralkyl, or alkyl-$NX_1X_2$, $X_4$, $X_5$, and $X_6$ each independently comprise H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, or O-alkyl-$X_7$, wherein $X_7$ comprises H, alkyl, $NO_2$, NO, $P(O)(OX_8)_2$, $PH(O)(OX_8)$, $S(O)_k N(alkyl)_2$, $S(O)_k X_8$, $S(O)_k OX_8$, $COOX_8$, $CONX_8$, $SO_3H$, $COX_8$, wherein $X_8$ comprises H, alkyl, carbocyclic ring, heterocyclic ring, aromatic ring, heteroaromatic ring, or —$CX_9$=$CHX_{10}$, wherein $X_9$ and $X_{10}$ each independently comprise H or alkyl;

m is an integer from 0 to 7;

j is an integer from 0 to about 6; and k is an integer from 0 to about 2.

In a variation of formula I, R4 comprises —$(CH_2)_m$-$Q_1$-$(CH_2)_n$-Z;

$Q_1$ comprises NH, O, S, CH=CH, C≡C, CO, $SO_2$ or $OSO_2$;

m is an integer from 1 to about 7;

n is an integer from 0 to about 7; and

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of formula I R4 comprises —$(CH_2)_m$-$Q_1$-$(CH_2)_n$-Z.

$Q_1$ comprises NH, O, S, CH=CH, C≡C, CO, $SO_2$ or $OSO_2$.

m is an integer from 1 to about 7.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of formula I R4 comprises —(CH$_2$)$_m$-Q$_1$-(CH$_2$)$_n$-Z.

Q$_1$ comprises NH, O, S, CH═CH, C≡C, CO, SO$_2$ or OSO$_2$.

m is an integer from 1 to about 7.

n is an integer from 0 to about 7.

Z comprises

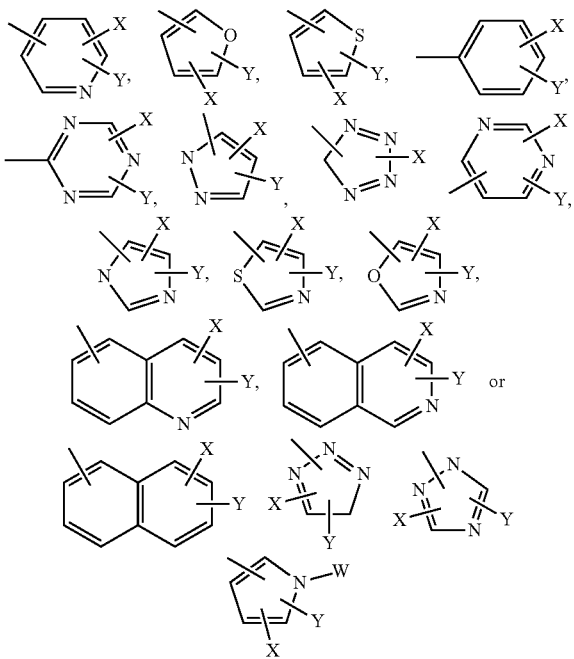

wherein X and Y each independently comprise, H, halogen, CF$_3$, CF$_2$H, N$_3$, NCS, CN, NO$_2$, NX$_1$X$_2$, —C(═O)N—O-X$_1$, —C(═N—O-X$_1$)X$_1$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl alkoxy, alkyl, alcohol, alkylmercapto, alkylamino, di-alkylamino, alkylsulfinyl or alkylsulfonyl, CX$_4$X$_5$X$_6$, —CH═CHX$_8$, —C≡CX$_8$;

X$_1$ and X$_2$ each independently comprise H or alkyl, or NX$_1$X$_2$, alkylamino, di-alkylamino, ammonium salt, quaternary ammonium salt, or a heterocyclic ring having about 4 to about 7 ring members and optionally one additional heteroatom selected from O, N or S X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members, X$_3$ comprises H, alkyl, NO$_2$, (CH$_2$)$_m$CN, hydroxyloweralkyl, or alkyl-NX$_1$X$_2$, X$_4$, X$_5$, and X$_6$ each independently comprise H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, or O-alkyl-X$_7$, wherein X$_7$ comprises H, alkyl, NO$_2$, NO, P(O)(OX$_8$)$_2$, PH(O)(OX$_8$), S(O)$_k$N(alkyl)$_2$, S(O)$_k$X$_8$, S(O)$_k$OX$_8$, COOX$_8$, CONX$_8$, SO$_3$H, COX$_8$, wherein X$_8$ comprises H, alkyl, carbocyclic ring, heterocyclic ring, aromatic ring, heteroaromatic ring, or —CX$_9$═CHX$_{10}$, wherein X$_9$ and X$_{10}$ each independently comprise H or alkyl;

m is an integer from 0 to 7;

j is an integer from 0 to about 6;

k is an integer from 0 to about 2;

W comprises H or alkyl.

In any variation of formula I, when A is a direct bond; and B is N(R5); and either of R1 and R2 is phenyl [optionally substituted with one more halogen atoms, (C$_1$-C$_6$) alkyl, (C$_1$-C$_6$) alkoxy, trifluoromethyl, cyano, nitro, (C$_1$-C$_6$) alkyl sulfonyl, (C$_1$-C$_6$) alkyl sulfonyl amino, (C$_1$-C$_6$) alkyl carbonyl-amino, (C$_1$-C$_6$) alkyl amino-carbonyl-amino or phenyl], (C$_2$-C$_6$) alkyl, cyclohexyl [optionally substituted with (C$_1$-C$_6$) alkyl, (C$_1$-C$_6$) alkoxy, trifluoromethyl, cyano or one or more fluorine atoms], 1-napthyl or 2-napthyl [optionally substituted with one or more halogen atoms, (C$_1$-C$_6$) alkyl, (C$_1$-C$_6$) alkoxy, trifluoromethyl or cyano], benzyl [optionally substituted on the phenyl ring with one or more halogen atoms, (C$_1$-C$_6$) alkyl, (C$_1$-C$_6$) alkoxy, trifluoromethyl or cyano], a 5- to 10-membered saturated or unsaturated heterocyclic radical [optionally substituted with one or more fluorine atoms, (C$_1$-C$_6$) alkyl, (C$_1$-C$_6$) alkoxy, trifluoromethyl or cyano] and a 5- to 10-membered aromatic monocyclic or bicyclic heterocyclic radical [optionally substituted with one more halogen atoms, (C$_1$-C$_6$) alkyl, (C$_1$-C$_6$) alkoxy, trifluromethyl, cyano, nitro or phenyl] and R3 is any above described variation; then R4 can not be H, (C$_1$-C$_6$) alkyl, benzyl, chloro, or bromo.

In any variation of formula I, when A is a direct bond; and B is N(R5); and either R1 or R2 is phenyl, thienyl, 2-pyridinyl, 3-pyridinyl, 4-pyridinyl, pyrimidinyl, pyrazinyl, pyridazinyl, triazinyl or any above group substituted with 1, 2, 3 or 4 substituents which can be the same or different, selected from C$_{1-3}$ alkyl, C$_{1-3}$ alkoxy, hydroxy, halogen, trifluoromethyl, trifluoromethylthio, trifluoromethoxy, nitro, amino, mono- or dialkyl (C$_{1-2}$)-amino, mono- or dialkyl (C$_{1-2}$)-amido, (C$_{1-3}$)-alkoxycarbonyl, carboxyl, cyano, carbomyl, acetyl and naphthyl; and R3 is any above described variation; then R4 can not be H, halogen, CN, carbomyl, formyl, acetyl, trifluoroacetyl, fluoroacetyl, propionyl, sulfamoyl, methanesulfonyl, methylsulfanyl, branched or unbranched C$_{1-4}$ alkyl group, which C$_{1-4}$ alkyl group may be substituted with 1 to 3 fluoro atoms or with a single bromo, chloro, iodo, cyano or hydroxy group.

In any variation of formula I, when R is pyrazolyl, inventive ligands of this embodiment can be represented by general formula II and their enantiomers, diastereomers, geometric isomers, racemates, tautomers, rotamers, atropisomers, isotopic variations, salts, N-oxides, hydrates and polymorphic forms (crystalline or amorphous):

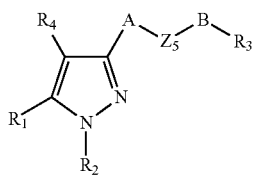

II

In any variation of formula I, when R is imidazolyl, inventive ligands of this embodiment can be represented by general formula III and their enantiomers, diastereomers, geometric isomers, racemates, tautomers, rotamers, atropisomers, isotopic variations, salts, N-oxides, hydrates and polymorphic forms (crystalline or amorphous):

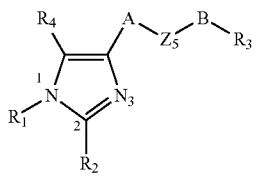

III

In any variation of formula I, when R is thiazolyl or oxazolyl, inventive ligands of this embodiment can be represented by general formula IV and their enantiomers, diastereomers, geometric isomers, racemates, tautomers, rotamers, atropisomers, isotopic variations, salts, N-oxides, hydrates and polymorphic forms (crystalline or amorphous):

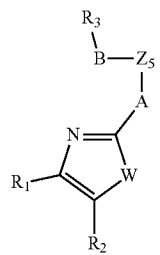

IV

In any variation of formula I, when R is triazolyl, inventive ligands of this embodiment can be represented by general formula V and their enantiomers, diastereomers, geometric isomers, racemates, tautomers, rotamers, atropisomers, isotopic variations, salts, N-oxides, hydrates and polymorphic forms (crystalline or amorphous):

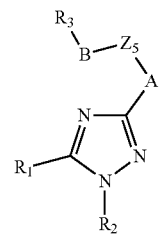

V

In any variation of formula I, when R is dihydropyrazolyl, inventive ligands of this embodiment can be represented by general formula VI and VII, their enantiomers, diastereomers, geometric isomers, racemates, tautomers, rotamers, atropisomers, isotopic variations, salts, N-oxides, hydrates and polymorphic forms (crystalline or amorphous):

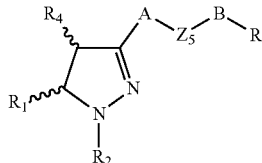

VI or

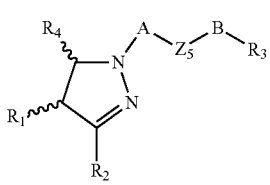

VII

In any variation of formula I, when R is pyrrolidinonyl, inventive ligands of this embodiment can be represented by general formula VIII and their enantiomers, diastereomers, geometric isomers, racemates, tautomers, rotamers, atropisomers, isotopic variations, salts, N-oxides, hydrates and polymorphic forms (crystalline or amorphous):

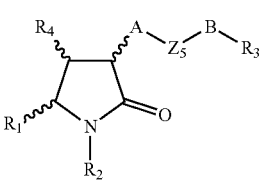

VIII

In any variation of formula I, when R is azetidinyl, inventive ligands of this embodiment can be represented by general formula IX and their enantiomers, diastereomers, geometric isomers, racemates, tautomers, rotamers, atropisomers, isotopic variations, salts, N-oxides, hydrates and polymorphic forms (crystalline or amorphous):

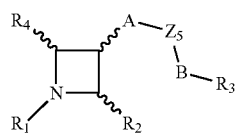

IX

In any variation of formula I, when R is oxyazetidinyl, inventive ligands of this embodiment can be represented by general formula X and their enantiomers, diastereomers, geometric isomers, racemates, tautomers, rotamers, atropisomers, isotopic variations, salts, N-oxides, hydrates and polymorphic forms (crystalline or amorphous):

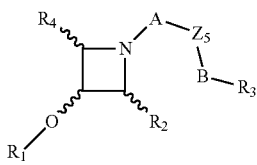

In any variation of formula I, when R is azaspiro[3.3]heptanyl, inventive ligands of this embodiment can be represented by general formula XI and their enantiomers, diastereomers, geometric isomers, racemates, tautomers, rotamers, atropisomers, isotopic variations, salts, N-oxides, hydrates and polymorphic forms (crystalline or amorphous):

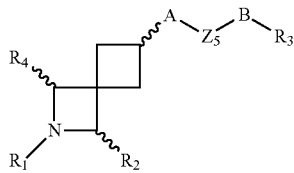

In any variation of formula I, inventive ligands of this embodiment can be represented by general formula II-XI, their enantiomers, diastereomers, geometric isomers, racemates, tautomers, rotamers, atropisomers, isotopic variations, salts, N-oxides, hydrates and polymorphic forms (crystalline or amorphous), bearing a carboxylic ester functionality that can be rapidly metabolized in vivo into inactive metabolites comprising of the carboxylic acid and alcohol moiety.

In any variation of formula I, inventive ligands of this embodiment can be represented by general formula II-XI, their enantiomers, diastereomers, geometric isomers, racemates, tautomers, rotamers, atropisomers, isotopic variations, salts, N-oxides, hydrates and polymorphic forms (crystalline or amorphous), bearing an oxime functionality represented by the group —C(=N—O-$X_1$)$X_2$ that can be rapidly metabolized in vivo.

In any variation of formula I, inventive ligands of this embodiment can be represented by general formula II-XI, their enantiomers, diastereomers, geometric isomers, racemates, tautomers, rotamers, atropisomers, isotopic variations, salts, N-oxides, hydrates and polymorphic forms (crystalline or amorphous), bearing a hydroxamic acid functionality represented by the group —C(=O)N—O-$X_1$ that can be rapidly metabolized in vivo.

In any variation of formula I, when R is pyrazolyl, imidazolyl, thiazolyl, oxazolyl, triazolyl or dihydropyrazolyl inventive ligands of this embodiment can be represented by general formula II-VIII and their enantiomers, diastereomers, geometric isomers, racemates, tautomers, rotamers, atropisomers, isotopic variations, salts, N-oxides, hydrates and polymorphic forms (crystalline or amorphous), and R1 is -T-$(CH_2)_m$-Q-$(CH_2)_n$-Z and
T an aromatic or a heteroaromatic ring having 5 to about 8 carbon atoms as ring members,
Q is CH=CH or C≡C;
m and n are independently an integer from 0 to about 7;
Z is $COOX_3$ and
$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S
R2 is an aromatic or a heteroaromatic ring having 5 to about 8 carbon atoms as ring members, In any variation of formula I, when R is pyrazolyl, imidazolyl, thiazolyl, oxazolyl, triazolyl or dihydropyrazolyl, inventive ligands of this embodiment can be represented by general formula II-VIII and their enantiomers, diastereomers, geometric isomers, racemates, tautomers, rotamers, atropisomers, isotopic variations, salts, N-oxides, hydrates and polymorphic forms (crystalline or amorphous), and R1 is -T-$(CH_2)_n$-Z and
T an aromatic or a heteroaromatic ring having 5 to about 8 carbon atoms as ring members,
Q is CH=CH or C≡C;
m and n are independently an integer from 0 to about 7;
Z is $COOX_3$ and
$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S
R2 is an aromatic or a heteroaromatic ring having 5 to about 8 carbon atoms as ring members, In any variation of formula I, when R is pyrazolyl, imidazolyl, thiazolyl, oxazolyl, triazolyl or dihydropyrazolyl, inventive ligands of this embodiment can be represented by general formula II-VIII and their enantiomers, diastereomers, geometric isomers, racemates, tautomers, rotamers, atropisomers, isotopic variations, salts, N-oxides, hydrates and polymorphic forms (crystalline or amorphous), and R1 is -T-$(CH_2)_n$-Z and
T an aromatic or a heteroaromatic ring having 5 to about 8 carbon atoms as ring members,
n is independently an integer from 0 to about 7;
Z is —C(=N—O-$X_1$)$X_2$ and
$X_1$ and $X_1$ each independently comprise H or alkyl,
R2 is alkyl, an aromatic or a heteroaromatic ring having 5 to about 8 carbon atoms as ring members In any variation of formula I, when R is pyrazolyl, imidazolyl, thiazolyl, oxazolyl, triazolyl, or dihydropyrazolyl, inventive ligands of this embodiment can be represented by general formula II-VIII and their enantiomers, diastereomers, geometric isomers, racemates, tautomers, rotamers, atropisomers, isotopic variations, salts, N-oxides, hydrates and polymorphic forms (crystalline or amorphous), and R1 is -T-$(CH_2)_n$-Z and
T an aromatic or a heteroaromatic ring having 5 to about 8 carbon atoms as ring members,
n is independently an integer from 0 to about 7;
Z is —C(=O)N—O-$X_1$
and
$X_1$ is H or alkyl,
R2 is alkyl, an aromatic or a heteroaromatic ring having 5 to about 8 carbon atoms as ring members In any variation of formula I, when R is pyrrolidinonyl, inventive ligands of this embodiment can be represented by general formula II-VIII and their enantiomers, diastereomers, geometric isomers, racemates, tautomers, rotamers, atropisomers, isotopic variations, salts, N-oxides, hydrates and polymorphic forms (crystalline or amorphous), and R1 and R2 are each independently -T-$(CH_2)_m$-Q-$(CH_2)_n$-Z or -T-$(CH_2)_n$-Z and T an aromatic or a heteroaromatic ring having 5 to about 8 carbon atoms as ring members, n is independently an integer from 0 to about 7;

Z is $COOX_8$, —C(=O)N—O-$X_1$ or Z is —C(=N—O-$X_1$) $X_2$ $X_1$ and $X_2$ comprise H or alkyl, Q is CH=CH or C≡C;

m and n are independently an integer from 0 to about 7;

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S R2 is an aromatic or a heteroaromatic ring having 5 to about 8 carbon atoms as ring members.

In any variation of formula I, when R is azetidinyl, inventive ligands of this embodiment can be represented by general formula IX and their enantiomers, diastereomers, geometric isomers, racemates, tautomers, rotamers, atropisomers, isotopic variations, salts, N-oxides, hydrates and polymorphic forms (crystalline or amorphous), and R1 is represented by the formula XII

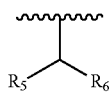

XII wherein;

R5 and R6 each independently comprise -T-$(CH_2)_m$-Q-$(CH_2)_n$-Z or -T-$(CH_2)_n$-Z and T an aromatic or a heteroaromatic ring having 5 to about 8 carbon atoms as ring members, m and n are independently an integer from 0 to about 7;

Z is $COOX_8$, —C(=O)N—O-$X_1$ or Z is —C(=N—O-$X_1$) $X_2$ $X_1$ and $X_2$ comprise H or alkyl, Q is CH=CH or C≡C;

m and n are independently an integer from 0 to about 7 with the requirement that when either of R5 or R6 is -T-$(CH_2)_m$-Q-$(CH_2)_n$-Z or -T-$(CH_2)_n$-Z, the other group is an aromatic or a heteroaromatic ring having 5 to about 8 carbon atoms as ring members.

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S and R2 and R4 are each independently H or alkyl.

In any variation of formula I, when R is azetidinyl, inventive ligands of this embodiment can be represented by general formula IX and their enantiomers, diastereomers, geometric isomers, racemates, tautomers, rotamers, atropisomers, isotopic variations, salts, N-oxides, hydrates and polymorphic forms (crystalline or amorphous), and R1 is represented by the formula XII

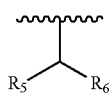

XII wherein;

R5 and R6 each independently comprise —$(CH_2)_n$-$Z_6$ or -T-$(CH_2)_m$-Q-$(CH_2)_n$-$Z_6$ or -T-$(CH_2)_n$-$Z_6$ n is independently an integer from 0 to about 7;

$Z_6$ is C4-C7 alkyl, $COOX_8$, —C(=O)N—O-$X_1$ or Z is —C(=N—O-$X_1$) $X_2$ $X_1$ and $X_2$ comprise H or alkyl, Q is CH=CH or C≡C;

m and n are independently an integer from 0 to about 7;

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S and R2 and R4 are each independently H or alkyl with the requirement that, when either of R5 or R6 is —$(CH_2)_n$-$Z_6$, the other group is -T-$(CH_2)_m$-Q-$(CH_2)_n$-$Z_6$ or -T-$(CH_2)_n$-$Z_6$ wherein T is an aromatic or a heteroaromatic ring having 5 to about 8 carbon atoms as ring members and m and n are an integer from 4 to about 7.

In any variation of formula I, when R is oxyazetidinyl, inventive ligands of this embodiment can be represented by general formula X and their enantiomers, diastereomers, geometric isomers, racemates, tautomers, rotamers, atropisomers, isotopic variations, salts, N-oxides, hydrates and polymorphic forms (crystalline or amorphous), and R1 is represented by the formula XII

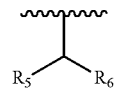

XII wherein;

R5 and R6 each independently comprise -T-$(CH_2)_m$-Q-$(CH_2)_n$-Z or -T-$(CH_2)_n$-Z and T an aromatic or a heteroaromatic ring having 5 to about 8 carbon atoms as ring members, m and n are independently an integer from 0 to about 7;

Z is $COOX_8$, —C(=O)N—O-$X_1$ or Z is —C(=N—O-$X_1$) $X_2$ $X_1$ and $X_2$ comprise H or alkyl, Q is CH=CH or C≡C;

m and n are independently an integer from 0 to about 7;

$X_3$ is H or alkyl, or $NX_1X_2$, alkylamino, di-alkylamino, ammonium salt, quaternary ammonium salt, or a heterocyclic ring having about 4 to about 7 ring members and optionally one additional heteroatom selected from O, N or S and R2 and R4 are each independently H or alkyl with the requirement that when either of R5 or R6 is -T-$(CH_2)_m$-Q-$(CH_2)_n$-Z or -T-$(CH_2)_n$-Z, the other group is an aromatic or a heteroaromatic ring having 5 to about 8 carbon atoms as ring members.

In any variation of formula I, when R is oxyazetidinyl, inventive ligands of this embodiment can be represented by general formula X and their enantiomers, diastereomers, geometric isomers, racemates, tautomers, rotamers, atropisomers, isotopic variations, salts, N-oxides, hydrates and polymorphic forms (crystalline or amorphous), and R1 is represented by the formula XII

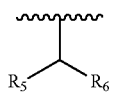

wherein;
R5 and R6 each independently comprise —$(CH_2)_n$-$Z_6$ or -T-$(CH_2)_m$-Q-$(CH_2)_n$-$Z_6$ or -T-$(CH_2)_n$-$Z_6$
n is independently an integer from 0 to about 7;
$Z_6$ is C4-C7 alkyl, COO$X_8$, —C(=O)N—O-$X_1$ or Z is —C(=N—O-$X_1$) $X_2$
$X_1$ and $X_2$ comprise H or alkyl,
Q is CH=CH or C≡C;
m and n are independently an integer from 0 to about 7;
$X_3$ is H or alkyl, or N$X_1X_2$, alkylamino, di-alkylamino, ammonium salt, quaternary ammonium salt, or a heterocyclic ring having about 4 to about 7 ring members and optionally one additional heteroatom selected from O, N or S and
R2 and R4 are each independently H or alkyl with the requirement that, when either of R5 or R6 is —$(CH_2)_n$-$Z_6$,
the other group is -T-$(CH_2)_m$-Q-$(CH_2)_n$-$Z_6$ or -T-$(CH_2)_n$-$Z_6$ wherein
T is an aromatic or a heteroaromatic ring having 5 to about 8 carbon atoms as ring members and
m and n are an integer from 4 to about 7.

In any variation of formula I, when R is azaspiro[3.3]heptanyl, inventive ligands of this embodiment can be represented by general formula XI and their enantiomers, diastereomers, geometric isomers, racemates, tautomers, rotamers, atropisomers, isotopic variations, salts, N-oxides, hydrates and polymorphic forms (crystalline or amorphous), and
R1 is represented by the formula XII

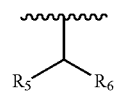

wherein;
R5 and R6 each independently comprise -T-$(CH_2)_m$-Q-$(CH_2)_n$-Z or -T-$(CH_2)_n$-Z and
T an aromatic or a heteroaromatic ring having 5 to about 8 carbon atoms as ring members,
m and n are independently an integer from 0 to about 7;
Z is COO$X_8$, —C(=O)N—O-$X_1$ or Z is —C(=N—O-$X_1$) $X_2$
$X_1$ and $X_2$ comprise H or alkyl,
Q is CH=CH or C≡C;
m and n are independently an integer from 0 to about 7;
$X_3$ is H or alkyl, or N$X_1X_2$, alkylamino, di-alkylamino, ammonium salt, quaternary ammonium salt, or a heterocyclic ring having about 4 to about 7 ring members and optionally one additional heteroatom selected from O, N or S and
R2 and R4 are each independently H or alkyl with the requirement that when either of R5 or R6 is -T-$(CH_2)_m$-Q-$(CH_2)_n$-Z or -T-$(CH_2)_n$-Z, the other group is an aromatic or a heteroaromatic ring having 5 to about 8 carbon atoms as ring members.

In any variation of formula I, when R is azaspiro[3.3]heptanyl, inventive ligands of this embodiment can be represented by general formula XI and their enantiomers, diastereomers, geometric isomers, racemates, tautomers, rotamers, atropisomers, isotopic variations, salts, N-oxides, hydrates and polymorphic forms (crystalline or amorphous), and
R1 is represented by the formula XII

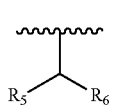

wherein;
R5 and R6 each independently comprise —$(CH_2)_n$-$Z_6$ or -T-$(CH_2)_m$-Q-$(CH_2)_n$-$Z_6$ or -T-$(CH_2)_n$-$Z_6$
n is independently an integer from 0 to about 7;
$Z_6$ is C4-C7 alkyl, COO$X_8$, —C(=O)N—O-$X_1$ or Z is —C(=N—O-$X_1$) $X_2$
$X_1$ and $X_2$ comprise H or alkyl,
Q is CH=CH or C≡C;
m and n are independently an integer from 0 to about 7;
$X_3$ is H or alkyl, or N$X_1X_2$, alkylamino, di-alkylamino, ammonium salt, quaternary ammonium salt, or a heterocyclic ring having about 4 to about 7 ring members and optionally one additional heteroatom selected from O, N or S and
R2 and R4 are each independently H or alkyl with the requirement that,
when either of R5 or R6 is —$(CH_2)_n$-$Z_6$,
the other group is -T-$(CH_2)_m$-Q-$(CH_2)_n$-$Z_6$ or -T-$(CH_2)_n$-$Z_6$ wherein
T is an aromatic or a heteroaromatic ring having 5 to about 8 carbon atoms as ring members and
m and n are an integer from 4 to about 7.

DETAILED DESCRIPTION

The inventive compounds in any formula, embodiment or variation include any and all possible isomers and stereoisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

As used herein and in the appended claims, the singular forms "a", "an", and "the" include plural referents unless the context clearly dictates otherwise. Thus, for example, reference to "a solvent" includes a plurality of such solvents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition or process consisting essentially of the elements as defined herein would not exclude other materials or steps that do not materially affect the basic and novel characteristic(s) of the claimed technology. "Consisting of" shall mean excluding more than trace elements of other ingredients and substantial method steps. Embodiments defined by each of these transition terms are within the scope of this technology.

The term "compound(s) of the technology" as used herein means any of compounds disclosed in the invention, and may include all of their enantiomers, diastereomers, geometric isomers, racemates, tautomers, rotamers, and atropisomers, N-oxides, salts, solvates, and/or hydrates, metabolites and pharmaceutically acceptable salts thereof. The compounds of the present technology are prepared in different forms, such as pharmaceutically acceptable salts, hydrates, or solvates and the technology includes compositions and methods encompassing all variant forms of the compounds.

As used herein, $C_m$-$C_n$, such as $C_1$-$C_{12}$, $C_1$-$C_8$, or $C_1$-$C_6$ when used before a group refers to that group containing m to n carbon atoms.

Unless otherwise specifically defined, "alkyl" or "lower alkyl" refers to a linear, branched or cyclic or cycloalkyl group having from 1 to 30 carbon atoms, 1 to 12 carbon atoms, and advantageously 1 to 7 carbon atoms including, for example, methyl, ethyl, propyl, butyl, hexyl, octyl, isopropyl, isobutyl, tert-butyl, cyclopropyl, cyclohexyl, and cyclooctyl. The alkyl group can be saturated or unsaturated. The alkyl group or the lower alkyl group can be unsubstituted, singly substituted or, if possible, multiply substituted ex. gem-dimethyl group, with substituent groups in any possible position. Unless otherwise specifically limited, a cyclic or cycloalkyl group includes carbocyclic, monocyclic, bicyclic, tricyclic, tetracyclic, spirocyclic and polycyclic rings.

Unless otherwise specifically defined, a "carbocyclic" ring and all its isomers has a ring structure, chiral or achiral, saturated or unsaturated, substituted or unsubstituted, with about 0 to 5 heteroatoms, and having about 3 to about 20 ring members, for example, 1- or 2-cyanocyclopropyl, 2,2,3,3-tetramethylcyclopropyl, cyclohexadiene, cyclohexanol, cycloheptane, cyclohexane, tetrahydropyran, cyclohexanone, cyclohexene, cyclohexadiene, lactone, lactam, sultone, sultam, quinone, and terpenes. The carbocyclic group and all of its isomers can be unsubstituted, singly substituted or, if possible, multiply substituted, with substituent groups in any possible position. Carbocyclic groups related to terpenes include p-mentha-2,8-dien-1-ol, p-mentha-1,8-diene-3-ol (isopiperitenol), nopinone and related derivatives, menthane, limonene, phellandrene, terpinolene, terpinene, menthol, isomenthol, neomenthol, neoisomenthol, pulegol, isopulegol, piperitol, terpineol, menth-1-en-8-thiol, carveol, perillaaldehyde, perillyl alcohol, menthone, isomenthone, pulegone, isopulegone, phellandral, piperitone, dihydrocarvone, carvenone, carvone, cymene, carvacrol, thymol, cymen-8-ol and cuminaldehyde. The terpenes will encompass all related isomers. In certain embodiments, the carbocyclic group can be fused to another carbocyclic group, for example as in octahydro-1H-indene. For example, carbocyclic groups comprising of lactones include α-acetolactone, β-propiolactone, γ-butyrolactone, δ-valerolactone and ε-caprolactone. For example, carbocyclic groups comprising of lactones include pyrrolidinone. In some instances, a carbocyclic group can also be a cyclic or cycloalkyl group, a heteroalkyl or a heterocyclic group, or an alkyl group.

Unless otherwise specifically defined, a lactone is a cyclic ester having 4 to 8 ring members. The lactone can be unsubstituted, singly substituted or, if possible, multiply substituted, with substituent groups in any possible position.

Unless otherwise specifically defined, a lactam is a cyclic amide having 4 to 8 ring members. The lactam can be unsubstituted, singly substituted or, if possible, multiply substituted, with substituent groups in any possible position.

Unless otherwise specifically defined, a sultam is a cyclic sulfonamide having 4 to 8 ring members in which the S—N bond is part of the ring. The sultam can be unsubstituted, singly substituted or, if possible, multiply substituted, with substituent groups in any possible position.

Unless otherwise specifically defined, a "bicyclic" ring comprises two fused or bridged rings. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, 2,3-dihydro-1H-indene, bicyclo[3.1.0]hexane, 2,3-dihydro-1H-inden-2-yl)methanol, bicyclooctane 7,7-dimethylbicyclo[2.2.1]hept-2-ene, 7,7-dimethylbicyclo[2.2.1]hept-2-en-1-yl)methanol, 7,7-dimethylbicyclo[2.2.1]heptane, 2,6-dioxabicyclo[3.3.0]octane, 6,6-dimethylbicyclo[3.1.1]heptan-2-one, tetralin, decalin and related terpenes such as carane, trans-thujane, pinane, camphene, isocamphane, fenchane, careen, chaminic acid, sabinene, thujene, thujol, thujanone, α-pinene, β-pinene, car-4-ene-3-ol, verbenol, verbenone, myrtenol, myrtenal, pinocarveol, pinocarvone, camphor, isoborneol, borneol, norbornane, fenchone, β-fenchol, α-fenchol, camphene and fenchene. The terpenes will encompass all related isomers and derivatives.

Unless otherwise specifically defined, a "tricyclic" ring comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. The individual rings may or may not be of the same type. Examples of tricyclic ring structures include fluorene and anthracene.

Unless otherwise specifically defined, a "spirocyclic" ring is a non-aromatic ring structure wherein two rings are fused at one carbon atom and each ring can have 3 to 6 ring members independently selected from carbon atoms and one or more heteroatoms, including oxygen, nitrogen, phosphorous and/or sulfur or a combination thereof and S can exist as S, SO or $SO_2$. Examples include azaspiro[3.3]heptane, azaspiro[3.5]nonane, spiro[3.3]heptane, azaspiro[5.5]undecane, azaspiro[3.4]octane, azaspiro[2.4]heptane, diazaspiro[4.5]decane, diazaspiro[3.5]nonane, diazaspiro[3.3]heptane, diazaspiro[4.4]nonane, diazaspiro[6.6]tridecane, thia-6-azaspiro[3.3]heptane, dioxo-thia-6-azaspiro[3.3]heptane, oxa-6-azaspiro[3.3]heptane. The ring can be unsubstituted, singly substituted or, if possible, multiply substituted.

Unless otherwise specifically defined, a "polycyclic" ring comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantane, oxa-adamantane, bicyclooctane, norbornane and bicyclononanes.

Unless otherwise specifically defined, a "heterocyclic" ring is a saturated or unsaturated ring structure having about 3 to about 8 ring members independently selected from carbon atoms and one or more heteroatoms, including oxygen, nitrogen, phosphorous and/or sulfur; for example, azetidine, methylazetidine, piperidine, morpholine, piperazine, (S) and (R)-1,2-dimethylpiperazine, 1-H-pyridine-2-one, dihydropyridine, tetrahydropyridine, pyridazin-3(2H)-one, piperidine-2,4-dione, pyrrolidine, thiomorpholine, 1,1-dioxothiomorpholine, 4,4-difluoropiperidine, tetrahydro-2H-thiopyran 1,1-dioxide, nucleosides and their derivatives or an alkaloid.

The heterocyclic ring can be unsubstituted, singly substituted or, if possible, multiply substituted, with substituent groups in any possible position. In some embodiments, a "heterocyclic" ring can be fused to other rings and also be referred to as a "heterobicyclic" ring, a "heterotricyclic" ring or a "heteropolycyclic" ring.

Unless otherwise specifically defined, a "heterobicyclic" ring structure comprises 2 fused or bridged rings having ring members independently selected from carbon and one or more heteroatoms, including oxygen, nitrogen, phosphorous and/or sulfur. The heterobicyclic ring structure can be saturated or unsaturated. The heterobicyclic ring can be unsubstituted, singly substituted or, if possible, multiply substituted, with substituent groups in any possible position. The individual rings may or may not be of the same type. Examples of heterobicyclic ring structures include azaspiro[3.3]heptane, octahydropyrrolo[3,4-c]pyrrole and diazabicyclo[3.3.1]nonane and isobenzofuran.

Unless otherwise specifically defined, a "heterotricyclic" ring structure comprises 3 fused, bridged, or both fused and bridged rings having ring members independently selected from carbon and one or more heteroatoms, including oxygen, nitrogen, phosphorous and/or sulfur. The heterotricyclic ring structure may be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline, phenazine, 2,4,10-trioxaadamantane and tetradecahydro-phenanthroline.

Unless otherwise specifically defined, a "heteropolycyclic" ring structure comprises more than 3 rings that may be fused, bridged or both fused and bridged and that have ring members independently selected from carbon and one or more heteroatoms, including oxygen, nitrogen, phosphorous and/or sulfur. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantane, oxa-adamantane, tropane, homotropane and 5-norbornene-2,3-dicarboximide.

Unless otherwise specifically defined, "alkenyl" refers to a, straight or branched hydrocarbon chain containing 2 to 12 carbons and containing at least one carbon-carbon double bond. Representative alkenyl groups include vinyl, allyl, ethenyl, 2-propenyl, 2-methyl-2-propenyl, 2-methylhex-2-enyl, 3-butenyl, 2-methylpent-2-enyl, 3-methylocta-2,6-dienyl, 4-pentenyl, 5-hexenyl, 2-heptenyl, 2-methyl-1-heptenyl, and 3-decenyl or a terpene. The "alkenyl" group can be unsubstituted, singly substituted or, if possible, multiply substituted, with substituent groups in any possible position. Unless otherwise specifically defined, an unsaturated alkyl group can also be an alkenyl group.

Unless otherwise specifically defined, "alkenylene" refers to a divalent group derived from a straight or branched hydrocarbon chain containing 2 to 4 carbon atoms and containing at least one carbon-carbon double bond. Representative alkenylene groups include CH=CH— and —CH$_2$CH=CH—. The "alkenylene" group can be unsubstituted, singly substituted or, if possible, multiply substituted, with substituent groups in any possible position. Unless otherwise specifically defined, an unsaturated alkyl group can also be an alkenyl group.

Unless otherwise specifically defined, "alkynyl" refers to a straight or branched chain hydrocarbon group containing 2 to 10 carbon atoms and containing at least one carbon-carbon triple bond. Representative alkynyl groups include acetylenyl, 1-propynyl, 2-propynyl, 3-butynyl, 2-pentynyl, and 1-butynyl. The "alkynyl" group can be unsubstituted, singly substituted or, if possible, multiply substituted, with substituent groups in any possible position. Unless otherwise specifically defined, an unsaturated alkyl group can also be an alkynyl group.

Unless otherwise specifically defined, "alcohol" refers to the general formula alkyl-OH or carbocyclic-OH, cyclic alkyl-OH, glycol, polyol, and includes primary, secondary and tertiary variations. The alcohol can be protected with a protecting group selected from Peter G. M. Wuts, Theodora W. Greene, Greene's Protective Groups in Organic Synthesis, 4th Edition, 2006, Wiley; herein incorporated by reference in its entirety. Examples of protecting groups include methyl, benzyl and acetyl. The "alcohol" group can be unsubstituted, singly substituted or, if possible, multiply substituted, with substituent groups in any possible position.

Unless otherwise specifically defined, a glycol is an alcohol containing compound with two hydroxyl groups. The glycol group can be unsubstituted, singly substituted or, if possible, multiply substituted, with substituent groups in any possible position. Examples of glycol include 1,2-ethanediol, 1,3-propanediol and 1,4-butanediol.

Unless otherwise specifically defined, a polyol is an alcohol containing compound more than two hydroxyl groups. The polyol group can be unsubstituted, singly substituted or, if possible, multiply substituted, with substituent groups in any possible position.

Unless otherwise specifically defined, "alkoxy" refers to the general formula —O-alkyl.

Unless otherwise specifically defined, "aryloxy" refers to the general formula —O-aryl-.

Unless otherwise specifically defined, "heteroaryloxy" refers to the general formula —O-heteroaryl-.

Unless otherwise specifically defined, "arylalkoxy" refers to the general formula —O-alkyl-aryl-.

Unless otherwise specifically defined, "heteroarylalkoxy" refers to the general formula —O-alkyl-heteroaryl-.

Unless otherwise specifically defined, "arylalkyl" refers to the general formula, -aryl-alkyl—wherein the "aryl" and "alkyl" groups can be unsubstituted, singly substituted or, if possible, multiply substituted, with substituent groups in any possible position. Examples of "arylalkyl" include benzyl, benzhydryl, 1-phenylethyl, 2-phenylethyl, 4-phenylbutyl, and benzhydryloxy groups.

Unless otherwise specifically defined, "heteroarylalkyl" refers to the general formula, -heteroaryl-alkyl—wherein the "heteroaryl" and "alkyl" groups can be unsubstituted, singly substituted or, if possible, multiply substituted, with substituent groups in any possible position. Examples of "heteroarylalkyl" include benzyl, benzhydryl, 1-phenylethyl, 2-phenylethyl, 3-phenylpropyl, 4-phenylbutyl, and benzhydryloxy groups.

Unless otherwise specifically defined, "amine" refers to a compound containing a basic nitrogen, and is substituted.

Unless otherwise specifically defined, "amide" refers to the general formula —C(O)—N— or —N—C(O)—, and can be singly substituted or, if possible, multiply substituted, with substituent groups on the carbon or the nitrogen atom.

Unless otherwise specifically defined, "ester" refers to the general formula —C(O)—O— or —O—C(O)—, and can be substituted with substituent groups on the carbon or the oxygen atom.

The term "oxime" can comprise of aldoxime or ketoxime.

Unless otherwise specifically defined, "acyl" refers to the general formula —C(O)alkyl.

Unless otherwise specifically defined, "acyloxy" refers to the general formula —O-acyl.

Unless otherwise specifically defined, "alkylmercapto" refers to the general formula —S-alkyl, SO-alkyl- and —SO$_2$-alkyl, for example thiomorpholine, 1,1-dioxothiomorpholine.

Unless otherwise specifically defined, "arylmercapto" refers to the general formula —S-aryl, SO-aryl- and —SO$_2$-aryl.

Unless otherwise specifically defined, "heteroarylmercapto" refers to the general formula —S-heteroaryl, SO-heteroaryl- and —SO$_2$-heteroaryl.

Unless otherwise specifically defined, "alkylamino" refers to the general formula —(NH)-alkyl, for example methylamine, ethylamine, ethylenediamine, 2-aminoethanol.

Unless otherwise specifically defined, "arylamino" refers to the general formula —(NH)-aryl, for example aniline.

Unless otherwise specifically defined, "heteroarylamino" refers to the general formula —(NH)-heteroaryl, for example aminopyridine.

Unless otherwise specifically defined, "di-alkylamino" refers to the general formula —N-(alkyl)$_2$. Unless otherwise specifically limited di-alkylamino includes cyclic amine compounds such as piperidine and morpholine and 1,1-dioxothiomorpholine.

Unless otherwise specifically defined, an "aromatic" ring is an unsaturated ring structure having about 6 to 12 ring members, for example benzene. In some instances, "aromatic" ring is an unsaturated ring structure that can be fused to another unsaturated ring structure, ex. naphthalene. The aromatic ring structure can be unsubstituted, singly substituted or, if possible, multiply substituted, with substituent groups in any possible position.

Unless otherwise specifically defined, "aryl" refers to an "aromatic" ring, for example phenyl, biphenyl, fluorenyl, dibenzosuberanyl, dibenzosuberenyl, or naphthyl. The aryl group can be unsubstituted, singly substituted or, if possible, multiply substituted, with substituent groups in any possible position. In certain embodiments, the aryl group will be fused to a carbocyclic ring having 4 to 8 ring atoms, for example as in 2,3-dihydro-1H-indene, 2,3-dihydro-1H-inden-2-yl)methanol and 2,2-dimethyl-2,3-dihydro-1H-indene. In certain embodiments, the aryl group will be fused to a heterocyclic ring having from 5 to 8 ring atoms, for example as in chromane and 2,3-dihydrobenzofuran.

Unless otherwise specifically defined, "aroyl" refers to the general formula —C(=O)aryl. The "aroyl" group can be unsubstituted, singly substituted or, if possible, multiply substituted, with substituent groups in any possible position Unless otherwise specifically defined, "halogen" refers to an atom selected from fluorine, chlorine, bromine and iodine.

Unless otherwise specifically defined, a "heteroaromatic" ring is an unsaturated ring structure having about 5 to about 8 ring members independently selected from carbon atoms and one or more heteroatoms, including oxygen, nitrogen, phosphorous and/or sulfur, for example thiophene, oxazole, isoxazole, imidazole, pyrazole, benzimidazole, triazolopyridine, benzotriazole, pyridine, pyridine 1-oxide, pyrimidine, indole, indazole, furan, quinoline, 1,2,4-triazole, 1,2,3-triazole, imidazole, tetrazole, methyltetrazole, 3,4-dihydro-1H-benzo[c][1,2]thiazine-2,2-dioxide, 1H-pyrrolo[2,3-c]pyridine, 1H-pyrrolo[2,3-b]pyridine, 1-(cyclohexylmethyl)-1H-benzo[d]imidazole, 1-((1-methylpiperidin-2-yl)methyl)-1H-indole, 2,3,4,9-tetrahydro-1H-carbazole, 1,2,3,4-tetrahydropyrrolo[3,4-b]indole, 4-(alkylsulfonyl)-1,2,3,4-tetrahydropyrrolo[3,4-b]indole, quinazolin-4(3H)-one, 4-((1H-indol-1-yl)methyl)tetrahydro-2H-thiopyran 1,1-dioxide, isoindolin-1-one, nucleosides and their derivatives or and alkaloid. The heteroaromatic ring can be unsubstituted, singly substituted or, if possible, multiply substituted, with substituent groups in any possible position. In certain embodiments, the heteroaryl group will be fused to a carbocyclic group having 5 to 8 ring atoms, for example as in 4,5,6,7-tetrahydrobenzo[b]thiophene, 4,4a,5,5a-tetrahydro-1H-cyclopropa[4,5]cyclopenta[1,2-c]pyrazole and 4,5,6,7-tetrahydro-1H-indole. In certain embodiments, the heteroaryl group will be fused to a heterocyclic ring having from 5 to 8 ring atoms, for example as in 5,6,7,8-tetrahydroquinoline. Unless otherwise specifically defined, a "heteroaromatic" ring is also referred to as "heteroaryl" ring. In some instances, an unsaturated "aryl" ring or unsaturated "aromatic" ring can be referred to as a "heteroaryl" ring or an "heteroaromatic" ring when the ring includes at least one heteroatom.

Unless otherwise specifically defined, the term "phenacyl" refers to the general formula phenylacyl.

In general, "substituted" or "optionally substituted" or "substituent" refers to a group or groups (e.g., an alkyl group, an aryl group) in which one or more bonds to an atom ex. hydrogen, contained therein may be replaced by a bond to non-hydrogen or non-carbon atoms. As used herein, and unless otherwise excluded, any alkyl, alkenyl, alkynyl, alkenylene, carbocyclyl, aryl, heteroaryl, cyclyl, or heterocyclyl may be substituted. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Substituent groups for the above moieties useful in the technology are those groups that do not significantly diminish the biological activity of the compound. Examples of substituent groups include, but are not limited to, alkyl, aryl, heteroaryl, alkynyl, alkenyl, alcohol, halogens (i.e., F, Cl, Br, and I); hydroxyls; alkoxy, alkenoxy, alkynoxy, aryloxy, arylalkoxy, heteroarylalkoxy, aryloxy or heteroaryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. In some embodiments, suitable substituents also include, terpene, boronic acid, boronate ester, $BF_3K$, biotin group tethered via an amide bond, $CF_2$, $CF_3$, $CF_2H$, $N_3$, NCS, CN, $NQ^1Q^1$, =O, $OQ^3$, $SQ^3$, $NHQ^3$, =$CH_2$, =NOH, OAc, O-acyl, O-aryl, $CH_2$-aryl, O-aroyl, NH-acyl, NH-aroyl, CHO, C(halogen)$_3$, (halogen)$_2$, $COOQ^3$, $SO_2$-halogen, $OSO_2CF_3$, $SO_3H$, $SO_3$alkyl, $SO_2NQ^1Q^1$, $CONQ^1Q^1$, =$CH_2$, OH, alkyl-OH, —C(=O)N—O-$X_1$, —C(=N—O-$X_1$)$X_2$, OH, $ONO_2$, alkyl-$ONO_2$, spirocyclic, alkylmercapto, aryl, aroyl, alkylamino, di-alkylamino, polycyclic, carbocyclic group, heterocyclic ring, aromatic ring, heteroaromatic ring, $CO-T^1$, $-C(O)OP(O)(Oalkyl)_2$, $O-PO(OX^1)(OY^1)$, $O-alkyl-(CH_2)_p-O-PO(OX^1)(OY^1)$ wherein p is 0-6, $OSO_3H$, $OCO$-alkyl-COOH, $OCO$-alkenyl-COOH, $OPO_3H_2$, $O-SO_2$alkyl-$T^1$, $O-SO_2$-$T^1$, $OT^1$, Oalkyl-$T^1$, $NHSO_2$-$T^1$, Nalkyl-$SO_2$-$T^1$, $-COalkyl$-$T^1$, $NHCO$-$T^1$, $OCONH$-$T^1$, $O-CO$-$T^1$, $O-CO-O$-$T^1$, $OCO$-alkyl-NH-$T^1$, $OCO$-alkyl-$N(T^1)_2$, $OCO$-alkyl-$T^1$, $O$-alkyl-$T^1$, $O$-alkyl-$OCO$-$T^1$, $O$-$T^1$-$T^1$, $O$-alkyl-$PO(OX^1)(OY^1)$, $OCO$(glycol), $OCO$-alkyl(glycol), $OCO$-$PEG_r$, $O-CO-O$-$PEG_r$, $O-COCO$-$O$-$PEG_r$, and $O$-$PEG_r$, or a group comprising $ONO_2$; wherein $T^1$ is H, alkyl, halogen, OH, $CF_3$, $CF_2H$, COOH, COOalkyl, alkaloid, immunogen, terpene, $O-PO(OX^1)(OY^1)$, $SO_3H$, $ONO_2$ a heterocyclic ring, $NQ^1Q^1$ or $T^1$ is an ammonium group, wherein said ammonium group can be independently substituted one or more times with a C1 to C6 alkyl radical, or is a C3 to C7 heterocycle containing a nitrogen heteroatom for bond formation, wherein the said heterocycle can contain one or more heteroatoms independently selected from N, O or S, and wherein said heterocycle can be substituted with one or more independently chosen substituents;

r is 0 to 10;

wherein any of the above groups can be optionally substituted in any possible position;

$Q^1$ and $Q^1$ are each independently H, alkyl, or alkyl-$ONO_2$, or $Q^1$ and $Q^1$ together are part of a heterocyclic ring having about 4 to about 7 ring members and optionally one additional heteroatom selected from O, N or S, or $Q^1$ and $Q^1$ together are part of an imide ring having about 5 to about 6 members;

$Q^3$ is H, alkyl, heterocyclic ring, aromatic ring, heteroaromatic ring hydroxyloweralkyl, or alkyl-$NQ^1Q^1$;

$X^1$ and $Y^1$ are independently H, alkyl-OCO-alkyl, alkyl-O—CO—O-alkyl, alkali metals or alkaline earth metals; and $PEG_r$ refers to a polyether PEGylated group tethered via a linker. Unless otherwise specifically defined, "PEG", "$PEG_n$", "$PEG_r$", and "$PEG_s$" independently refer to the polyether entity tethered or conjugated to the compounds directly, via an alkyl group or via another linker to improve the physicochemical properties such as water solubility of the compounds. "PEG", "$PEG_n$", "$PEG_r$", and "$PEG_s$" can be represented by the formula $-(CH_2-CH_2-O-)_m-CH_3$ where m is 1-15. Examples of a linker are the amide group, carbamate, carbonate and the ester group. The linker can be hydrolyzed physiologically or enzymatically. The definitions and immediate applications of the PEG technology can be adapted from Valentino J. Stella (editor), Prodrugs: Challenges and Rewards, 2007, Springer (volumes 1 and 2); herein incorporated by reference in its entirety.

In certain embodiments, the aromatic or heteroaromatic groups can be substituted by $-C(=O)N-O-X_1$, $-C(=N-O-X_1)X_2$, $-(CH_2)_n-Z$ or $-Q_2-(CH_2)_n-Z$ or $-(CH_2)_m-Q_1-(CH_2)_n-Z$ wherein $X_1$, $X_2$, $Q_1$, $Q_2$, Z, m and n are as previously defined.

Unless otherwise specifically defined, the term "physicochemical properties" refers to certain physical and chemical descriptive properties that the compounds possess.

In various embodiments, the compounds disclosed herein may suitably include isomers, pharmaceutically acceptable salts, solvates, hydrates, amides, esters, ethers, chemically protected forms, tautomers, polymorphs and prodrugs thereof.

The term "salt" can comprise of complexes that are formed by reacting a basic nitrogen containing compound of formula 1-XI with mineral acids such as hydrochloric acid.

The term "salt" can comprise of ammonium salts and quaternary ammonium salts of a compound of formula I-XI.

The term "composition(s) of the technology" as used herein means compositions comprising any of compounds described herein, such as for example, compounds disclosed in the invention or salts, tautomeric forms, hydrates, and solvates thereof.

The term "method(s) of the technology" as used herein means methods comprising treatment with the compounds and/or compositions of the technology.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, tautomers, solvates, or hydrates thereof, with other chemical components, such as physiologically acceptable carriers and excipients. The purpose of a pharmaceutical composition is to facilitate administration of a compound to an organism.

The term "pharmaceutically acceptable" refers to safe and non-toxic for in vivo, preferably, human administration.

The term "pharmaceutically acceptable salt" is intended to include salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoracetic, trichloroacetic, naphthalene-2 sulfonic, oxalic, propionic, and other acids. Salts may also exist as solvates or hydrates. Other exemplary pharmaceutically acceptable salts are described herein.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of (+) or (−) 20 percent, 10 percent, 5 percent or 1 percent.

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of an affliction, or one or more symptoms thereof, prevent the advancement of conditions related to an affliction, prevent the recurrence, development, or onset of one or more symptoms associated with an affliction, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "in need thereof" refers to the need for symptomatic or asymptomatic relief from a condition.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin (herein incorporated by reference in its entirety).

As used herein, the terms "animal," "subject" and "patient" as used herein include all members of the animal kingdom including, but not limited to, mammals, animals (e.g., cats, dogs, horses, swine, etc.) and humans. In some embodiments, an "individual" refers to a human. In some embodiments, an "animal" refers to, for example, nonhuman-primates such as monkeys and baboons; veterinary animals, such as rodents, dogs, cats, horses and the like; and farm animals, such as cows, pigs and the like. In some embodiments, the subject or patient is a human.

Some of the inventive compounds show a high affinity for at least one of the cannabinoid receptors. Thus, another aspect of the invention is use of at least one of the inventive compounds to interact with a cannabinoid receptor.

A better understanding of the invention will be obtained from the following detailed description of the article and the desired features, properties, characteristics, and the relation of the elements as well as the process steps, one with respect to each of the others, as set forth and exemplified in the description and illustrative embodiments.

As used herein a "therapeutically effective amount" of a compound, is the quantity of a compound which, when administered to an individual or animal, results in a sufficiently high level of that compound in the individual or animal to cause a physiological response, for example a discernible increase or decrease in stimulation of cannabinoid receptors. The inventive compounds described herein, and physiologically acceptable salts thereof, have pharmacological properties when administered in therapeutically effective amounts individually or in combination for providing a physiological response useful to treat cannabinoid toxicity. Typically, a "therapeutically effective amount" of an inventive compound is believed to range from about 0.01 mg to about 1,000 mg as a single bolus dose or multiple doses via titration.

As used herein, an "individual" refers to a human. An "animal" refers to, for example nonhuman-primates such as monkeys and baboons, veterinary animals, such as rodents, dogs, cats, horses and the like, and farm animals, such as cows, pigs and the like In a certain embodiments, the compound disclosed in the invention can be used in combination with other acceptable pharmaceutical substances.

In embodiments in which compounds of the disclosure is used in combination with other compounds, it will be possible to reduce or even eliminate one or more side-effects. A particular method involves administering a therapeutically effective amount of at least one of the compounds of the disclosure in combination with other compounds disclosed so as to reduce the side-effects in that individual.

As will be apparent, the compounds of the invention selected from Formula I-XI can be used alone or in combination with other interventions such as beta-blockers, anti-arrhythmic agents, antipsychotics, cannabidiol and antagonists of CB1 (rimonabant) and GABA-benzodiazepines to block or reverse the toxic effects of CB1 SPC agonists As used herein, while no limited to, the CB1 SPC agonists comprise of aminoalkylindoles and cyclohexylphenols such as WIN 55,212-2, CP-55,940; naphtholylindoles can be AM-1221, AM-2201, JWH-018, JWH-122, N-(5-chloropentyl), N-(5-bromopentyl) and N-(5-iodopentyl), JWH-210; tetramethylcyclopropyls such as UR-144, XLR-11, 5F-AKB-48, APICA, STS-135; indole and indozole carboxamides such as AB-CHMINACA, ADB-CHMINACA (MAB-CHMINACA), AB-PINACA, 5F-AB-PINACA, 5F-ADB-PINACA. ADB-FUBICA, 5F-CUMYL-PINACA, AB-FUBINACA, ABD-FUBINACA, 5F-AMB-PINACA, 5F-MDMB-PINACA, MDMB-CHMICA, AMB-CHMINACA, MDMB-CHMINACA, MDMB-FUBICA, MDMB-FUBINACA and 5F-MDMB-PICA.

In another aspect combination therapy, pharmaceutical preparations, and compositions employing the analogs are provided. In yet another aspect, methods of administering therapeutically effective amounts of the analogs to provide a physiological effect are provided.

By "physiologically acceptable salts" is meant, salts typically useful for pharmaceutical applications including acid addition salts and basic salts. Examples of acid addition salts are hydrochloride salts, hydrobromide salts, methane sulfonate salts etc. Examples of basic salts are salts where the cation is selected from alkali metals, such as sodium and potassium, alkaline earth metals, such as calcium, and ammonium ions. Other examples of physiologically acceptable salts can be found in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Polymorphic forms show improved physiochemical properties and stability for formulation purposes. In one embodiment, the compounds disclosed in the invention could exist in various solid forms. The solid forms can be crystalline and amorphous forms, but not limited to, solvates, hydrates, hydrolyzable esters and N-oxides of the compounds defined in the specification. These solid forms can be obtained by treating either the free base or their salts at a certain adjusted pH and certain temperature with a solvent or a combination of solvents. The solvents can be and not limited to a hydrocarbon solvent such as toluene, xylene, hexanes, heptane, or petroleum ether, alcohol such as methanol, ethanol, n-butanol, n-propanol and 2-propanol, di-isopropyl ether, ethyl-acetate, dichloromethane, acetic acid, acetone, tetrahydrofuran, dichloromethane, and water.

In one embodiment, in order to improve or modify the bioavailability, onset and off-set of the compound disclosed in the present invention for the required physiological effect, a "pro-drug" of the same can be made available. For example, the pro-drug such as an in-vivo hydrolyzable ester can be obtained by conjugation of the parent drug with a low-molecular weight alcohol or a high molecular weight polyethylene glycol (PEG). In certain embodiments, the compound disclosed in the invention could contain a nitrate ester group.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

In another embodiment, the compounds of the present disclosure can also comprise isotopes at one or more of their atoms. For example, the compounds can be radiolabeled with isotopes, such as 2H (deuterium written as D). The present disclosure encompasses all isotopic variations of the described compounds, whether natural or unnatural, radioactive or not.

An isotope is one of two or more species of the same element. Each isotope of an element will have the same number of protons in its nucleus, the same atomic number and the same position in the Periodic Table. However, each isotope of that element will have a different number of neutrons in its nucleus and therefore a different mass than other isotopes of that species. The term nuclide is sometimes used synonymously with the term isotope. As used herein a natural isotope has an atomic mass corresponding most closely with the atomic mass shown for that element in the Periodic Table. As used herein an unnatural isotope has an atomic mass that is further removed from the atomic mass shown for that element in the Periodic Table than the natural isotope. For example, protium (hydrogen-1 or 1H) is the natural isotope of hydrogen and deuterium (hydrogen-2 or 2H) is an unnatural isotopes of hydrogen. Several embodiments of the invention are further described in the Specification. It will be recognized that one or more features of any embodiments disclosed herein may be combined and/or rearranged within the scope of the invention to produce further embodiments that are also within the scope of the invention.

In some embodiments, the compounds of Formula I-XI have at least one fluorine atom by replacing any hydrogen atom within.

Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

The disclosure is further illustrated by the following examples, which are not to be construed as limiting this disclosure in scope or spirit to the specific procedures described in this disclosure. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compound Synthesis and Schemes

All reagents and solvents used for chemical synthesis were purchased from Sigma-Aldrich, TCI Chemicals, Fisher Scientific, Acros or Alfa Aesar. The palladium catalysts were purchased from Sigma-Aldrich or TCI Chemicals. 1H NMR (500 MHz) was recorded on a Varian Inova spectrometer. Chemical shifts (δ) are reported in parts per million and are referenced to CDCl3 for 7.26. Multiplicities are indicated as br (broadened), s (singlet), d (doublet), t (triplet) or m (multiplet). Coupling constants (J) are reported in hertz (Hz). Thin layer chromatography (TLC) was performed on Merck-Millipore 210-270 μm TLC silica gel plates, (60 Å) and coated with a F254 fluorescent indicator. Flash column chromatography was performed on a Biotage Isolera Spektra system with UV collections at 254 and 280 nm using Luknova flash columns preloaded with normal phase silica gel (50 μm). All moisture sensitive reactions were performed under an atmosphere of high-purity argon while using oven-dried glassware. The intermediates and final compounds were characterized using a combination of 1H NMR and LC/MS techniques. The LC/MS analysis (11 minute run) was performed as using a Waters MicroMass ZQ system (electrospray ionization mode) equipped with a Waters 2525 binary gradient module, a Waters 2996 photodiode array detector, a Waters 2424 ELS detector, two Waters 515 HPLC pump, a fluidics organizer and a pump control module II. Compounds were analyzed with gradient elution using acetonitrile/water as the mobile phase and an XTerra MS C18 or an XTerra MS C8, 4.6 mm×50 mm column (5 μm). Melting-points were recorded on a Fisher Scientific apparatus.

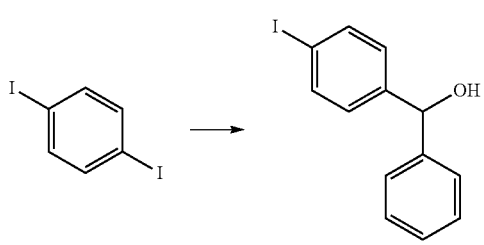 [SMILES: Ic1ccc(I)cc1 ; OC(c1ccccc1)c1ccc(I)cc1]

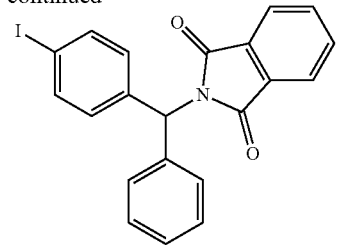

2-((4-Iodophenyl)(Phenyl)Methyl)Isoindoline-1,3-Dione (4-Iodophenyl)(Phenyl)Methanol Isopropylmagnesium chloride (9.8 mL, 19.69 mmol) was added dropwise to a solution of 1,4-diiodobenzene (5.92 g, 17.9 mmol) in tetrahydrofuran (50 mL) at −40° C. and stirred for 30 min. Then a solution of benzaldehyde (2 mL, 19.69 mmol) in tetrahydrofuran (10 mL) was slowly added, stirred for 1 h and quenched with aqueous ammonium chloride (saturated solution 10 mL). The solution was diluted with ethyl acetate (250 mL), washed with water (2×150 mL) and the combined aqueous layers were extracted with ethyl acetate (250 mL). The combined organic layers were washed with brine (300 mL), dried (MgSO$_4$) and concentrated in vacuo. The residue was purified by flash column chromatography (19:1 hexanes:ethyl acetate) to afford the title compound (5.28 g, 95%).

Potassium phthalimide (2.76 g, 14.9 mmol) and 1-(bromo (phenyl)methyl)-4-iodobenzene (5.30 g, 14.2 mmol) were dissolved in dimethylformamide (50 mL) and heated to 120° C. for 20 min and cooled to 25° C. The solid was filtered and the filtrate concentrated in vacuo. The residue was purified by flash column chromatography (19:1 to 1:1 hexanes:ethyl acetate) to afford the title compound (5.24 g, 84%) as a yellow solid.

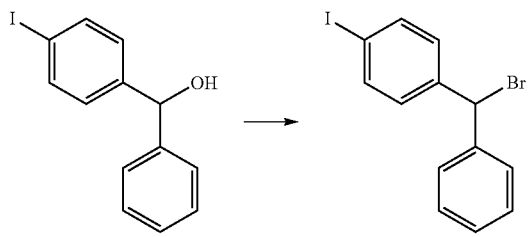 [SMILES: OC(c1ccccc1)c1ccc(I)cc1 ; BrC(c1ccccc1)c1ccc(I)cc1]

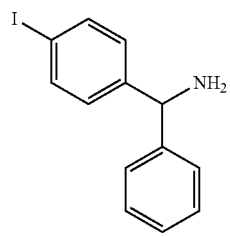

1-(Bromo(Phenyl)Methyl)-4-Iodobenzene

4-Iodophenyl)(Phenyl)Methanamine (4-iodophenyl)(phenyl)methanol (4.54 g, 14.6 mmol) was dissolved in hydrobromic acid (33% in acetic acid) (40 mL) and stirred at 25° C. for 30 min. The solution was diluted with ice water (300 mL), neutralized by the slow addition of solid sodium bicarbonate until pH=~8 and extracted with ethyl acetate (3×200 mL), dried (MgSO$_4$), and concentrated in vacuo to afford the title compound as an orange oil (5.30 g, 97%). The compound, proving to be unstable was used immediately in the next step.

Hydrazine hydrate (1.66 mL, 34.2 mmol) was added to a solution of 2-((4-iodophenyl)(phenyl)methyl) isoindoline-1, 3-dione (5.00 g, 11.4 mmol) in ethanol (100 mL) and refluxed for 3 h. The heterogeneous mixture was cooled to 0° C., filtered and washed with ethyl ether (5×, 200 mL). The filtrate was dried (MgSO$_4$) and condensed in vacuo. The residue was purified by flash column chromatography (1:1 hexanes:ethyl ether) to afford the volatile title compound (2.40 g, 68%) as a light yellow oil

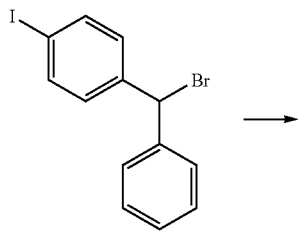

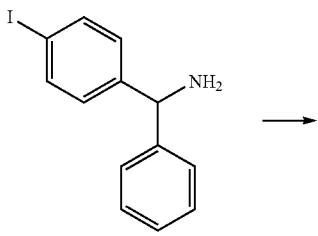

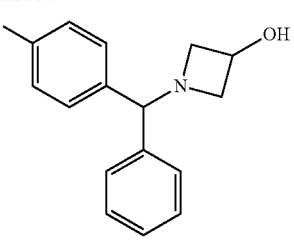

1-((4-Iodophenyl)(Phenyl)Methyl)Azetidin-3-Ol

Epichlorohydrin (0.410 mL, 5.24 mmol) was added to a solution of (4-iodophenyl)(phenyl)methanamine (0.810 g, 2.62 mmol) in isopropyl alcohol (40 mL), stirred at 25° C. for 3 d and concentrated in vacuo. Triethylamine (0.364 mL, 2.62 mmol) was then added to the crude oil dissolved in acetonitrile (30 mL) and refluxed for 48 h, cooled to 25° C. and concentrated in vacuo. The residue was purified by flash column chromatography (19:1 to 19:1 hexanes:ethyl acetate) to afford the title compound (0.612 g, 64%) as a white solid.

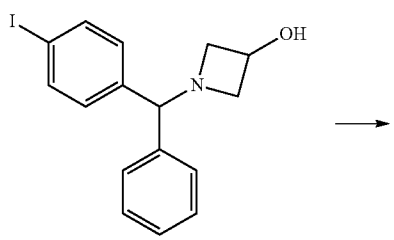

1-((4-Iodophenyl)(Phenyl)Methyl)Azetidin-3-Yl Methanesulfonate

Triethylamine (0.695 mL, 4.98 mmol) and methanesulfonyl chloride (0.388 mL, 4.98 mmol) were added sequentially to a solution of 1-((4-iodophenyl)(phenyl)methyl)azetidin-3-ol (0.608 g, 1.66 mmol) in benzene (15 mL) at 5° C., warmed to 25° C. and stirred for 30 min. The mixture was diluted with dichloromethane (200 mL), washed with water (2×, 100 mL), brine (100 mL), dried (MgSO$_4$) and condensed in vacuo. The residue was purified by filtration through a short pad of silica gel (1:1 ethyl acetate:hexane) to afford the title compound (0.699 g, 95%) as a white solid.

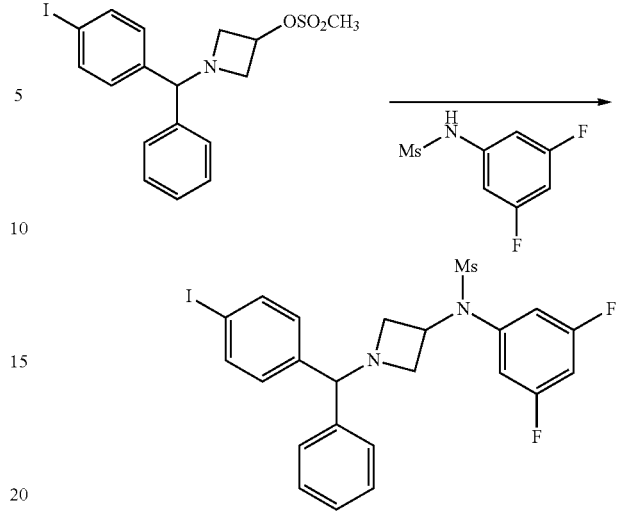

N-(3,5-Difluorophenyl)-N-(1-((4-Iodophenyl)(Phenyl)Methyl)Azetidin-3-Yl)Methanesulfonamide Triethylamine (3.46 mL, 24.84 mmol) was added to a solution of N-(3,5-difluorophenyl)methanesulfonamide (3.43 g, 16.56 mmol) and 1-((4-iodophenyl)(phenyl)methyl) azetidin-3-yl methanesulfonate (3.67 g, 8.28 mmol) in methanol (60 mL) and heated to 45° C. for 48 h. The solution was diluted with ethyl acetate (200 mL), washed with water (2×100 mL) and the combined aqueous layers were extracted with ethyl acetate (200 mL). The combined organic layers were washed with brine (150 mL), dried (MgSO$_4$) and concentrated in vacuo. The residue was purified by flash column chromatography (gradient 9:1 to 7:3 hexanes:ethyl acetate, pre-neutralized 19:1 hexanes:triethylamine) to afford the title compound (2.59 g, 53%) as a white solid.

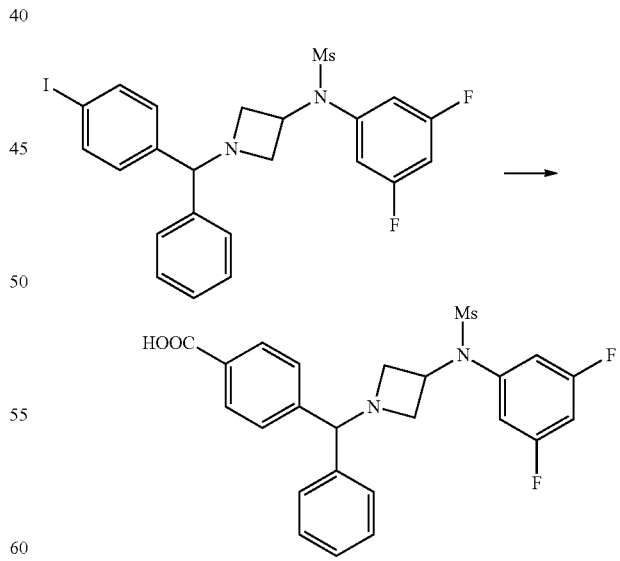

4-((3-(N-(3,5-Difluorophenyl)Methylsulfonamido) Azetidin-1-Yl)(Phenyl)Methyl)Benzoic Acid A 35 mL sealed tube equipped with a stir bar was charged with oxalic acid dihydrate (1.5 equiv), palladium (II) acetate (1 mol %), triphenylphosphine (3 mol %), N-(3,5-difluorophenyl)-N-(1-((4-iodophenyl)(phenyl)methyl)azetidin-3-yl)methanesulfonamide, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO₄, filtered and the filtrate was passed through a short bed of silica gel, and the organic layer was concentrated, and the residue was taken directly to the next step (70%).

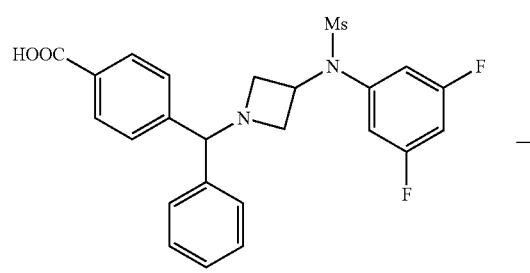

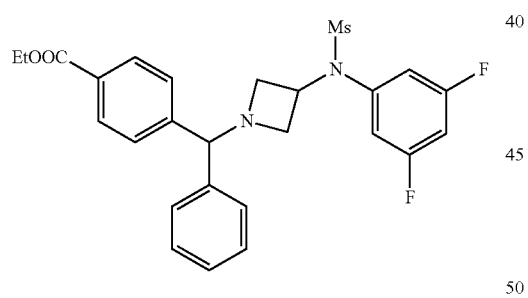

Ethyl 4-((3-(N-(3,5-Difluorophenyl)Methylsulfonamido)Azetidin-1-Yl)(Phenyl)Methyl)Benzoate 4-((3-(N-(3,5-difluorophenyl)methylsulfonamido)azetidin-1-yl)(phenyl)methyl)benzoic acid (1.5 g) obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2x~10 mL). The contents were brought to pH 6-7 and the organic layer was separated, dried over anhydrous MgSO₄, filtered and the solvent was evaporated in vacuo to provide the ester as an off-white solid (87%).

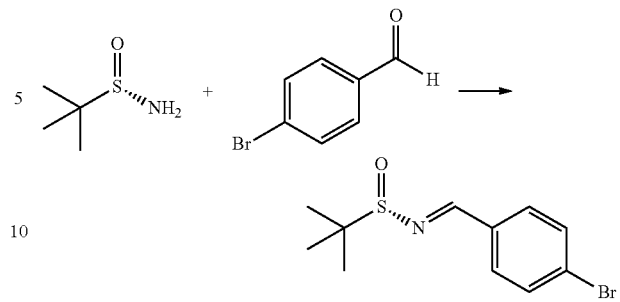

(S,E)-N-(4-Bromobenzylidene)-2-Methylpropane-2-Sulfinamide

Tetraethoxy titanium (0.860 mL, 4.14 mmol) was added to a solution of (S)-2-methylpropane-2-sulfinamide (0.251 g, 2.07 mmol) and 4-bromobenzaldehyde (0.386 g, 2.07 mmol) in tetrahydrofuran (8 mL) at 25° C. The mixture was heated to 45° C. for 5 h and quenched with saturated ammonium chloride (5 mL), filtered through a pad of celite and washed with ethyl acetate (100 mL). The filtrate was diluted with water (50 mL) and the layers separated. The aqueous layers were extracted with ethyl acetate (2×50 mL) and the combined organic layers washed with brine (100 mL), dried (MgSO₄), and concentrated in vacuo. The residue was purified by flash column chromatography (19:1 to 9:1 hexanes:ethyl acetate) to afford the title compound (0.450 g, 75%) as a white solid

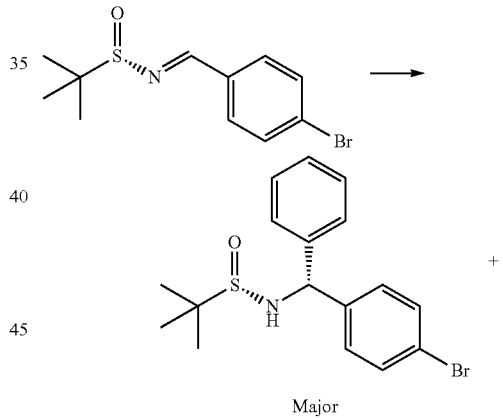

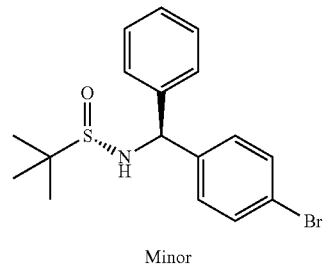

(S)—N—((R)-(4-Bromophenyl)(Phenyl)Methyl)-2-Methylpropane-2-Sulfinamide: (Major) 5.38 and
(S)—N—((S)-(4-Bromophenyl)(Phenyl)Methyl)-2-Methylpropane-2-Sulfinamide: (Minor Phenylmagnesium bromide 3M in ethyl ether (1.52 mL, 1.52 mmol) was added dropwise to a solution of (S,E)-N-

(4-bromobenzylidene)-2-methylpropane-2-sulfinamide (0.293 g, 1.01 mmol) in tetrahydrofuran (10 mL) at −40° C. and slowly warmed to 25° C. over 3 h. The reaction mixture was quenched with saturated ammonium chloride (5 mL) and filtered through a pad of celite and washed with ethyl acetate (100 mL). The filtrate was diluted with water (50 mL) and the layers separated. The aqueous layers were extracted with ethyl acetate (2×50 mL) and the combined organic layers washed with brine (100 mL), dried (MgSO₄), and concentrated in vacuo. The residue was purified by flash column chromatography to afford the major product (0.288 g, 77%) and the minor product (0.048 g, 13%), as a colorless oil.

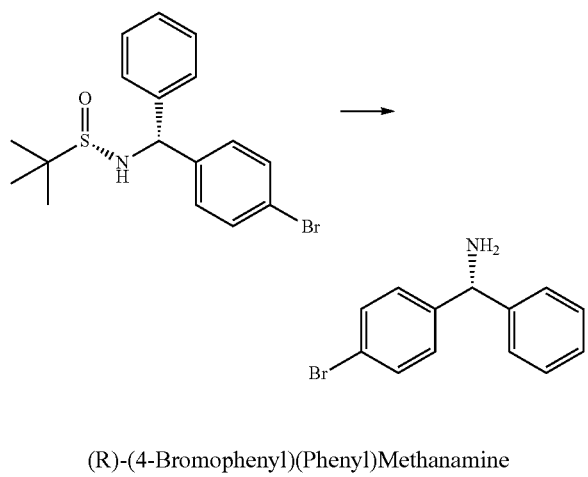

(R)-(4-Bromophenyl)(Phenyl)Methanamine (S)—N—((R)-(4-bromophenyl)(phenyl)methyl)-2-methylpropane-2-sulfinamide (0.170 g, 0.463 mmol) was dissolved in 4M hydrochloric acid in 1,2-dioxane (5 mL) and methanol (5 mL) at 25° C., stirred for 30 min. and concentrated in vacuo. The residue was washed with ethyl ether (100 mL), dissolved in saturated sodium bicarbonate (20 mL), extracted with ethyl ether (4×50 mL), dried (MgSO₄) and concentrated in vacuo to afford the title compound (0.120 g, 98%) as a yellow oil.

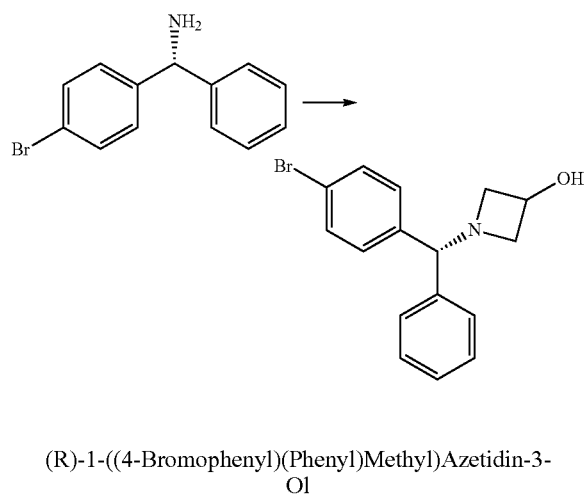

(R)-1-((4-Bromophenyl)(Phenyl)Methyl)Azetidin-3-Ol

Epichlorohydrin (0.060 mL, 0.798 mmol) was added to a solution of (R)-(4-bromophenyl)(phenyl)methanamine (0.105 g, 0.399 mmol) in isopropyl alcohol (8 mL) at 0° C. The solution was warmed to 25° C., stirred for 3 d and concentrated in vacuo. Triethylamine (0.111 mL, 0.798 mmol) was then added to the crude oil dissolved in acetonitrile (8 mL) and refluxed for 72 h, cooled to 25° C. and concentrated in vacuo. The residue was purified by flash column chromatography (9:1 hexanes:ethyl acetate) to afford the title compound (0.08 g, 63%) as a yellow oil.

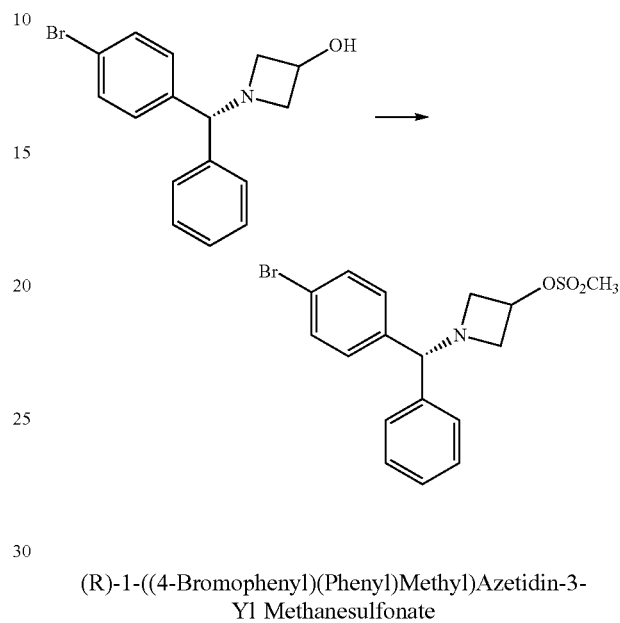

(R)-1-((4-Bromophenyl)(Phenyl)Methyl)Azetidin-3-Yl Methanesulfonate

Triethylamine (0.100 mL, 0.714 mmol) and methanesulfonyl chloride (0.056 mL, 0.714 mmol) were added sequentially to a solution of (R)-1-((4-bromophenyl)(phenyl)methyl)azetidin-3-ol (0.076 g, 0.238 mmol) in benzene (3 mL) at 5° C., warmed to 25° C. and stirred for 30 min. The mixture was diluted with dichloromethane (40 mL), washed with water (2×, 50 mL), brine (50 mL), dried (MgSO₄) and condensed in vacuo. The residue was purified by filtration through a short pad of silica gel (1:1 ethyl acetate:hexane) to afford the title compound (0.093 g, 98%) as a light yellow oil.

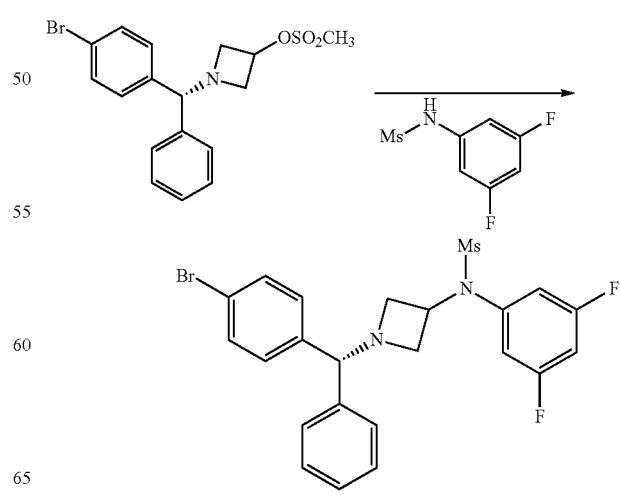

(R)—N-(1-((4-Bromophenyl)(Phenyl)Methyl)Azetidin-3-Yl)-N-(3,5-Difluorophenyl)Methanesulfonamide Triethylamine (0.051 mL, 0.370 mmol) was added to a solution of 3,5-difluoro-N-methylaniline (0.032 g, 0.154 mmol) and (R)-1-((4-bromophenyl)(phenyl)methyl)azetidin-3-yl methanesulfonate (0.049 g, 0.123 mmol) in methanol (1.5 mL) heated to 45° C. for 48 h and concentrated in vacuo. The residue was purified by flash column chromatography (18:1:1 to 8:1:1 hexanes:ethyl acetate:triethylamine) to afford the title compound (0.024 g, 38%) as a white solid.

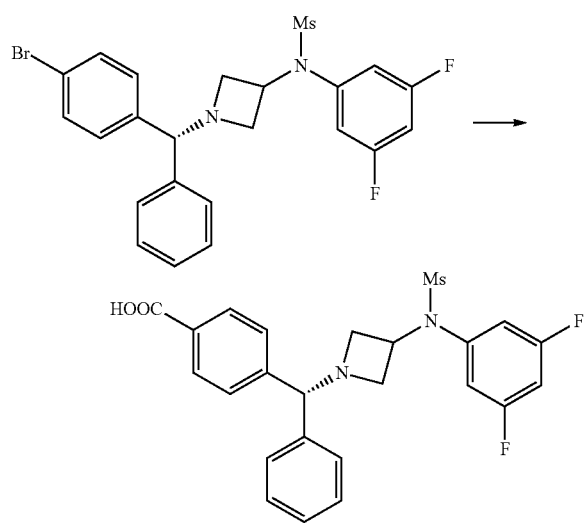

(R)-4-((3-(N-(3,5-Difluorophenyl)Methylsulfonamido)Azetidin-1-Yl)(Phenyl)Methyl)Benzoic Acid A 35 mL sealed tube equipped with a stir bar was charged with oxalic acid dihydrate (1.5 equiv), palladium (II) acetate (1 mol %), xantphos (1 mol %), (R)—N-(1-((4-bromophenyl)(phenyl)methyl)azetidin-3-yl)-N-(3,5-difluorophenyl) methanesulfonamide, acetic anhydride (1.5 equiv), N,N-diisopropylethylamine (1.5 equiv), N,N-dimethylformamide under air. The tube was quickly sealed with a Teflon® high pressure valve, frozen in liquid nitrogen, evacuated and backfilled with $N_2$ (5 times). After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over $MgSO_4$, filtered and the filtrate was passed through a short bed of silica gel, and the organic layer was concentrated, and the residue was taken directly to the next step (70%).

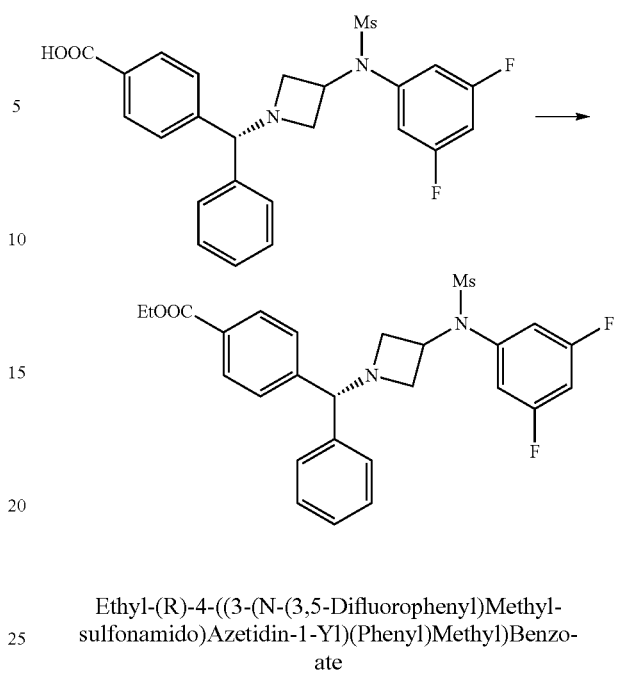

Ethyl-(R)-4-((3-(N-(3,5-Difluorophenyl)Methylsulfonamido)Azetidin-1-Yl)(Phenyl)Methyl)Benzoate (R)-4-((3-(N-(3,5-difluorophenyl)methylsulfonamido)azetidin-1-yl)(phenyl)methyl)benzoic acid (20 mg) obtained from the previous step was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~10 mL). The contents were brought to pH 6-7 and the organic layer was separated, dried over anhydrous $MgSO_4$, filtered and the solvent was evaporated in vacuo to provide the ester as an off-white solid (87%).

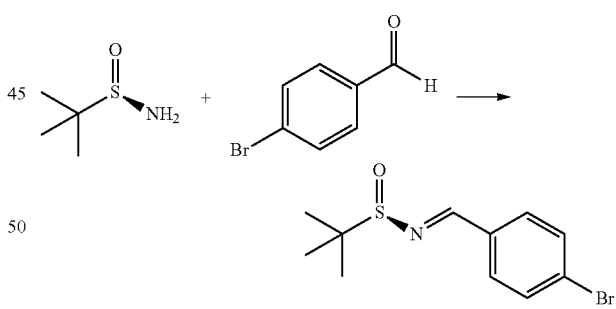

(R,E)-N-(4-Bromobenzylidene)-2-Methylpropane-2-Sulfinamide

Tetraethoxy titanium (0.860 mL, 4.14 mmol) was added to a solution of (R)-2-methylpropane-2-sulfinamide (0.251 g, 2.07 mmol) and 4-bromobenzaldehyde (0.386 g, 2.07 mmol) in tetrahydrofuran (8 mL) at 25° C. The mixture was heated to 45° C. for 5 h and quenched with saturated ammonium chloride (5 mL), filtered through a pad of celite and washed with ethyl acetate (100 mL). The filtrate was diluted with water (50 mL) and the layers separated. The aqueous layers were extracted with ethyl acetate (2×50 mL)

and the combined organic layers washed with brine (100 mL), dried (MgSO₄), and concentrated in vacuo. The residue was purified by flash column chromatography (19:1 to 9:1 hexanes:ethyl acetate) to afford the title compound (0.450 g, 75%) as a white solid.

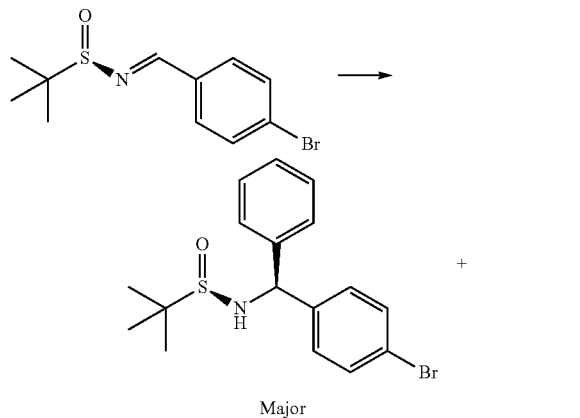

Major

Minor (R)—N—((S)-(4-bromophenyl)(phenyl)methyl)-2-methylpropane-2-sulfinamide: (Major) 5.38 and (R)—N—((R)-(4-bromophenyl)(phenyl)methyl)-2-methylpropane-2-sulfinamide: (Minor Phenylmagnesium bromide 3M in ethyl ether (1.52 mL, 1.52 mmol) was added dropwise to a solution of (R,E)-N-(4-bromobenzylidene)-2-methylpropane-2-sulfinamide (0.293 g, 1.01 mmol) in tetrahydrofuran (10 mL) at −40° C. and slowly warmed to 25° C. over 3 h. The reaction mixture was quenched with saturated ammonium chloride (5 mL) and filtered through a pad of celite and washed with ethyl acetate (100 mL). The filtrate was diluted with water (50 mL) and the layers separated. The aqueous layers were extracted with ethyl acetate (2×50 mL) and the combined organic layers washed with brine (100 mL), dried (MgSO₄), and concentrated in vacuo. The residue was purified by flash column chromatography to afford the major product (0.288 g, 77%) and the minor product (0.048 g, 13%), as a colorless oil.

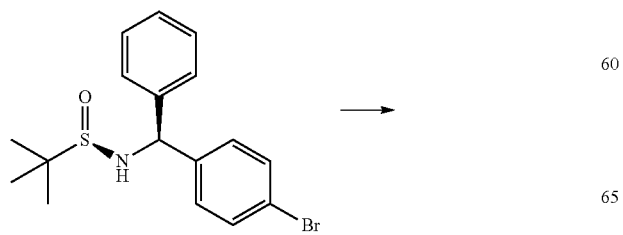

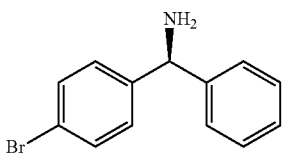

(S)-(4-Bromophenyl)(Phenyl)Methanamine (R)—N—((S)-(4-Bromophenyl)(Phenyl)Methyl)-2-Methylpropane-2-Sulfinamide (0.170 g, 0.463 mmol) was dissolved in 4M hydrochloric acid in 1,2-dioxane (5 mL) and methanol (5 mL) at 25° C., stirred for 30 min. and concentrated in vacuo. The residue was washed with ethyl ether (100 mL), dissolved in saturated sodium bicarbonate (20 mL), extracted with ethyl ether (4×50 mL), dried (MgSO₄) and concentrated in vacuo to afford the title compound (0.120 g, 98%) as a yellow oil.

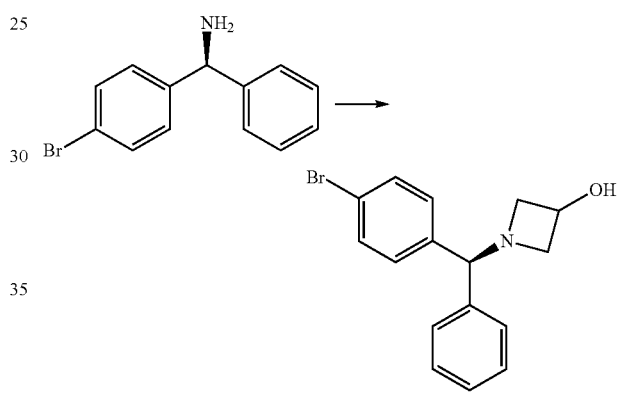

(S)-1-((4-Bromophenyl)(Phenyl)Methyl)Azetidin-3-Ol

Epichlorohydrin (0.060 mL, 0.798 mmol) was added to a solution of (S)-(4-bromophenyl)(phenyl)methanamine (0.105 g, 0.399 mmol) in isopropyl alcohol (8 mL) at 0° C. The solution was warmed to 25° C., stirred for 3 d and concentrated in vacuo. Triethylamine (0.111 mL, 0.798 mmol) was then added to the crude oil dissolved in acetonitrile (8 mL) and refluxed for 72 h, cooled to 25° C. and concentrated in vacuo. The residue was purified by flash column chromatography (9:1 hexanes:ethyl acetate) to afford the title compound (0.08 g, 63%) as a yellow oil.

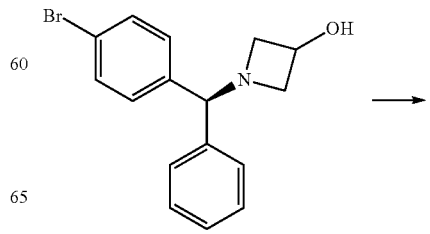

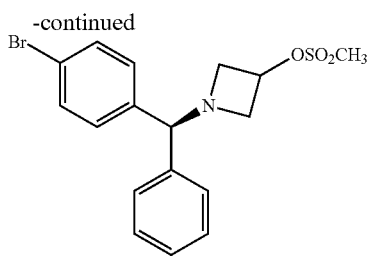

(S)-1-((4-Bromophenyl)(Phenyl)Methyl)Azetidin-3-Yl Methanesulfonate

Triethylamine (0.100 mL, 0.714 mmol) and methanesulfonyl chloride (0.056 mL, 0.714 mmol) were added sequentially to a solution of (S)-1-((4-bromophenyl)(phenyl)methyl)azetidin-3-ol (0.076 g, 0.238 mmol) in benzene (3 mL) at 5° C., warmed to 25° C. and stirred for 30 min. The mixture was diluted with dichloromethane (40 mL), washed with water (2×, 50 mL), brine (50 mL), dried (MgSO$_4$) and condensed in vacuo. The residue was purified by filtration through a short pad of silica gel (1:1 ethyl acetate:hexane) to afford the title compound (0.093 g, 98%) as a light yellow oil.

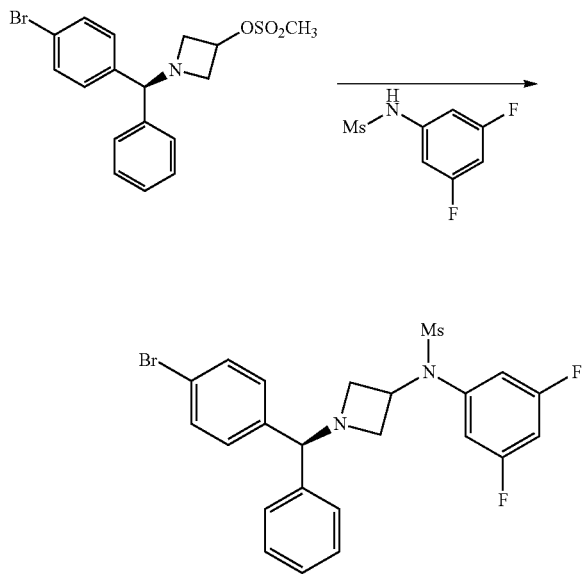

(S)—N-(1-((4-Bromophenyl)(Phenyl)Methyl)Azetidin-3-Yl)-N-(3,5-Difluorophenyl)Methanesulfonamide Triethylamine (0.051 mL, 0.370 mmol) was added to a solution of 3,5-difluoro-N-methylaniline (0.032 g, 0.154 mmol) and (S)-1-((4-bromophenyl)(phenyl)methyl)azetidin-3-yl methanesulfonate (0.049 g, 0.123 mmol) in methanol (1.5 mL) heated to 45° C. for 48 h and concentrated in vacuo. The residue was purified by flash column chromatography (18:1:1 to 8:1:1 hexanes:ethyl acetate:triethylamine) to afford the title compound (0.024 g, 38%) as a white solid.

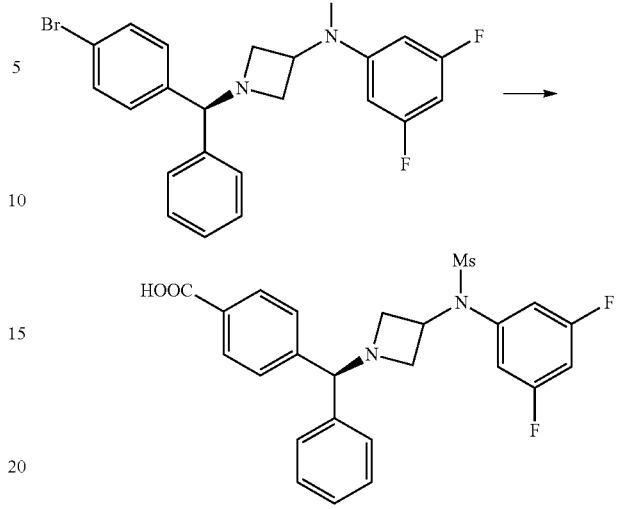

(S)-4-((3-(N-(3,5-Difluorophenyl)Methylsulfonamido)Azetidin-1-Yl)(Phenyl)Methyl)Benzoic Acid A 35 mL sealed tube equipped with a stir bar was charged with oxalic acid dihydrate (1.5 equiv), palladium (II) acetate (1 mol %), xantphos (1 mol %), (S)—N-(1-((4-bromophenyl)(phenyl)methyl)azetidin-3-yl)-N-(3,5-difluorophenyl) methanesulfonamide, acetic anhydride (1.5 equiv), N,N-diisopropylethylamine (1.5 equiv), N,N-dimethylformamide under air. The tube was quickly sealed with a Teflon® high pressure valve, frozen in liquid nitrogen, evacuated and backfilled with N$_2$ (5 times). After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO$_4$, filtered and the filtrate was passed through a short bed of silica gel, and the organic layer was concentrated and the residue was taken directly to the next step (70%).

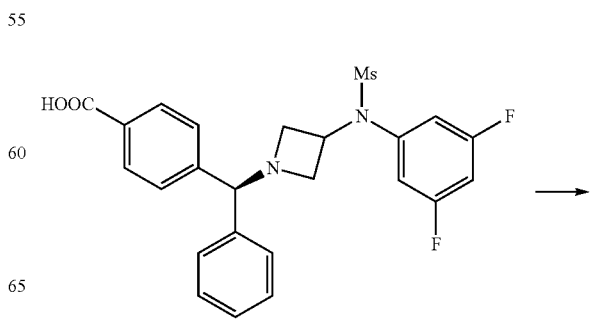

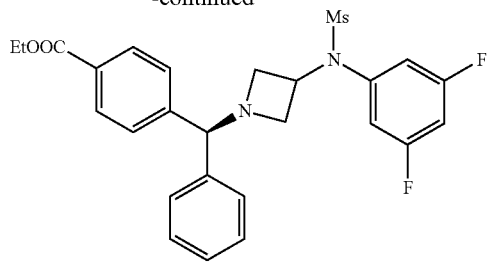

Ethyl-(S)-4-((3-(N-(3,5-Difluorophenyl)Methyl-sulfonamido)Azetidin-1-Yl)(Phenyl)Methyl)Benzoate (S)-4-((3-(N-(3,5-Difluorophenyl)methylsulfonamido)azetidin-1-yl)(phenyl)methyl)benzoic acid (20 mg) obtained from the previous step was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~10 mL). The organic layer was separated, dried over anhydrous MgSO$_4$, filtered and the solvent was evaporated in vacuo to provide the ester as an off-white solid (87%)

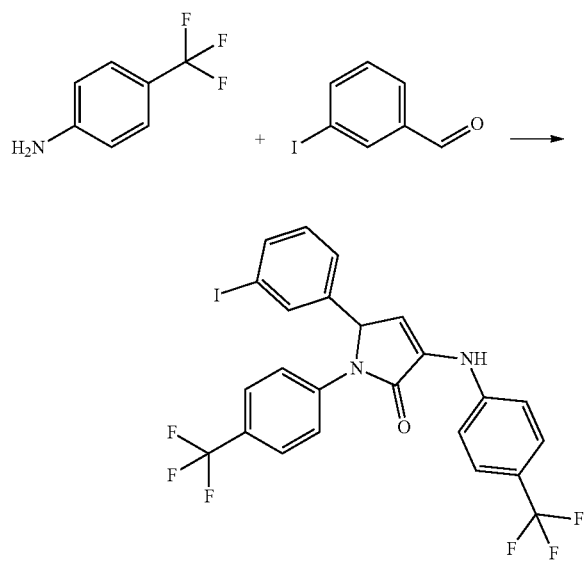 [SMILES: Nc1ccc(C(F)(F)F)cc1 ; O=Cc1cccc(I)c1 ; O=C1C(Nc2ccc(C(F)(F)F)cc2)=CC(c2cccc(I)c2)N1c1ccc(C(F)(F)F)cc1]

5-(3-Iodophenyl)-1-(4-(Trifluoromethyl)Phenyl)-3-((4-(Trifluoromethyl)Phenyl)Amino)-1,5-Dihydro-2H-Pyrrol-2-One 4-Aminobenzotrifluoride (270.7 mmol) was added to a solution of 3-iodobenzaldehyde (90.2 mmol) in glacial acetic acid (80 mL). Ethyl pyruvate (90.2 mmol) was added and the mixture stirred at ambient temperature for 18 h. The precipitate was filtered and washed with a mixture of 20% MTBE in heptane and dried under vacuum to afford the title compound (85%)

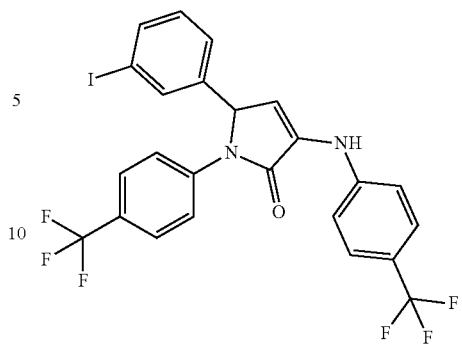

5-(3-Iodophenyl)-1-(4-(Trifluoromethyl)Phenyl) Pyrrolidine-2,3-Dione

A slurry of 5-(3-iodophenyl)-1-(4-(trifluoromethyl)phenyl)-3-((4-(trifluoromethyl)phenyl)amino)-1,5-dihydro-2H-pyrrol-2-one (182 mmol), glacial acetic acid (400 mL) and concentrated HCl. (500 mL) was stirred at ambient temperature for 22 h. The heterogeneous mixture was heated to 60 deg C. for 1 h. The mixture was poured onto ice (1 L), was stirred, and stood for 1 h. The precipitate was filtered, washed with water, and dried under vacuum to afford a solid. The solid still contained starting material. The solid was slurried with glacial acetic acid (500 mL) and concentrated HCl. (500 mL) and stirred at ambient temperature for 22 h. The mixture was poured onto ice and water (2 L), was stirred, and stood for 1 h. The solid was filtered, washed with water, and dried under vacuum to afford the title compound (80%). 1H NMR showed the material to be a mixture of enol-keto tautomers.

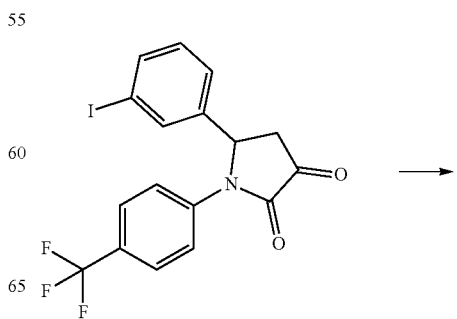

-continued

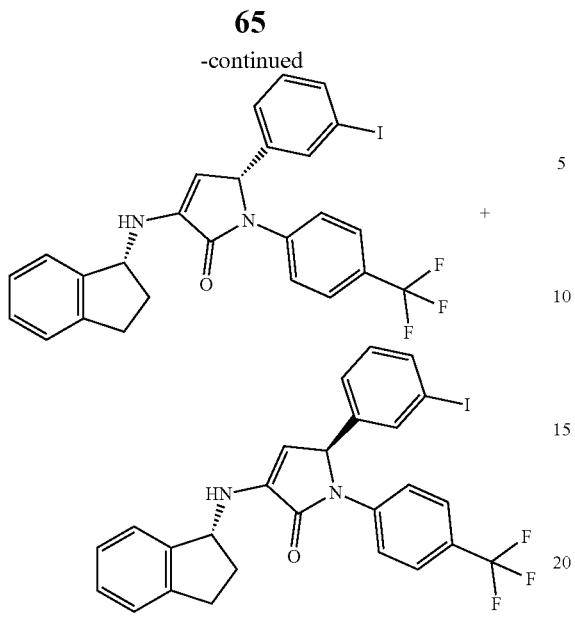

(R)-3-(((R)-2,3-Dihydro-1H-Inden-1-Yl)Amino)-5-(3-Iodophenyl)-1-(4-(Trifluoromethyl)Phenyl)-1,5-Dihydro-2H-Pyrrol-2-One and (S)-3-(((R)-2,3-Dihydro-1H-Inden-1-Yl)Amino)-5-(3-Iodophenyl)-1-(4-(Trifluoromethyl)Phenyl)-1,5-Dihydro-2H-Pyrrol-2-One (R)-1-Aminoindane (176 mmol) was added to a solution of 5-(3-Iodophenyl)-1-(4-(trifluoromethyl)phenyl)pyrrolidine-2,3-dione (88.2 mmol) in CH$_2$Cl2 (225 mL). The solution was stirred at ambient temperature for 18 h. The solution was then poured onto a silica gel column, and the CH$_2$Cl2 was evaporated off with a stream of nitrogen. The material was purified by silica gel chromatography (5-15% EtOAc/hexanes) to afford a mixture of diastereomers, the first eluting isomer, as a white foam (24%) and a the second eluting isomer, as a yellow foam (17%).

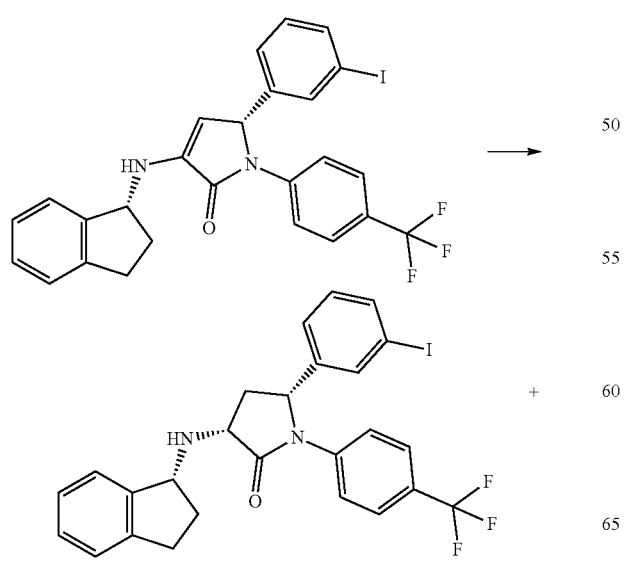

-continued

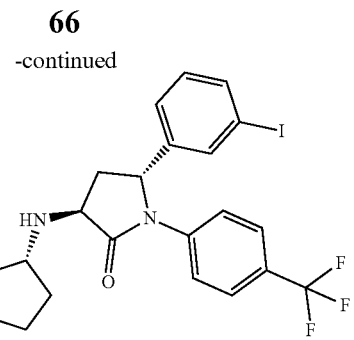

(3R,5R)-3-(((R)-2,3-Dihydro-1H-Inden-1-Yl)Amino)-5-(3-Iodophenyl)-1-(4-(Trifluoromethyl)Phenyl)Pyrrolidin-2-One and (3S,5R)-3-(((R)-2,3-Dihydro-1H-Inden-1-Yl)Amino)-5-(3-Iodophenyl)-1-(4-(Trifluoromethyl)Phenyl)Pyrrolidin-2-One Sodium cyanoborohydride (12.4 mmol) was added to a solution of (R)-3-(((R)-2,3-dihydro-1H-inden-1-yl)amino)-5-(3-iodophenyl)-1-(4-(trifluoromethyl)phenyl)-1,5-dihydro-2H-pyrrol-2-one (6.19 mmol) in glacial acetic acid (31 mL). The reaction mixture was stirred at ambient temperature for 1 h and concentrated in vacuo. The residue was dissolved in EtOAc and washed with a saturated NaHCO3 solution, water, and brine, dried (Na2SO$_4$), and concentrated in vacuo. The material was purified by silica gel chromatography (10-30% EtOAc/hexanes) to afford a first eluting isomer, as a white solid (80%) and a second eluting isomer, as a clear colorless oil (4.3%).

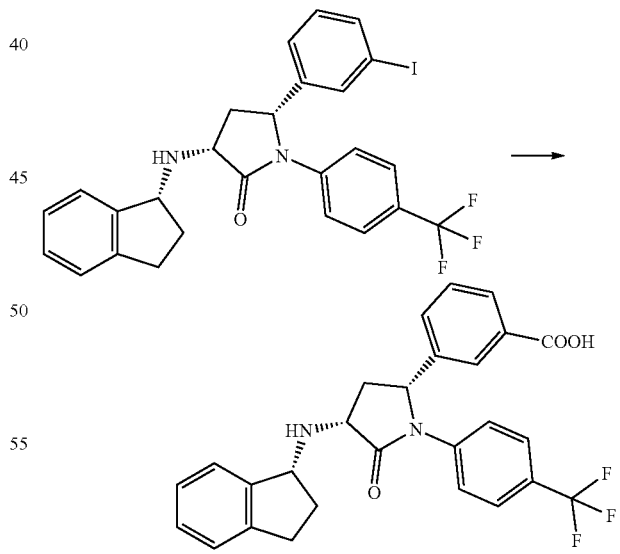

3-((2R,4R)-4-(((R)-2,3-Dihydro-1H-Inden-1-Yl)Amino)-5-Oxo-1-(4-(Trifluoromethyl)Phenyl)Pyrrolidin-2-Yl)Benzoic Acid A 35 mL sealed tube equipped with a stir bar was charged with oxalic acid dihydrate (1.5 equiv), palladium (II) acetate (1 mol %), triphenylphosphine (3 mol %), (3R,5R)-3-(((R)-2,3-dihydro-1H-inden-1-yl)amino)-5-(3-iodophenyl)-1-(4-(trifluoromethyl)phenyl)pyrrolidin-2-one, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO$_4$, filtered and the filtrate was passed through a short bed of silica gel, and the organic layer was concentrated, and the residue was taken directly to the next step (70%).

Ethyl 3-((2R,4R)-4-(((R)-2,3-Dihydro-1H-Inden-1-Yl)Amino)-5-Oxo-1-(4-(Trifluoromethyl)Phenyl)Pyrrolidin-2-Yl)Benzoate 3-((2R,4R)-4-(((R)-2,3-Dihydro-1H-inden-1-yl)amino)-5-oxo-1-(4-(trifluoromethyl)phenyl)pyrrolidin-2-yl)benzoic acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The organic layer was separated, dried over anhydrous MgSO$_4$, filtered and the solvent was evaporated in vacuo to provide the ester as an off-white solid (87%).

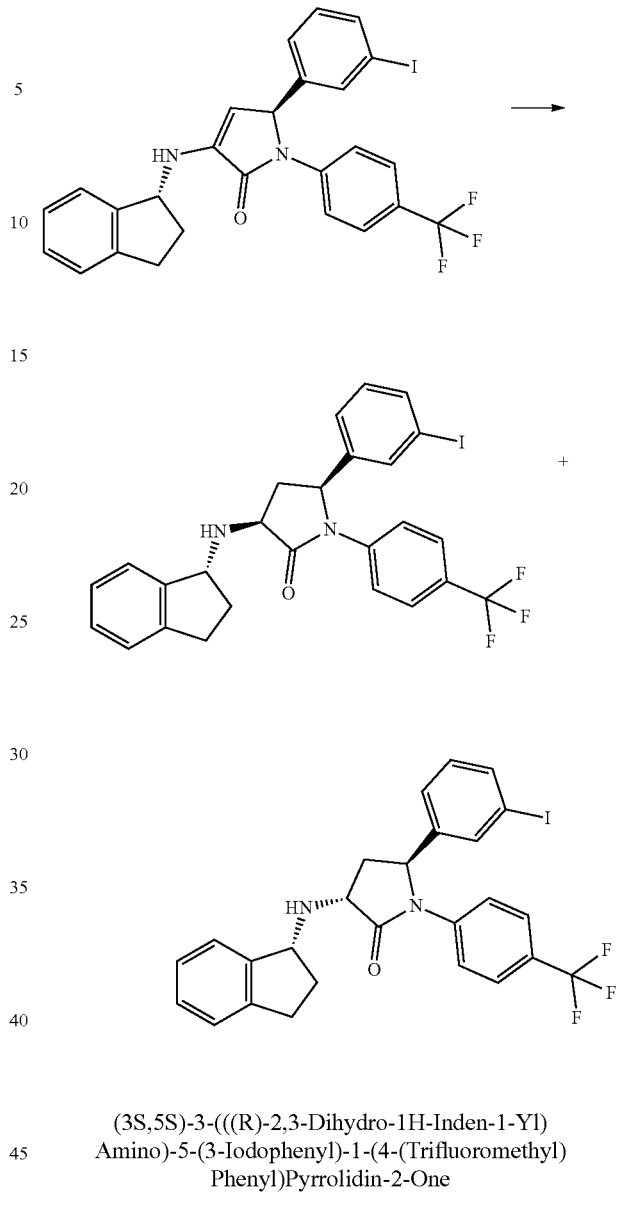

(3S,5S)-3-(((R)-2,3-Dihydro-1H-Inden-1-Yl)Amino)-5-(3-Iodophenyl)-1-(4-(Trifluoromethyl)Phenyl)Pyrrolidin-2-One and (3R,5S)-3-(((R)-2,3-Dihydro-1H-Inden-1-Yl)Amino)-5-(3-Iodophenyl)-1-(4-(Trifluoromethyl)Phenyl)Pyrrolidin-2-One Sodium cyanoborohydride (12.4 mmol) was added to a solution of (S)-3-(((R)-2,3-dihydro-1H-inden-1-yl)amino)-5-(3-iodophenyl)-1-(4-(trifluoromethyl)phenyl)-1,5-dihydro-2H-pyrrol-2-one (6.19 mmol) in glacial acetic acid (31 mL). The reaction mixture was stirred at ambient temperature for 1 h and concentrated in vacuo. The residue was dissolved in EtOAc and washed with a saturated NaHCO3 solution, water, and brine, dried (Na2SO$_4$), and concentrated in vacuo. The material was purified by silica gel chromatography (10-30% EtOAc/hexanes) to afford a first eluting isomer, as a white solid (2.26 g, 80%) and a second eluting isomer, as a clear colorless oil (4.3%).

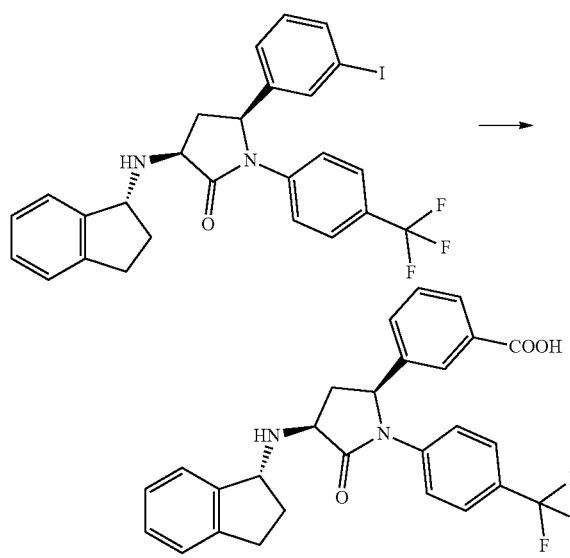

3-((2S,4S)-4-(((R)-2,3-Dihydro-1H-Inden-1-Yl)Amino)-5-Oxo-1-(4-(Trifluoromethyl)Phenyl)Pyrrolidin-2-Yl)Benzoic Acid A 35 mL sealed tube equipped with a stir bar was charged with oxalic acid dihydrate (1.5 equiv), palladium (II) acetate (1 mol %), triphenylphosphine (3 mol %), (3S,5S)-3-(((R)-2,3-dihydro-1H-inden-1-yl)amino)-5-(3-iodophenyl)-1-(4-(trifluoromethyl)phenyl)pyrrolidin-2-one, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO$_4$, filtered and the filtrate was passed through a short bed of silica gel, and the organic layer was concentrated, and the residue was taken directly to the next step (70%).

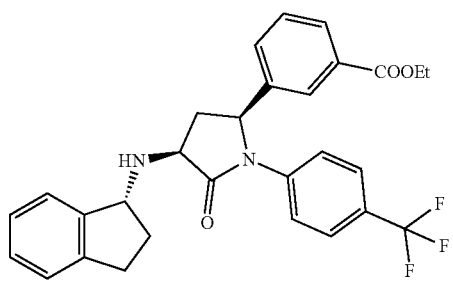

Ethyl 3-((2S,4S)-4-(((R)-2,3-Dihydro-1H-Inden-1-Yl)Amino)-5-Oxo-1-(4-(Trifluoromethyl)Phenyl)Pyrrolidin-2-Yl)Benzoate 3-((2S,4S)-4-(((R)-2,3-Dihydro-1H-inden-1-yl)amino)-5-oxo-1-(4-(trifluoromethyl)phenyl)pyrrolidin-2-yl)benzoic acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The organic layer was separated, dried over anhydrous MgSO$_4$, filtered and the solvent was evaporated in vacuo to provide the ester as an off-white solid (87%).

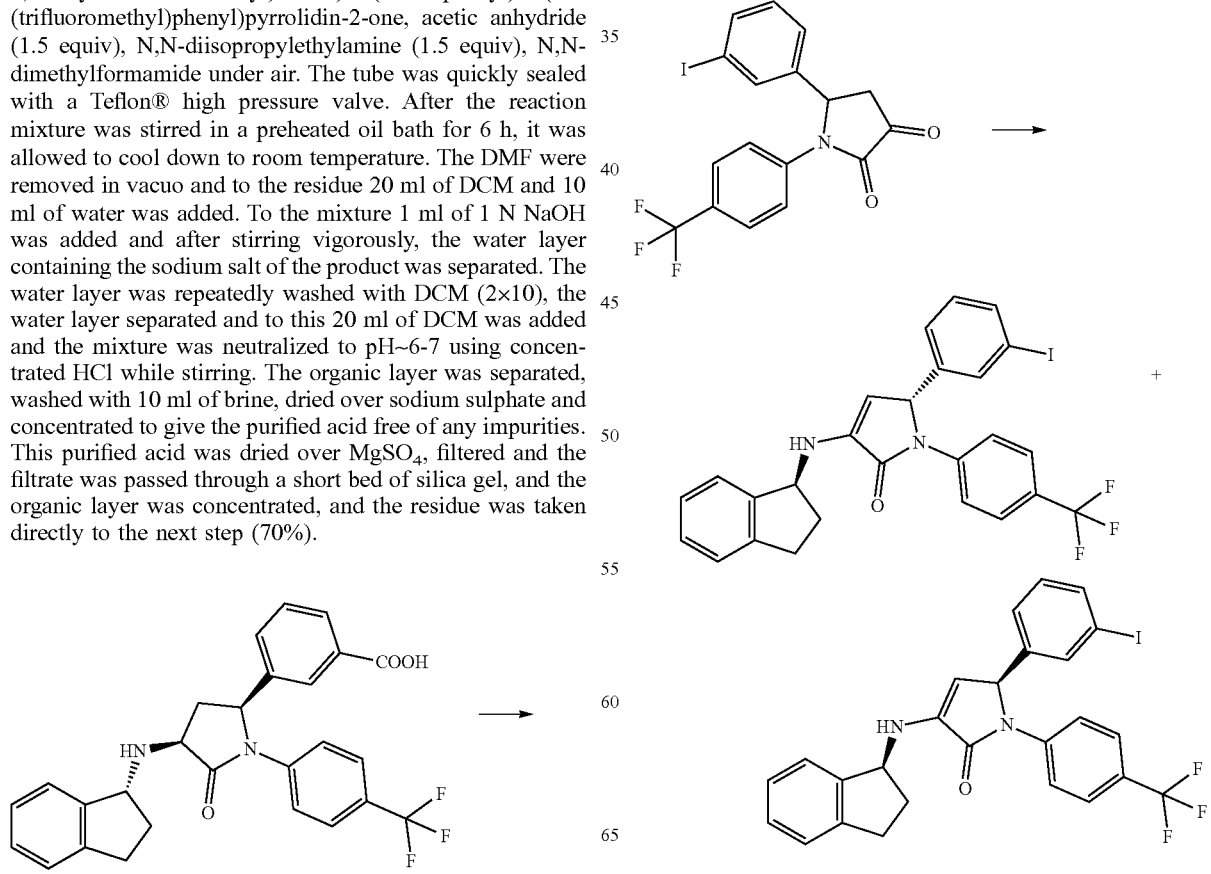

(R)-3-(((S)-2,3-Dihydro-1H-Inden-1-Yl)Amino)-5-(3-Iodophenyl)-1-(4-(Trifluoromethyl)Phenyl)-1,5-Dihydro-2H-Pyrrol-2-One and (S)-3-(((S)-2,3-Dihydro-1H-Inden-1-Yl)Amino)-5-(3-Iodophenyl)-1-(4-(Trifluoromethyl)Phenyl)-1,5-Dihydro-2H-Pyrrol-2-One (S)-1-Aminoindane (176 mmol) was added to a solution of 5-(3-iodophenyl)-1-(4-(trifluoromethyl)phenyl)pyrrolidine-2,3-dione (88.2 mmol) in CH$_2$Cl2 (225 mL). The solution was stirred at ambient temperature for 18 h. The solution was then poured onto a silica gel column, and the CH$_2$Cl2 was evaporated off with a stream of nitrogen. The material was purified by silica gel chromatography (5-15% EtOAc/hexanes) to afford a mixture of diastereomers, the first eluting isomer, as a white foam (9.6 g, 24%) and a the second eluting isomer, as a yellow foam (17%).

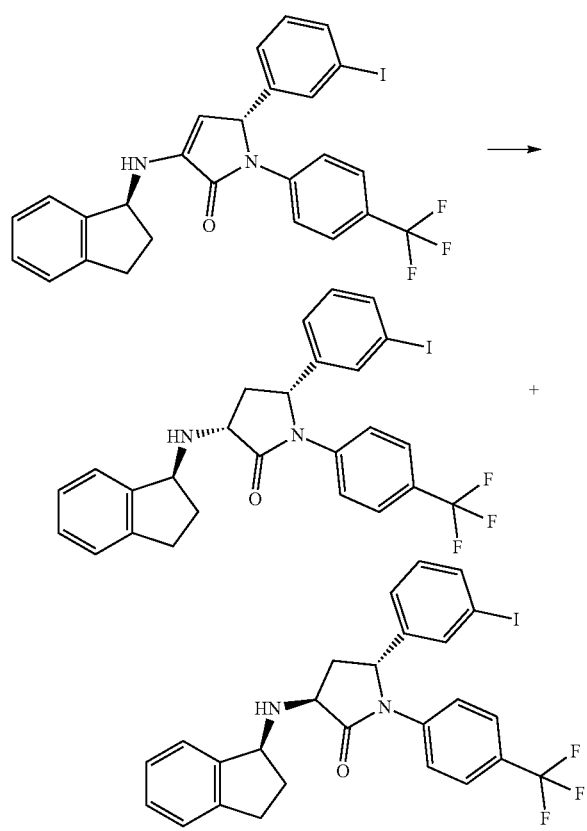

(3R,5R)-3-(((S)-2,3-Dihydro-1H-Inden-1-Yl)Amino)-5-(3-Iodophenyl)-1-(4-(Trifluoromethyl)Phenyl)Pyrrolidin-2-One and (3S,5R)-3-(((S)-2,3-Dihydro-1H-Inden-1-Yl)Amino)-5-(3-Iodophenyl)-1-(4-(Trifluoromethyl)Phenyl)Pyrrolidin-2-One Sodium cyanoborohydride (12.4 mmol) was added to a solution of (R)-3-(((S)-2,3-dihydro-1H-inden-1-yl)amino)-5-(3-iodophenyl)-1-(4-(trifluoromethyl)phenyl)-1,5-dihydro-2H-pyrrol-2-one (6.19 mmol) in glacial acetic acid (31 mL). The reaction mixture was stirred at ambient temperature for 1 h and concentrated in vacuo. The residue was dissolved in EtOAc and washed with a saturated NaHCO3 solution, water, and brine, dried (Na2SO$_4$), and concentrated in vacuo. The material was purified by silica gel chromatography (10-30% EtOAc/hexanes) to afford a first eluting isomer, as a white solid (80%) and a second eluting isomer, as a clear colorless oil (4.3%).

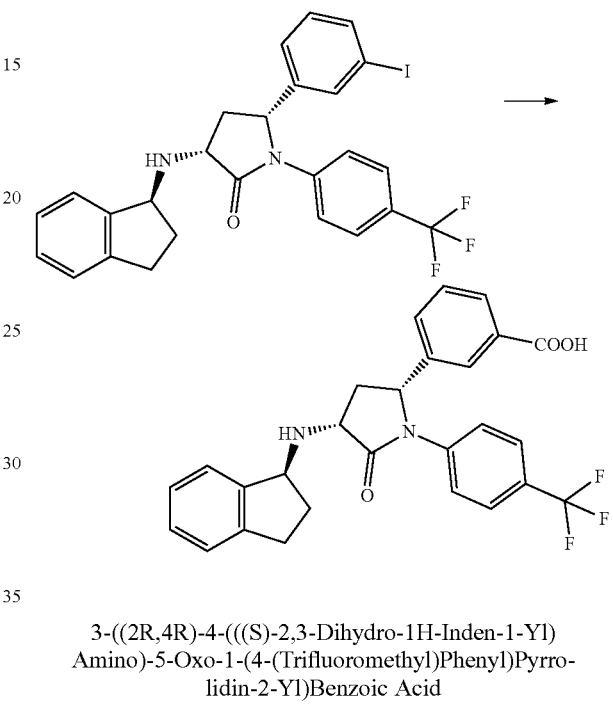

3-((2R,4R)-4-(((S)-2,3-Dihydro-1H-Inden-1-Yl)Amino)-5-Oxo-1-(4-(Trifluoromethyl)Phenyl)Pyrrolidin-2-Yl)Benzoic Acid A 35 mL sealed tube equipped with a stir bar was charged with oxalic acid dihydrate (1.5 equiv), palladium (II) acetate (1 mol %), triphenylphosphine (3 mol %), (3R,5R)-3-(((S)-2,3-dihydro-1H-inden-1-yl)amino)-5-(3-iodophenyl)-1-(4-(trifluoromethyl)phenyl)pyrrolidin-2-one, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO$_4$, filtered and the filtrate was passed through a short bed of silica gel, and the organic layer was concentrated, and the residue was taken directly to the next step (70%).

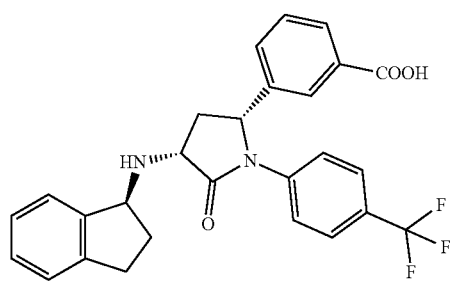

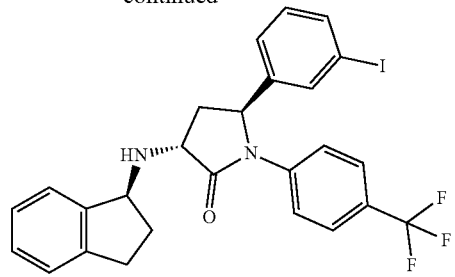

(3S,5S)-3-(((S)-2,3-Dihydro-1H-Inden-1-Yl)
Amino)-5-(3-Iodophenyl)-1-(4-(Trifluoromethyl)
Phenyl)Pyrrolidin-2-One and (3R,5S)-3-(((S)-2,3-Dihydro-1H-Inden-1-Yl)
Amino)-5-(3-Iodophenyl)-1-(4-(Trifluoromethyl)
Phenyl)Pyrrolidin-2-One Sodium cyanoborohydride (12.4 mmol) was added to a solution of (S)-3-(((S)-2,3-dihydro-1H-inden-1-yl)amino)-5-(3-iodophenyl)-1-(4-(trifluoromethyl)phenyl)-1,5-dihydro-2H-pyrrol-2-one (6.19 mmol) in glacial acetic acid (31 mL). The reaction mixture was stirred at ambient temperature for 1 h and concentrated in vacuo. The residue was dissolved in EtOAc and washed with a saturated NaHCO3 solution, water, and brine, dried (Na2SO4), and concentrated in vacuo. The material was purified by silica gel chromatography (10-30% EtOAc/hexanes) to afford a first eluting isomer, as a white solid (80%) and a second eluting isomer, as a clear colorless oil (4.3%).

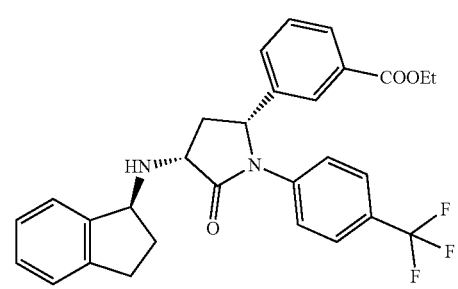

Ethyl 3-((2R,4R)-4-(((S)-2,3-Dihydro-1H-Inden-1-
Yl)Amino)-5-Oxo-1-(4-(Trifluoromethyl)Phenyl)
Pyrrolidin-2-Yl)Benzoate 3-((2R,4R)-4-(((S)-2,3-Dihydro-1H-inden-1-yl)amino)-5-oxo-1-(4-(trifluoromethyl)phenyl)pyrrolidin-2-yl)benzoic acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The organic layer was separated, dried over anhydrous MgSO4, filtered and the solvent was evaporated in vacuo to provide the ester as an off-white solid (87%).

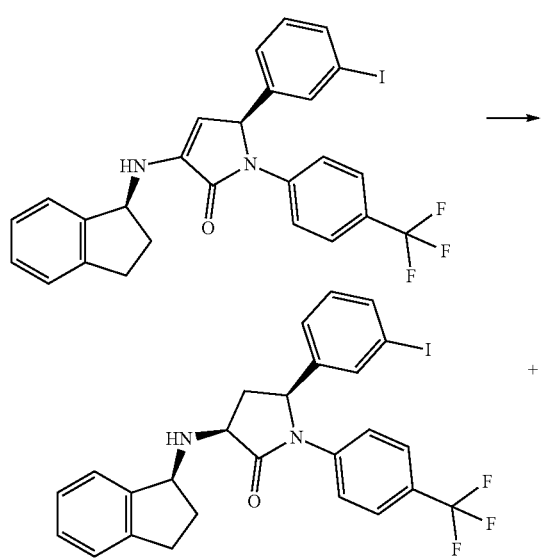

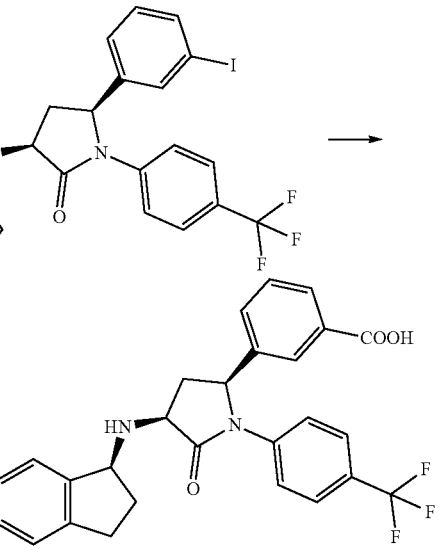

3-((2S,4S)-4-(((S)-2,3-Dihydro-1H-Inden-1-Yl)
Amino)-5-Oxo-1-(4-(Trifluoromethyl)Phenyl)Pyrro-
lidin-2-Yl)Benzoic Acid A 35 mL sealed tube equipped with a stir bar was charged with oxalic acid dihydrate (1.5 equiv), palladium (II) acetate (1 mol %), triphenylphosphine (3 mol %), (3S,5S)-3-(((S)-2,3-dihydro-1H-inden-1-yl)amino)-5-(3-iodophenyl)-1-(4-(trifluoromethyl)phenyl)pyrrolidin-2-one, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO₄, filtered and the filtrate was passed through a short bed of silica gel, and the organic layer was concentrated, and the residue was taken directly to the next step (70%).

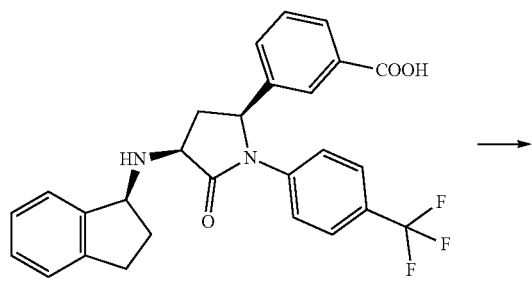

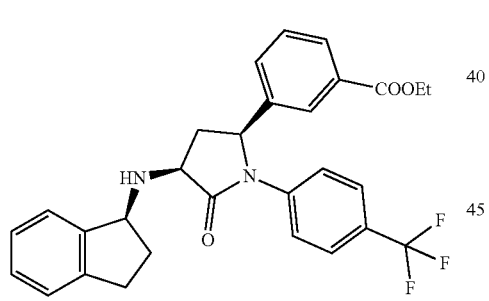

Ethyl 3-((2S,4S)-4-(((S)-2,3-Dihydro-1H-Inden-1-Yl)Amino)-5-Oxo-1-(4-(Trifluoromethyl)Phenyl)Pyrrolidin-2-Yl)Benzoate 3-((2S,4S)-4-(((S)-2,3-Dihydro-1H-inden-1-yl)amino)-5-oxo-1-(4-(trifluoromethyl)phenyl)pyrrolidin-2-yl)benzoic acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The organic layer was separated, dried over anhydrous MgSO₄, filtered and the solvent was evaporated in vacuo to provide the ester as an off-white solid (87%).

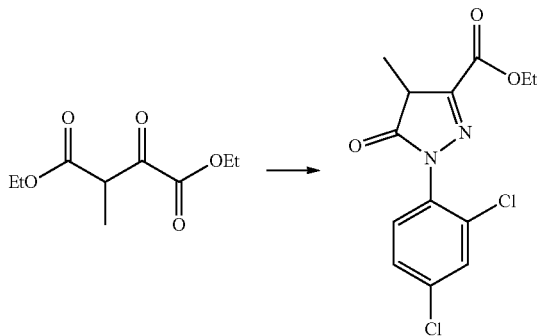 [SMILES: CCOC(=O)C(=O)C(C)C(=O)OCC ; CCOC(=O)C1=NN(c2ccc(Cl)cc2Cl)C(=O)C1C]

Ethyl 5-(4-Chlorophenyl)-1-(2,4-Dichlorophenyl)-4-Methyl-1H-Pyrazole-3-Carboxylate 2,4-Dichlorophenylhydrazine hydrochloride (126 g) is dissolved in 1 l of toluene and this solution is placed under nitrogen; after stirring, 100 g of diethyl 2-methyl-3-oxosuccinate (Sigma) are added and the mixture is then heated and 50 ml of TFA are added at 55° C. The mixture is left at the reflux of the solvent for 4 and a half hours, with stirring. The mixture is allowed to return to ambient temperature and is then heated to 75° C. and the reaction medium is hydrolyzed with 300 ml of water. The mixture is separated by settling out, the aqueous phase is discarded, and the organic phase is then evaporated in order to eliminate the residual TFA. The organic phase is taken up with 100 ml of toluene and the expected product then crystallizes (102 g).

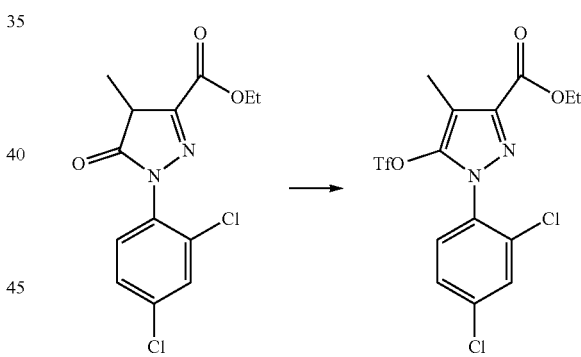

Ethyl 1-(2,4-Dichlorophenyl)-4-Methyl-5-(((Trifluoromethyl)Sulphonyl)Oxy)-1H-Pyrazole-3-Carboxylate Pyrazolone (50 gm) obtained in the preceding step is suspended in 250 ml of DCM, under nitrogen, and the mixture is cooled to 0° C. with stirring. 24 ml of TEA followed by 30 ml of triflic anhydride are added and the stirring is maintained at 0° C. for 15 minutes. The reaction medium is hydrolyzed with 200 ml of DCM. The reaction medium is separated by settling out and the organic phase is then washed with 200 ml of water. The aqueous phase is discarded. The organic phase is evaporated, and the oil obtained is chromatographed on silica, elution being carried out with a pentane/EtOAc mixture (90/10; v/v). The fractions containing the expected compound are combined and evaporated to dryness to obtain the final product (67.7 g).

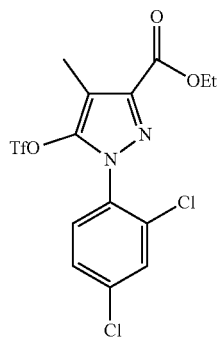 

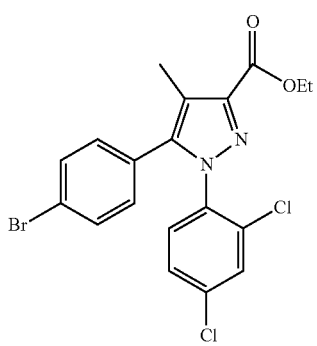

Ethyl 5-(4-Bromophenyl)-1-(2,4-Dichlorophenyl)-4-Methyl-1H-Pyrazole-3-Carboxylate 25.5 g of the pyrazole triflate of the preceding step, 10.8 g of 4-bromophenylboronic acid and 670 mg of tetrakis(triphenylphosphine)palladium are mixed, under nitrogen; 250 ml of ethyl acetate and 71 ml of a 2M aqueous sodium carbonate solution are added. The reaction medium is stirred at 65° C. for 6 hours. The reaction medium is separated by settling out, the aqueous phase is discarded, and the organic phase is then washed with 100 ml of water. After separation by settling out, the organic phase is evaporated off. The crude product obtained is purified by chromatography on silica, elution being carried out with a cyclohexane/EtOAc mixture (85/15; v/v) to provide the final product (18.9 g).

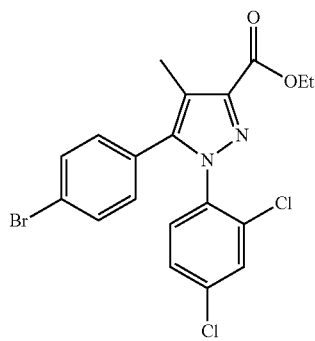 

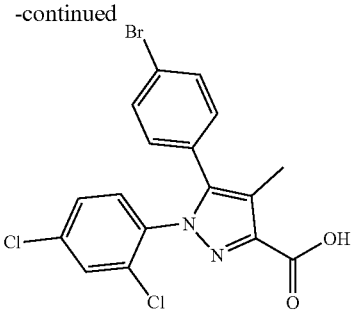

5-(4-Bromophenyl)-1-(2,4-Dichlorophenyl)-4-Methyl-1H-Pyrazole-3-Carboxylic Acid

The ester (10 g, 19.9 mmoles) obtained from the previous step was taken in a 500 ml single neck flask and to it 300 ml of 7:2:1 mixture of THF-methanol-water along with solid lithium hydroxide (2.5 g, 104.6 mol) was added. The mixture was refluxed for 12 hours. The solvents were removed and to the residue 200 ml of DCM was added. To that 100 ml of water was added and the water layer containing the lithium salt of the product was separated. The water layer was repeatedly washed with DCM (2×100), the water layer separated and was acidified to pH~2 using concentrated HCl. The organic layer was separated, washed with 100 ml of brine, dried over sodium sulphate and concentrated to give the purified acid free of any impurities. This purified acid was dried over $MgSO_4$, filtered and the filtrate was passed through a short bed of silica gel, and the organic layer was concentrated and the residue was taken directly to the next step (9.4 g, 100%).

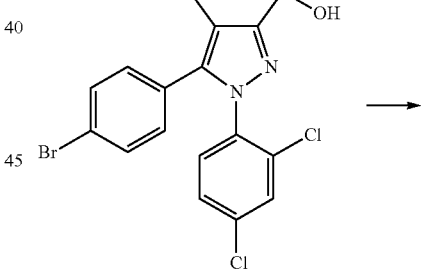

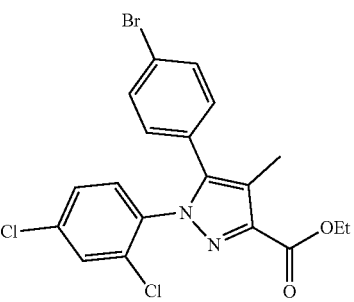

Ethyl 5-(4-Bromophenyl)-1-(2,4-Dichlorophenyl)-4-Methyl-1H-Pyrazole-3-Carboxylate The acid (7.5 g, 15.8 mmol) obtained was taken in a 500 ml single neck flask equipped with a nitrogen inlet and to it 200 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~100 mL). The organic layer was separated, dried over anhydrous MgSO₄, filtered and the solvent was evaporated in vacuo to provide the ester as an off-white solid (7 g, 87%).

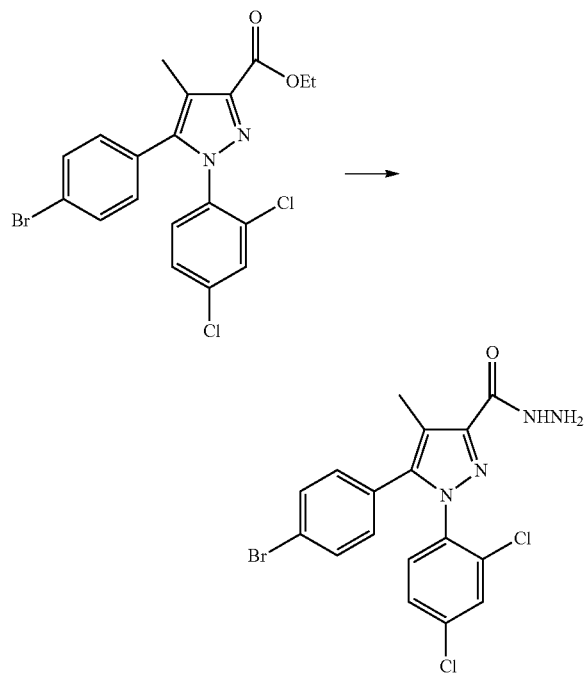

5-(4-Bromophenyl)-1-(2,4-Dichlorophenyl)-4-Methyl-1H-Pyrazole-3-Carbohydrazide

The ester (7 g, 15.4 mol) obtained was taken in a 500 ml single neck flask equipped with a nitrogen inlet and to it 50 ml of anhydrous ethyl alcohol followed by 20 g of hydrazine hydrate are added and the mixture is heated at reflux for 3 hours. The reaction medium is concentrated in vacuo with 10% residual solvent remaining. The combined residue is dissolved in dichloromethane (150 ml) and washed with deionized water (2×~100 mL). The organic layer was separated, dried over anhydrous MgSO₄, filtered and the filtrate was removed in vacuo. The residue obtained was purified by crystallization from ethyl acetate and hexane to provide the hydrazide as a white solid (5.2 g, 76%).

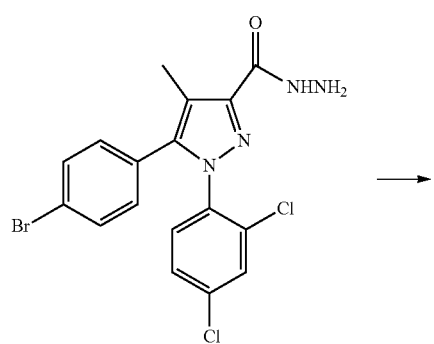

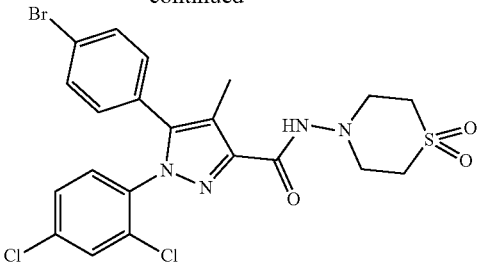

5-(4-Bromophenyl)-1-(2,4-Dichlorophenyl)-N-(1,1-Dioxidothiomorpholino)-4-Methyl-1H-Pyrazole-3-Carboxamide To a solution of the hydrazide (5 g, 11.4 mmol) in iPrOH (6 mL) was added divinyl sulfone (1.35 g, 11.4 mmol) dropwise and the contents were stirred overnight at room temperature. The solids obtained were filtered and washed with iPrOH (2×25 ml) and dried to provide the title compound. The crude compound upon crystallization from ethanol provided the title compound (3.5 g, 55%).

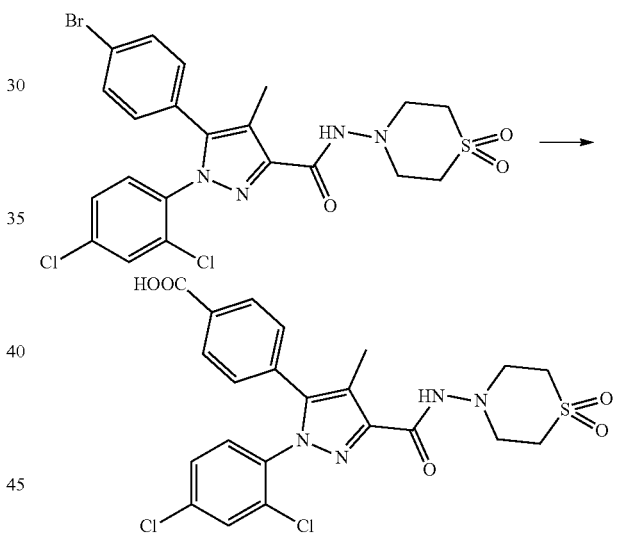

4-(1-(2,4-Dichlorophenyl)-3-((1,1-Dioxidothiomorpholino)Carbamoyl)-4-Methyl-1H-Pyrazol-5-Yl)Benzoic Acid A 35 mL sealed tube equipped with a stir bar was charged with oxalic acid dihydrate (1.5 equiv), palladium (II) acetate (1 mol %), xantphos (1 mol %), bromo compound (1 equiv), acetic anhydride (1.5 equiv), N,N-diisopropylethylamine (1.5 equiv), N,N-dimethylformamide under air. The tube was quickly sealed with a Teflon® high pressure valve, frozen in liquid nitrogen, evacuated and backfilled with N₂ (5 times). After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO₄, filtered and the filtrate was passed through a short bed of silica gel, and the organic layer was concentrated and the residue was taken directly to the next step (70%).

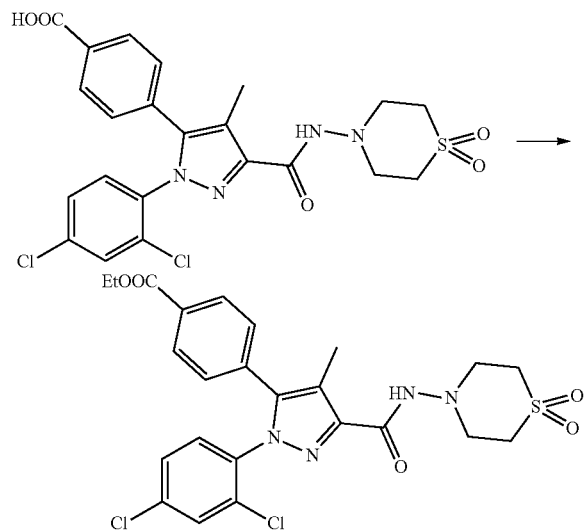

Ethyl 4-(1-(2,4-Dichlorophenyl)-3-((1,1-Dioxidothiomorpholino)Carbamoyl)-4-Methyl-1H-Pyrazol-5-Yl)Benzoate The acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2x~10 mL). The organic layer was separated, dried over anhydrous MgSO₄, filtered and the solvent was evaporated in vacuo to provide the ester as an off-white solid (87%).

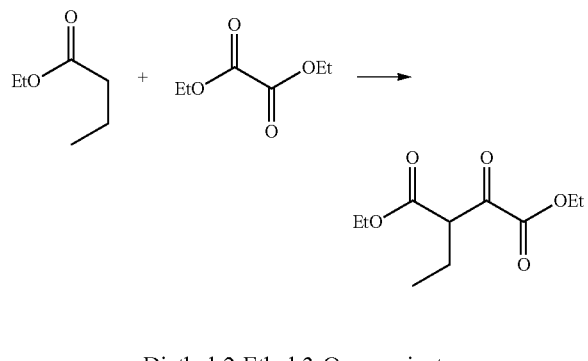

Diethyl 2-Ethyl-3-Oxosuccinate 27.8 mL of lithium diisopropylamide (50.0 mmol, 1.00 eq, 1.8 M in THF/heptane/ethylbenzene) were dissolved in 50 mL of dry THF und an argon atmosphere and cooled to −75. 6.64 mL of ethyl butanoate (50.0 mmol, 1.00 eq) were dissolved in 25 mL of dry THF and added to the previous solution at a bath temperature of −60 to −75 and stirred for an additional 1 h at a bath temperature of −75. 6.92 mL of diethyl oxalate (51.0 mmol, 1.02 eq) were dissolved in 25 mL of dry THF and added to the previous solution at a bath temperature of −60 to −75° and stirred for an additional 30 min at a bath temperature of −75. The mixture was allowed to come to. −20*C, at which temperature 6.47 mL of acetic acid (1 13.0 mmol, 2.26 eq), followed by 100 mL of water. The mixture was then allowed to come to rt. The separated organic layer was washed, once with water, once with sodium bicarbonate solution and once with brine, before being dried over sodium sulfate and concentrated in vacuo. The crude reaction product was used for the next transformation without any further purification.

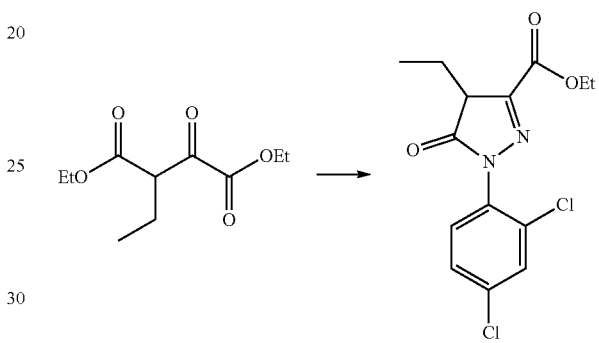

Ethyl 1-(2,4-Dichlorophenyl)-4-Ethyl-5-Oxo-4,5-Dihydro-1H-Pyrazole-3-Carboxylate 2,4-Dichlorophenylhydrazine hydrochloride (126 g) is dissolved in 1 l of toluene and this solution is placed under nitrogen; after stirring, 100 g of diethyl 2-methyl-3-oxosuccinate (Sigma) are added and the mixture is then heated and 50 ml of TFA are added at 55° C. The mixture is left at the reflux of the solvent for 4 and a half hours, with stirring. The mixture is allowed to return to ambient temperature and is then heated to 75° C. and the reaction medium is hydrolyzed with 300 ml of water. The mixture is separated by settling out, the aqueous phase is discarded, and the organic phase is then evaporated in order to eliminate the residual TFA. The organic phase is taken up with 100 ml of toluene and the expected product then crystallizes (102 g).

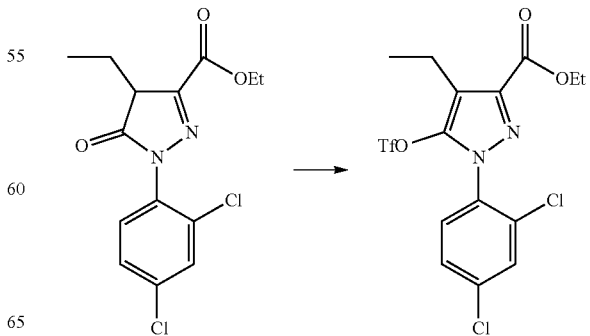

Ethyl 1-(2,4-Dichlorophenyl)-4-Ethyl-5-(((Trifluoromethyl)Sulfonyl)Oxy)-1H-Pyrazole-3-Carboxylate Pyrazolone (50 gm) obtained in the preceding step is suspended in 250 ml of DCM, under nitrogen, and the mixture is cooled to 0° C. with stirring. 24 ml of TEA followed by 30 ml of triflic anhydride are added and the stirring is maintained at 0° C. for 15 minutes. The reaction medium is hydrolyzed with 200 ml of DCM. The reaction medium is separated by settling out and the organic phase is then washed with 200 ml of water. The aqueous phase is discarded. The organic phase is evaporated, and the oil obtained is chromatographed on silica, elution being carried out with a pentane/EtOAc mixture (90/10; v/v). The fractions containing the expected compound are combined and evaporated to dryness to obtain the final product (67.7 g).

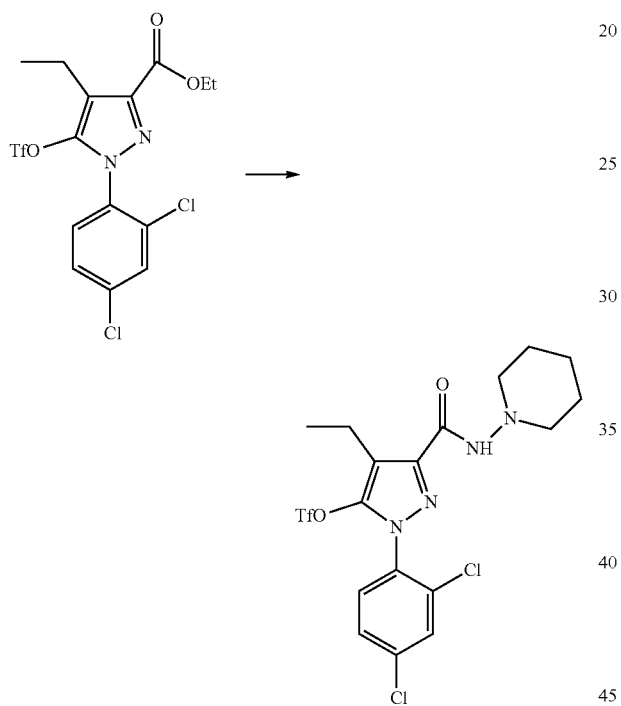

1-(2,4-Dichlorophenyl)-4-Ethyl-3-(Piperidin-1-Yl-carbamoyl)-1H-Pyrazol-5-Yl Trifluoromethanesulfonate To magnetically stirred suspension of AlCl$_3$ (9.8 g, 3 eq) in anhydrous dichloroethane (30 ml) at 0° C. was added 1-aminopiperidine (8.6 g, 3.5 eq) under argon atmosphere, and the resulting mixture was stirred at 0-5° C. for 25 min. Ethyl 1-(2,4-dichlorophenyl)-4-methyl-5-(((trifluoromethyl)sulfonyl)oxy)-1H-pyrazole-3-carboxylate (11 g) in dichloroethane (250 ml) was added, and the reaction mixture was slowly brought to room temperature over 30 minutes, and stirred at this temperature for 5 h. Reaction was quenched by adding 10% HCl (50 ml), and the biphasic mixture was stirred for 2 h. Organic layer was separate, and the aqueous layer was extracted with dichloromethane (3×50 ml). Combined organic layers were washed with water (2×80 ml), and brine (1×80 ml), dried over anhydrous MgSO$_4$, filtered and the solvent was removed in vacuo. The residue was purified by flash column chromatography on silica gel to give 9.5 g (77% yield) of product as a white solid.

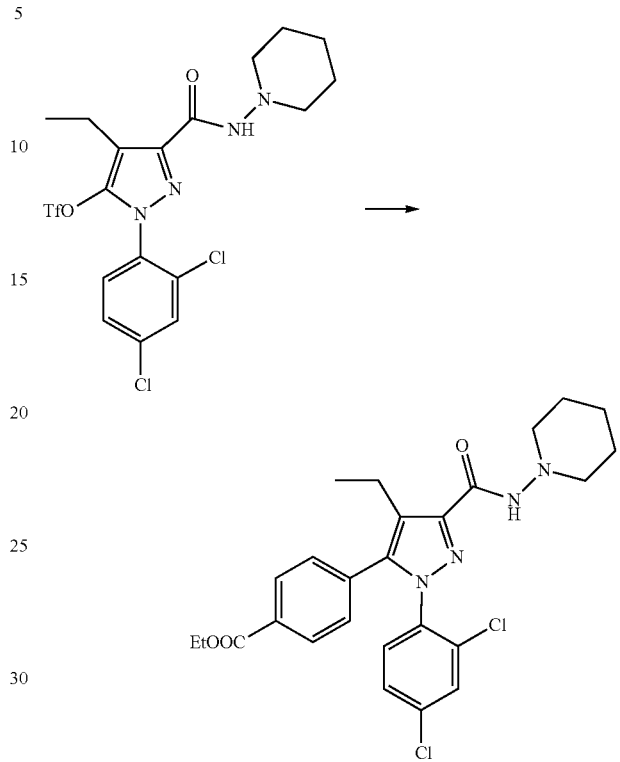

Ethyl 4-(1-(2,4-Dichlorophenyl)-4-Ethyl-3-(Piperidin-1-Ylcarbamoyl)-1H-Pyrazol-5-Yl)Benzoate (Compound 1)

(Ethoxycarbonyl)phenyl)boronic acid and 350 mg of tetrakis(triphenylphosphine)palladium are mixed, under nitrogen; 250 ml of ethyl acetate and 35 ml of a 2M aqueous sodium carbonate solution are added. The reaction medium is stirred at 65° C. for 6 hours. The reaction medium is separated by settling out, the aqueous phase is discarded, and the organic phase is then washed with 100 ml of water. After separation by settling out, the organic phase is evaporated off. The crude product obtained is purified by filtration and crystallization from a mixture of ethyl acetate and hexane to provide the final product (6 g).

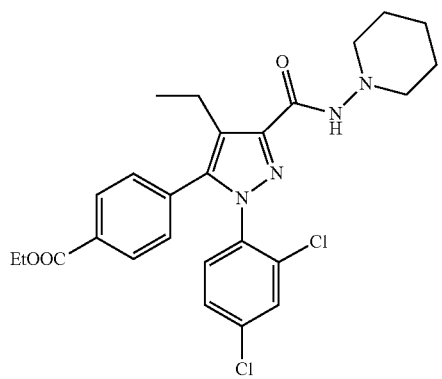

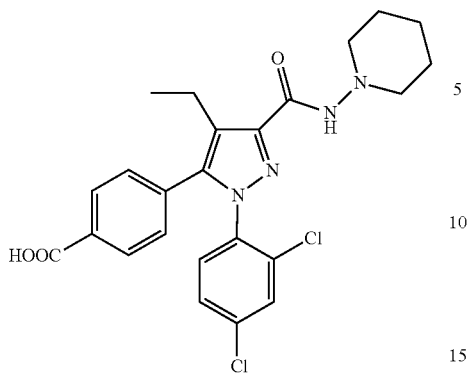

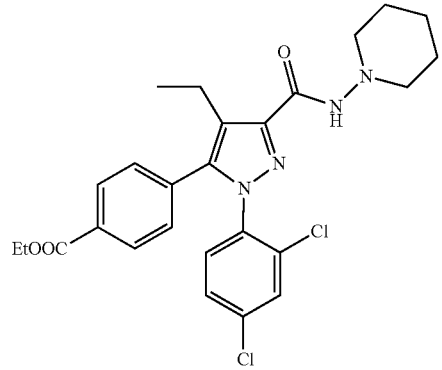

Purification of Final Product: Hydrolysis and Re-Esterification 4-(1-(2,4-Dichlorophenyl)-4-Ethyl-3-(Piperidin-1-Ylcarbamoyl)-1H-Pyrazol-5-Yl)Benzoic Acid Ethyl 4-(1-(2,4-Dichlorophenyl)-4-Ethyl-3-(Piperidin-1-Ylcarbamoyl)-1H-Pyrazol-5-Yl)Benzoate (Compound 1)

The ester (10 g, 19.9 mmoles) obtained was taken in 500 ml single neck flask and to it 300 ml of 7:2:1 mixture of THF-methanol-water along with solid lithium hydroxide (2.5 g, 104.6 mol) was added. The mixture was refluxed for 12 hours. The solvents were removed and to the residue 200 ml of DCM was added. To that 100 ml of water was added and the water layer containing the lithium salt of the product was separated. The water layer was repeatedly washed with DCM (2×100), the water layer separated and was acidified to pH~2 using concentrated HCl. The organic layer was separated, washed with 100 ml of brine, dried over sodium sulphate and concentrated to give the purified acid free of any impurities. This purified acid was dried over MgSO$_4$, filtered and the filtrate was passed through a short bed of silica gel, and the organic layer was concentrated and the residue was taken directly to the next step (9.4 g, 100%).

The acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The contents were brought to pH 6-7 and the organic layer was separated, dried over anhydrous MgSO$_4$, filtered and the solvent was evaporated in vacuo to provide the ester as an off-white solid (87%).

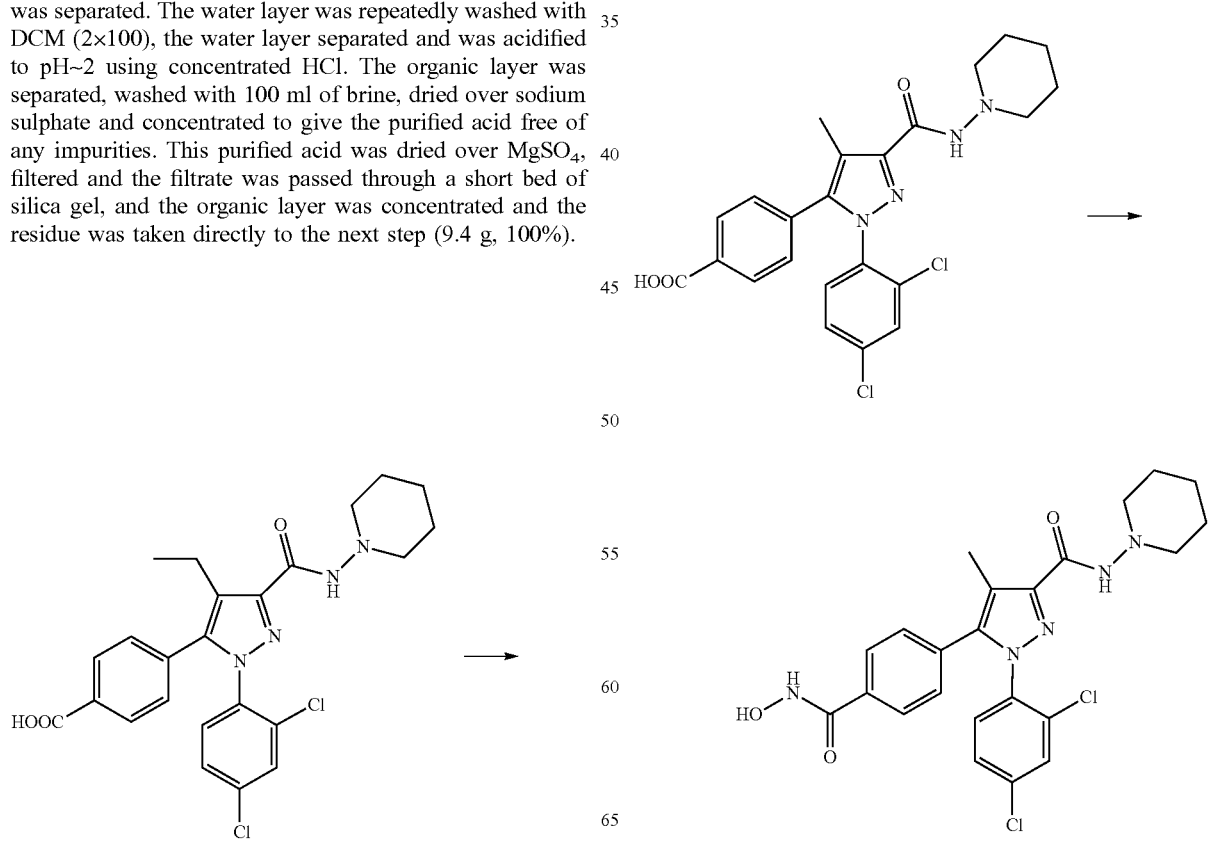

1-(2,4-Dichlorophenyl)-5-(4-(Hydroxycarbamoyl)Phenyl)-4-Methyl-N-(Piperidin-1-Yl)-1H-Pyrazole-3-Carboxamide Acid (2.9 mmol) was dissolved in DCM (0.4M) with catalytic DMF. To this solution cooled to 0° C. (ice bath) was added dropwise oxalyl chloride (3.48 mmol). The mixture was stirred at room temperature for 1 h and evaporated under reduced pressure (temp max 25° C.). The residue was dissolved in DCM (0.4M). To this solution cooled to 0° C. (ice bath) was added dropwise DIEA (7.8 mmol.). Then O-tritylhydroxylamine (3.19 mmol) was added and the mixture was stirred at room temperature for 4 h. Control of reaction was performed by TLC. The mixture was washed once with aqueous NaHCO3 5% and three times with water, and the combined organic layers were dried over MgSO$_4$ and evaporated. O-Trityl hydroxamate intermediate was dissolved in TFA 2%/DCM (0.03 M), and triisopropylsilane was added dropwise until the yellow color disappeared. Solvents were removed under reduced pressure, and the residue was washed with petroleum ether to give the title compound (47%).

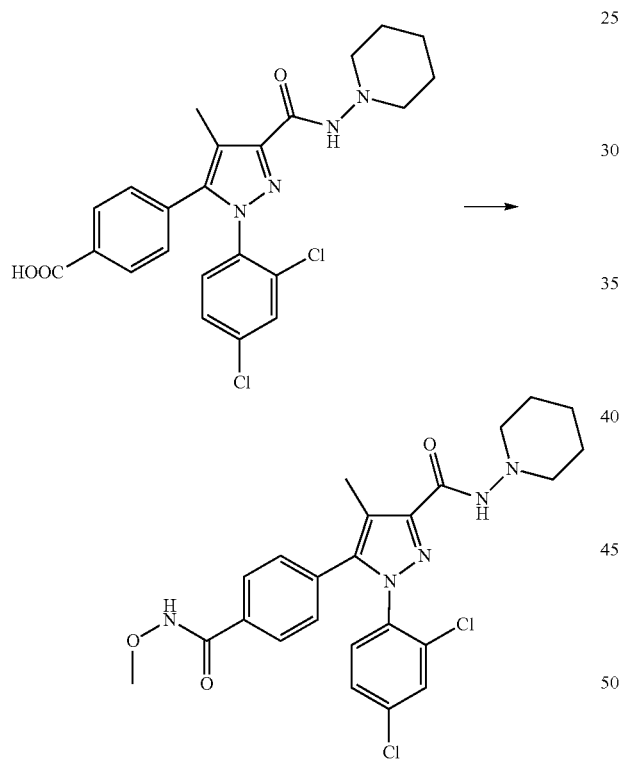

To a solution of the carboxylic acid (3.3 mmol, 1 equiv) in dry DCM (10 mL) was added oxalyl chloride (4.0 mmol, 1.2 equiv) dropwise at 0° C., followed by a catalytic amount of dry DMF (2 drops). The reaction was stirred at room temperature until the acid was completely consumed (typically 8 h). The solvent was removed under vacuum to afford the corresponding crude acyl chloride. Methoxyamine hydrochloride (4.0 mmol, 1.2 equiv) was added to a biphasic mixture of K2CO3 (6.6 mmol, 2 equiv) in a mixture of EtOAc (240 mL) and H2O (120 mL). The mixture was cooled to 0° C., and then acyl chloride in a minimum amount of EtOAc was added dropwise. The reaction was stirred 8 h at room temperature. The organic phase was separated, and the aqueous phase was extracted twice with EtOAc and dried over MgSO$_4$. The solvent was evaporated to give the title compound (92%).

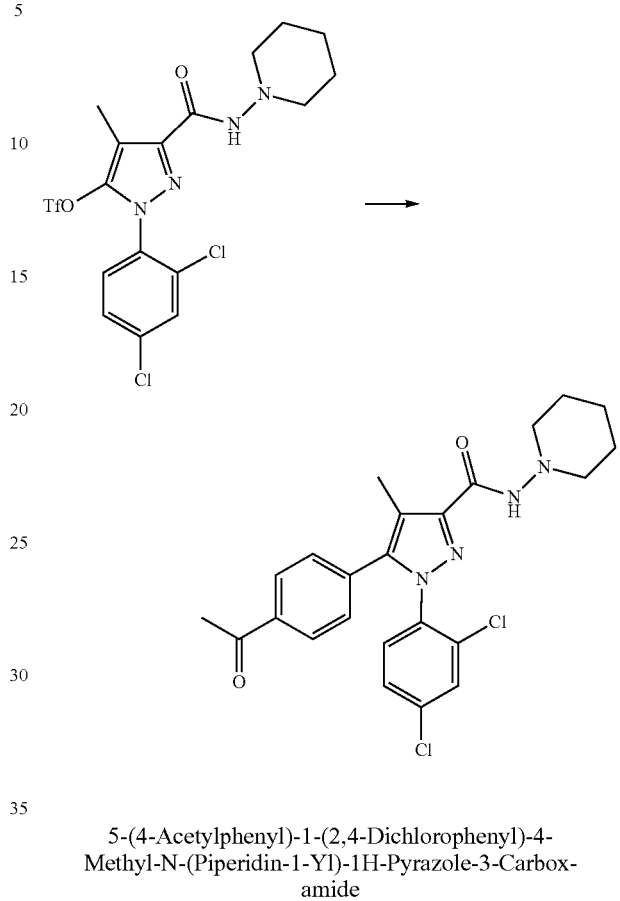

5-(4-Acetylphenyl)-1-(2,4-Dichlorophenyl)-4-Methyl-N-(Piperidin-1-Yl)-1H-Pyrazole-3-Carboxamide (4-acetylphenyl)boronic acid and 350 mg of tetrakis(triphenylphosphine)palladium are mixed, under nitrogen; 250 ml of ethyl acetate and 35 ml of a 2M aqueous sodium carbonate solution are added. The reaction medium is stirred at 65° C. for 6 hours. The reaction medium is separated by settling out, the aqueous phase is discarded, and the organic phase is then washed with 100 ml of water. After separation by settling out, the organic phase is evaporated off. The crude product obtained is purified by filtration and crystallization from a mixture of ethyl acetate and hexane to provide the final product (6 g).

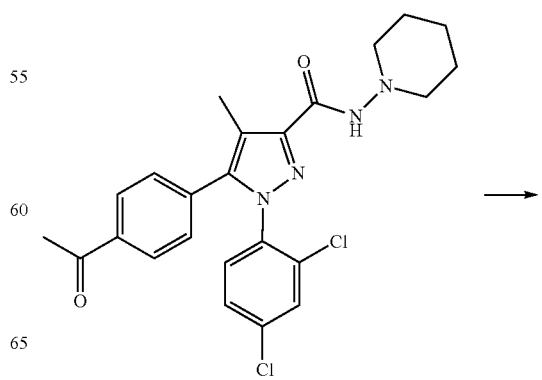

-continued

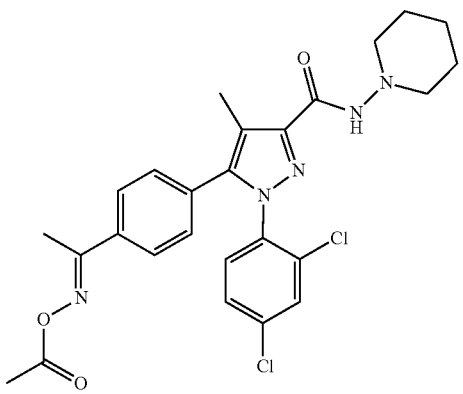

(E)-5-(4-(1-(Acetoxyimino)Ethyl)Phenyl)-1-(2,4-Dichlorophenyl)-4-Methyl-N-(Piperidin-1-Yl)-1H-Pyrazole-3-Carboxamide To a solution of acetophenone (22.0 mmol) and pyridine (61.8 mmol) in EtOH (10 mL) was added NH2OH·HCl (33.0 mmol) in one portion and the reaction mixture was stirred at 60° C. for 1 h. The reaction was quenched by adding water and the organic materials were extracted twice with ethyl acetate. The combined extracts were washed with 1 N aqueous HCl and brine and dried over MgSO$_4$. Volatile materials were removed in vacuo to give acetophenone oxime, which was used for the next acetylation without further purification. The crude residue of acetophenone oxime obtained above was treated with Ac2O (44.4 mmol) and a catalytic amount of DMAP (5 mg) in pyridine (10 mL) and the reaction mixture was stirred at room temperature for 1 h. After volatile materials were evaporated, the resulting residue was treated with water, and organic materials were extracted twice with ethyl acetate. The combined extracts were washed with 1 N aqueous HCl and brine and dried over MgSO$_4$. The solvents were removed under reduced pressure, giving white solid of crude acetophenone O-acetyl oxime. Further recrystallization was conducted from ethyl acetate-hexane to provide (E)-acetophenone O-acetyl oxime (63%).

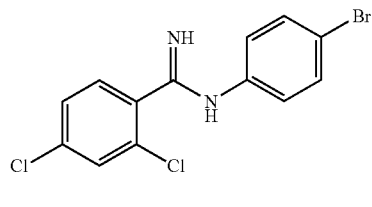

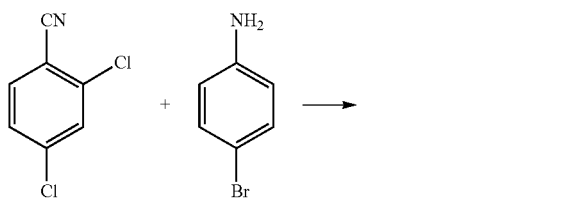

N-(4-Bromophenyl)-2,4-Dichlorobenzimidamide

To a magnetically stirred solution of EtMgBr (3.3 mL, 3M in diethyl ether, 10 mmol) in THF (30 mL) 4-bromoaniline (1.72 g, 10 mmol) was slowly added portion wise. After the solution was stirred for 30 min., 2,4-dichlorobenzonitrile (1.72 g, 10 mmol) was added. The resulting solution was stirred at room temperature (RT) overnight. The reaction mixture was quenched with water and extracted with ethyl acetate. The combined extracts were dried over anhydrous MgSO$_4$, filtered and evaporated under reduced pressure to give the benzimidamide as an off-white solid (2.45 g, 71.2%).

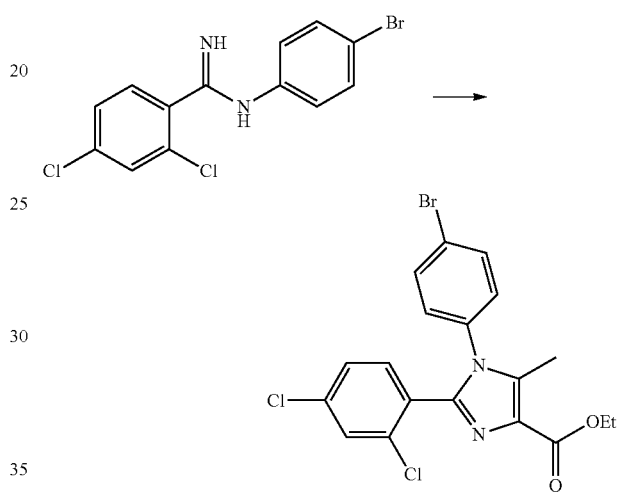

Ethyl 1-(4-Bromophenyl)-2-(2,4-Dichlorophenyl)-5-Methyl-1H-Imidazole-4-Carboxylate To a magnetically stirred solution of above amidine intermediate (2.45 g, 7 mmol) in 30 mL anhydrous toluene were added ethyl 3-bromo-2-oxobutanoate (1.48 g, 7 mmol) and Na$_2$CO$_3$ (0.74 g, 7 mmol). The contents were stirred at 100° C. for 12 hours. The reaction was brought to RT. The reaction mixture was quenched with water and extracted with ethyl acetate. The combined extracts were dried over anhydrous MgSO$_4$, filtered and evaporated under reduced pressure. Purification by column chromatography gave the ester as pale white solid (1.5 g, 46.4%).

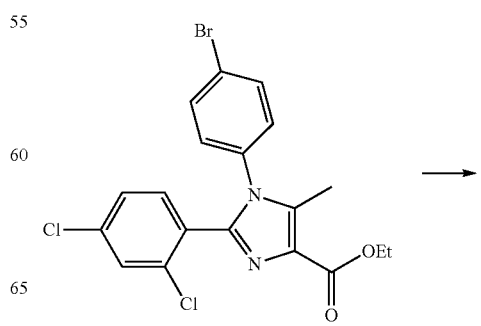

-continued

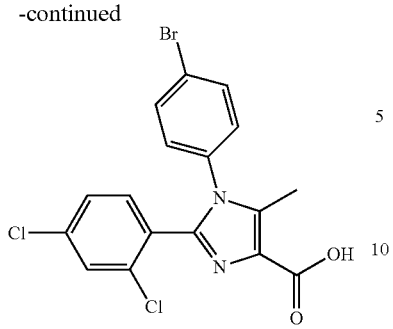

1-(4-Bromophenyl)-2-(2,4-Dichlorophenyl)-5-Methyl-1H-Imidazole-4-Carboxylic Acid The ester (10 g, 19.9 mmoles) obtained from the previous step was taken in a 500 ml single neck flask and to it 300 ml of 7:2:1 mixture of THF-methanol-water along with solid lithium hydroxide (2.5 g, 104.6 mol) was added. The mixture was refluxed for 12 hours. The solvents were removed and to the residue 200 ml of DCM was added. To that 100 ml of water was added and the water layer containing the lithium salt of the product was separated. The water layer was repeatedly washed with DCM (2×100), the water layer separated and was acidified to pH~2 using concentrated HCl. The organic layer was separated, washed with 100 ml of brine, dried over sodium sulphate and concentrated to give the purified acid free of any impurities. This purified acid was dried over MgSO$_4$, filtered and the filtrate was passed through a short bed of silica gel, and the organic layer was concentrated and the residue was taken directly to the next step (9.4 g, 100%).

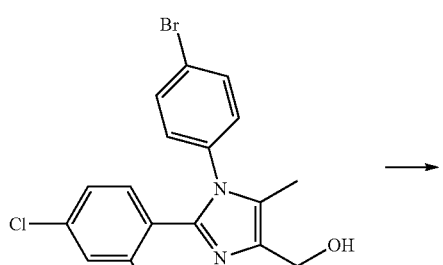

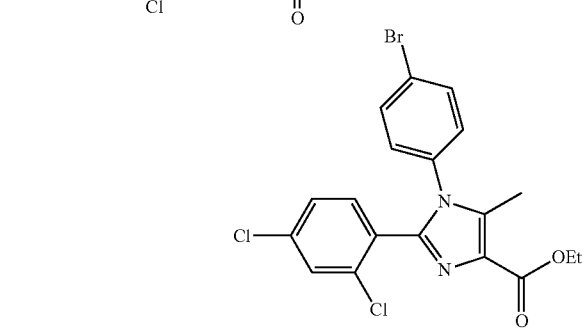

Ethyl 1-(4-Bromophenyl)-2-(2,4-Dichlorophenyl)-5-Methyl-1H-Imidazole-4-Carboxylate The acid (7.5 g, 15.8 mmol) obtained was taken in a 500 ml single neck flask equipped with a nitrogen inlet and to it 200 ml of anhydrous ethyl alcohol. To this was added few drops of sulfuric acid and the mixture was refluxed for 12 hours. The solvents were removed, and the residue was dissolved in dichloromethane (100 ml) and washed with deionized water (2×~100 mL). The contents were brought to pH 6-7 and the organic layer was separated, dried over anhydrous MgSO$_4$, filtered and the solvent was evaporated in vacuo to provide the ester as an off-white solid (7 g, 87%).

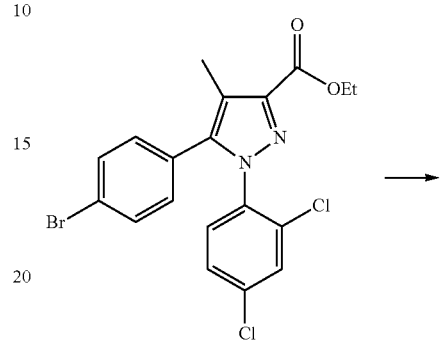

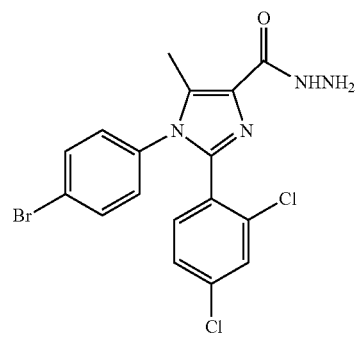

1-(4-Dromophenyl)-2-(2,4-Dichlorophenyl)-5-Methyl-1H-Imidazole-4-Carbohydrazide

The ester (7 g, 15.4 mol) obtained was taken in a 500 ml single neck flask equipped with a nitrogen inlet and to it 50 ml of anhydrous ethyl alcohol followed by 20 g of hydrazine hydrate are added and the mixture is heated at reflux for 3 hours. The reaction medium is concentrated in vacuo with 10% residual solvent remaining. The combined residue is dissolved in dichloromethane (150 ml) and washed with deionized water (2×~100 mL). The organic layer was separated, dried over anhydrous MgSO$_4$, filtered and the filtrate was removed in vacuo. The residue obtained was purified by crystallization from ethyl acetate and hexane to provide the hydrazide as a white solid (5.2 g, 76%).

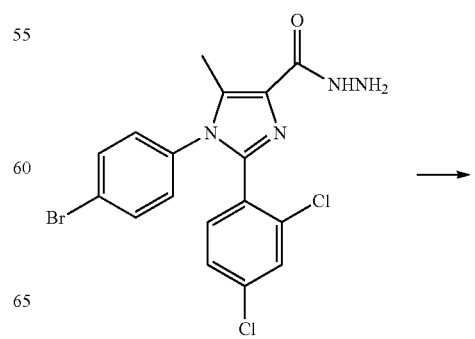

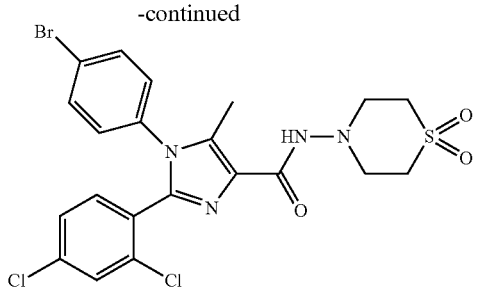

1-(4-Bromophenyl)-2-(2,4-Dichlorophenyl)-N-(1,1-Dioxidothiomorpholino)-5-Methyl-1H-Imidazole-4-Carboxamide To a solution of the hydrazide (5 g, 11.4 mmol) in iPrOH (6 mL) was added divinyl sulfone (1.35 g, 11.4 mmol) dropwise and the contents were stirred overnight at room temperature. The solids obtained were filtered and washed with iPrOH (2×25 ml) and dried to provide the title compound. The crude compound upon crystallization from ethanol provided the title compound (3.5 g, 55%).

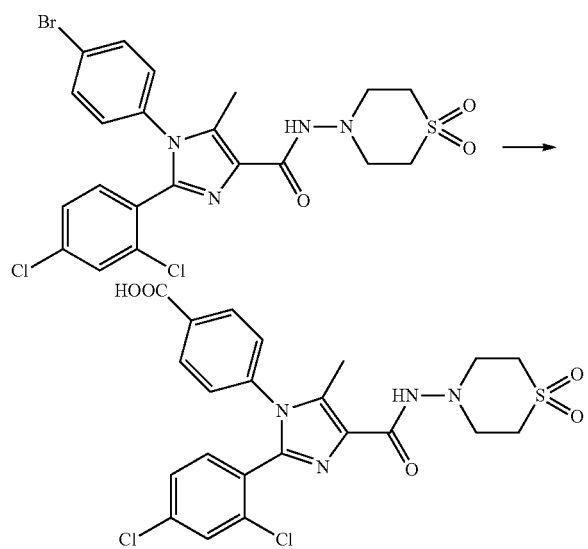

4-(2-(2,4-Dichlorophenyl)-4-((1,1-Dioxidothiomorpholino)Carbamoyl)-5-Methyl-1H-Imidazol-1-Yl)Benzoic Acid A 35 mL sealed tube equipped with a stir bar was charged with oxalic acid dihydrate (1.5 equiv), palladium (II) acetate (1 mol %), xantphos (1 mol %), bromo compound (1 equiv), acetic anhydride (1.5 equiv), N,N-diisopropylethylamine (1.5 equiv), N,N-dimethylformamide under air. The tube was quickly sealed with a Teflon® high pressure valve, frozen in liquid nitrogen, evacuated and backfilled with $N_2$ (5 times). After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over $MgSO_4$, filtered and the filtrate was passed through a short bed of silica gel, and the organic layer was concentrated, and the residue was taken directly to the next step (70%).

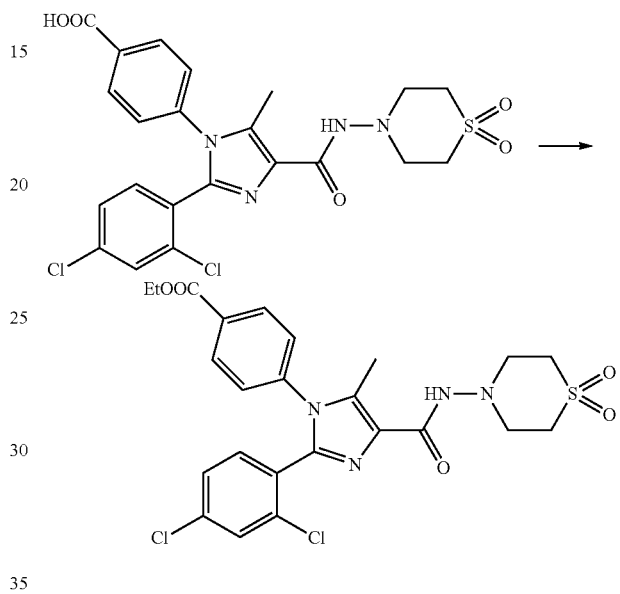

Ethyl 4-(2-(2,4-Dichlorophenyl)-4-((1,1-Dioxidothiomorpholino)Carbamoyl)-5-Methyl-1H-Imidazol-1-Yl)Benzoate The acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2×~10 mL). The contents were brought to pH 6-7 and the organic layer was separated, dried over anhydrous $MgSO_4$, filtered and the solvent was evaporated in vacuo to provide the ester as an off-white solid (87%).

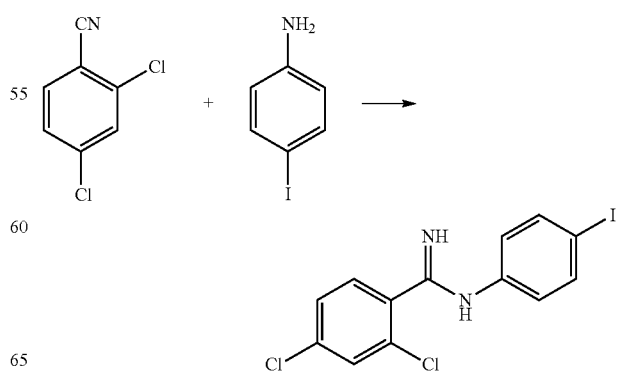

2,4-Dichloro-N-(4-Iodophenyl)Benzimidamide

To a magnetically stirred solution of EtMgBr (10 mmol) in THF (30 mL) 4-iodoaniline (10 mmol) was slowly added portion wise. After the solution was stirred for 30 min., 2,4-dichlorobenzonitrile (10 mmol) was added. The resulting solution was stirred at room temperature (RT) overnight. The reaction mixture was quenched with water and extracted with ethyl acetate. The combined extracts were dried over anhydrous MgSO$_4$, filtered and evaporated under reduced pressure to give the benzimidamide as an off-white solid (71.2%).

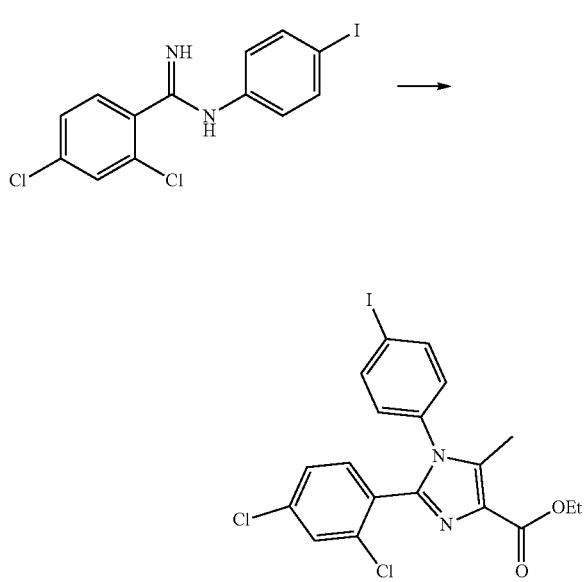 [SMILES: N=C(Nc1ccc(I)cc1)c1ccc(Cl)cc1Cl ; CCOC(=O)c1nc(-c2ccc(Cl)cc2Cl)n(-c2ccc(I)cc2)c1C]

Ethyl 2-(2,4-Dichlorophenyl)-1-(4-Iodophenyl)-5-Methyl-1H-Imidazole-4-Carboxylate To a magnetically stirred solution of above amidine intermediate (7 mmol) in 30 mL anhydrous toluene were added ethyl 3-bromo-2-oxobutanoate (7 mmol) and Na2CO3 (7 mmol). The contents were stirred at 100° C. for 12 hours. The reaction was brought to RT. The reaction mixture was quenched with water and extracted with ethyl acetate. The combined extracts were dried over anhydrous MgSO$_4$, filtered and evaporated under reduced pressure. Purification by column chromatography gave the ester as pale white solid (46.4%).

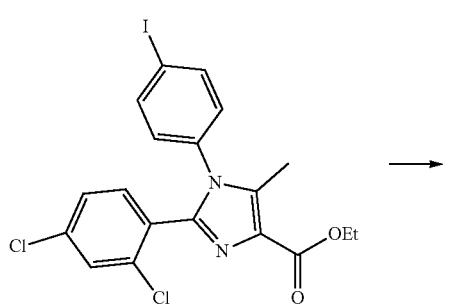

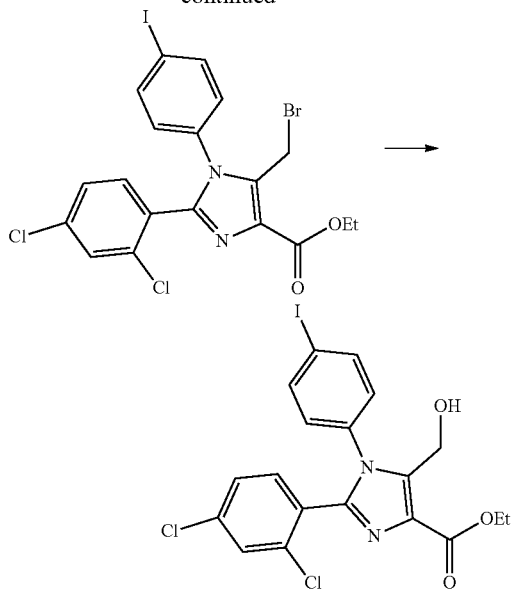

Ethyl 2-(2,4-Dichlorophenyl)-5-(Hydroxymethyl)-1-(4-Iodophenyl)-1H-Imidazole-4-Carboxylate To magnetically stirred solution of ester (0.0025 mol) in anhydrous CCl4 (50 ml) was added N-bromosuccinimide (0.00275 mol) and 2,2'-azo-bis-isibutyrylnitrile (0.02 g) at room temperature. The resulting solution was degassed by vacuum-thaw cycle and heated to reflux under argon atmosphere. Reaction mixture was stirred under reflux for 24 h and then cooled to room temperature. Diluted with dichloromethane (50 ml) and washed with water (2×40 ml), and saturated aqueous sodium chloride solution (50 ml). Organic layer was dried over anhydrous MgSO$_4$ and concentrated. Resulting oil was not purified, but directly used to the next step.

The intermediate bromo derivative was dissolved in DMSO:H2O (6:1, 30 ml) and the resulting solution was magnetically stirred at 60° C., for 5 h. Reaction mixture was cooled to room temperature, diluted with water (100 ml) and extracted with ethyl acetate (3×50 ml). Combined organic layers were washed with water (2×60 ml), and brine (90 ml), dried over anhydrous MgSO$_4$, filtered, and the solvent was evaporated. Crude product was purified by flash column chromatography on silica gel (elution petroleum ether:ethyl acetate 7:3) to provide the title compound (67%).

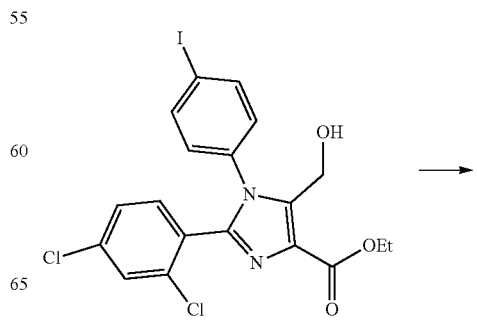

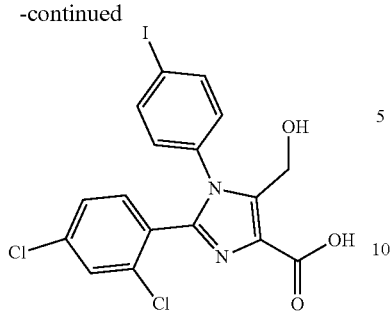

2-(2,4-Dichlorophenyl)-5-(Hydroxymethyl)-1-(4-Iodophenyl)-1H-Imidazole-4-Carboxylic Acid The ester (19.9 mmoles) obtained from the previous step was taken in a 500 ml single neck flask and to it 300 ml of 7:2:1 mixture of THF-methanol-water along with solid lithium hydroxide (104.6 mol) was added. The mixture was refluxed for 12 hours. The solvents were removed and to the residue 200 ml of DCM was added. To that 100 ml of water was added and the water layer containing the lithium salt of the product was separated. The water layer was repeatedly washed with DCM (2×100), the water layer separated and was acidified to pH~2 using concentrated HCl. The organic layer was separated, washed with 100 ml of brine, dried over sodium sulphate and concentrated to give the purified acid free of any impurities. This purified acid was dried over MgSO$_4$, filtered and the filtrate was passed through a short bed of silica gel, and the organic layer was concentrated, and the residue was taken directly to the next step (100%).

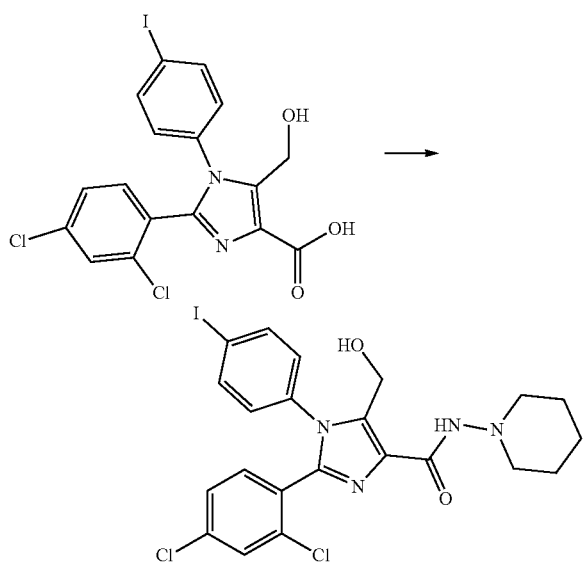

2-(2,4-Dichlorophenyl)-5-(Hydroxymethyl)-1-(4-Iodophenyl)-N-(Piperidin-1-Yl)-1H-Imidazole-4-Carboxamide The acid (15.8 mmol) obtained was taken in a 500 ml single neck flask equipped with a nitrogen inlet and to it 200 ml of DCM, 1-aminopiperidine (17.4 mmol), N,N,N',N'-tetramethyl-O-(benzotriazol-1-yl)uronium tetrafluoroborate (17.4 mmol) and Hüinig's base (17.4 mmol) were added and the contents were stirred for 1 hour. To the reaction mixture, 100 ml of water was added, and the contents were acidified to pH~2 using concentrated HCl. The organic layer was separated, washed with brine, dried over sodium sulphate and concentrated to give the amide (72%).

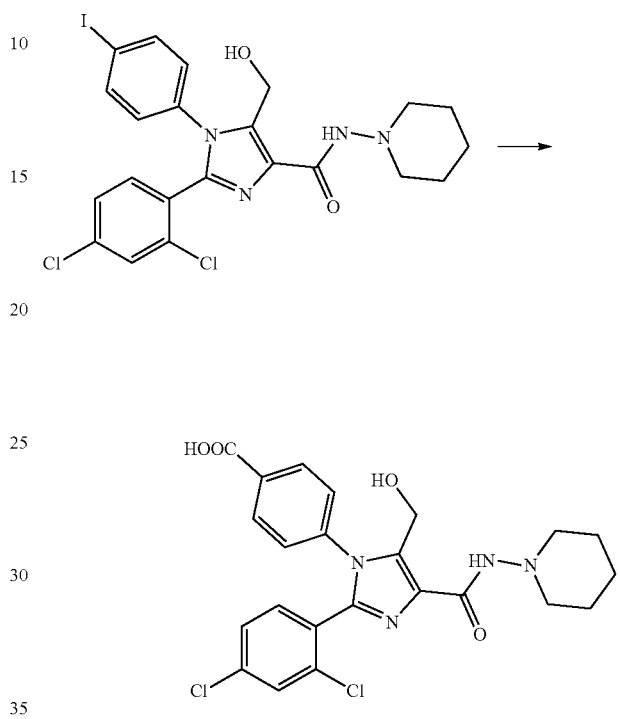

4-(2-(2,4-Dichlorophenyl)-5-(Hydroxymethyl)-4-(Piperidin-1-Ylcarbamoyl)-1H-Imidazol-1-Yl)Benzoic Acid A 35 mL sealed tube equipped with a stir bar was charged with oxalic acid dihydrate (1.5 equiv), palladium (II) acetate (1 mol %), triphenylphosphine (3 mol %), (3S,5S)-3-(((S)-2,3-dihydro-1H-inden-1-yl)amino)-5-(3-iodophenyl)-1-(4-(trifluoromethyl)phenyl)pyrrolidin-2-one, acetic anhydride (1.5 equiv), N,N-diisopropylethylamine (1.5 equiv), N,N-dimethylformamide under air. The tube was quickly sealed with a Teflon® high pressure valve. After the reaction mixture was stirred in a preheated oil bath for 6 h, it was allowed to cool down to room temperature. The DMF were removed in vacuo and to the residue 20 ml of DCM and 10 ml of water was added. To the mixture 1 ml of 1 N NaOH was added and after stirring vigorously, the water layer containing the sodium salt of the product was separated. The water layer was repeatedly washed with DCM (2×10), the water layer separated and to this 20 ml of DCM was added and the mixture was neutralized to pH~6-7 using concentrated HCl while stirring. The organic layer was separated, washed with 10 ml of brine, dried over sodium sulphate and concentrated to give the purified acid free of any impurities. This purified acid was dried over MgSO$_4$, filtered and the filtrate was passed through a short bed of silica gel, and the organic layer was concentrated, and the residue was taken directly to the next step (70%).

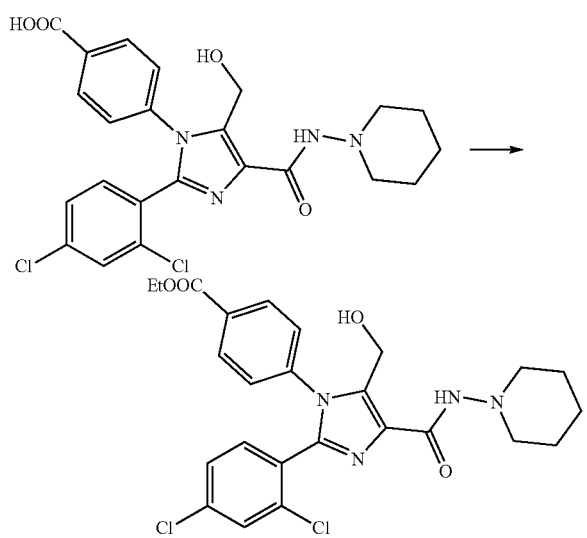

Ethyl 4-(2-(2,4-Dichlorophenyl)-5-(Hydroxymethyl)-4-(Piperidin-1-Ylcarbamoyl)-1H-Imidazol-1-Yl)Benzoate The acid obtained was taken in a 50 ml single neck flask equipped with a nitrogen inlet and to it 20 ml of anhydrous ethyl alcohol. To this was added few drops of sulfuric acid and the mixture was refluxed for 12 hours. The solvents were removed, and the residue was dissolved in dichloromethane (10 ml) and washed with deionized water (2x~10 mL). The contents were brought to pH 6-7 and the organic layer was separated, dried over anhydrous $MgSO_4$, filtered and the solvent was evaporated in vacuo to provide the ester as an off-white solid (87%).

Membrane Preparations from Tissue Culture Sources

HEK293 cells expressing hCB1, hCB2 or mCB2 receptor are used for membrane preparations according to the method described in *J Neurochem* 1999, 72, (5), 2032-8, herein incorporated by reference in its entirety. The resulting pellet is resuspended in 10 mM Tris-chloride, pH 7.4 with 5 mM $MgCl_2$ and 2 mM EDTA (TME), and stored at −80° C. for no longer than two months. Protein content is assayed by using the Bio-Rad DC protein assay according to the manufacturer's protocol.

Membrane Preparations from Tissue Sources

Frozen rat brains (CB1 source) are obtained from Pel-Freeze Biologicals (Rogers, AK) and stored at −80° C. until use. Membranes are prepared according to the method described in *Brain Res* 1981, 226, (1-2), 107-18 and adapted as previously reported in *J Med Chem* 1994, 37, (23), 3867-70 and *Life Sci* 1995, 56, (23-24), 1957-62; each herein incorporated by reference in its entirety.

rCB1, hCB2, and mCB2 Binding Assays

The compounds were tested for their ability to bind to CB1 and CB2 receptors using rat brain or HEK293 cell membranes expressing hCB2 and mCB2 membrane preparations, respectively, as described in *J Med Chem* 1999, 42, (4), 769-776, *J Med Chem* 1994, 37, (23), 3867-70 and *Life Sci* 1995, 56, (23-24), 1957-62 (each herein incorporated by reference in its entirety) via competition-equilibrium binding using [$^3$H]CP-55,940. The results are analyzed using nonlinear regression to determine the actual $IC_{50}$ of the ligand (Prizm by GraphPad Software, Inc.) and the Ki values are calculated from the $IC_{50}$ as described in *Biochemical Pharmacology* 1973, 22, (23), 3099-3108; herein incorporated by reference in its entirety. Competition binding for a compound of Formula I-XI toward CB1 range from Ki~1 to 100 nM.

In Vivo Studies: All animals received care according to the Guide for the Care and Use of Laboratory Animals (Department of Health and Human Services Publication). All of the procedures used in the studies were approved by the organization's Institutional Animal Care and Use Committee.

Observation Chamber Test—CB1 Antagonist Mediated Side Effects

Observation chambers were used to score (count/duration) individual mouse intrinsic behavior. Male CD-1 mice (n=8) were placed in the chambers for 30 minutes to acclimate to the environment. Subjects were dosed i.v with a compound of Formula I-XI along with vehicle control groups and behavior are recorded over a 60-minute period and the results were analyzed. For statistical analysis, measurements were sampled in 5 min bins at the 5-10, 15-20, 25-30, 35-40, 45-50 and 55-60 min time intervals. The scratching response/frequency is defined based on well-established observations. Data was compared with that of rimonabant (i.p). The vehicle control group (vehicle (i.v.)) were included accordingly.

Reversal of CB1 SPC Agonist Induced Neurotoxicity

The test group (male CD-1 mice, n=8) received a "suprapharmacological" dose of JWH-018 (18 mg/kg, i.p.) followed by an optimal dose of a compound of Formula I-XI, i.v. As positive controls, mice were administered JWH-018 (18 mg/kg, i.p.). The positive control group and test group mice were immediately returned to their home cages and neurological changes comprising of convulsions and tremors are recorded for a period of 30 min and then analyzed. An animal is said to be convulsing "if the animal lies prostrate on its back and rocks from side to side in a seeming effort to right itself occasionally rolling over (overshooting) and continuing to rock again". An animal is said to displaying tremors "if the animal has involuntary, purposeless, oscillatory movements which results from the alternate contraction of opposing muscle groups".

Evaluation of Antagonist-Precipitated Withdrawal

For withdrawal experiments, the test group (male CD-1 mice, n=8) received JWH-018 (3 mg/kg, i.p.) once daily. On 5th day 90 min post agonist injection, animals were treated with either rimonabant, 10 mg/kg administered through intra-peritoneal (i.p.) route of administration or with a compound of Formula I-XI, 10 mg/kg administered i.v. Following rimonabant or with a compound of Formula I-XI administration, animals were placed singly in observational chambers for recording the precipitated withdrawal signs. Animals are recorded for headshakes (wet dog shakes) or paw tremors, behaviors that are displayed by animals experiencing precipitated cannabinoid withdrawal. Observational chambers consisted of clear glass jar (radius 4.25 cm, height 16 cm) which are sealed with perforated plastic covers for ventilation and air circulation. All the animals were recorded for 60 mins and the recording are done using JVC Everio™ digital cameras. Animals were scored using OD LOG™ software for somatic withdrawal signs by a trained experimenter who will be blinded to the treatment conditions.

The invention claimed is:

1. A method of treating acute cannabinoid overdose symptoms in an individual, comprising administering to the individual a compound of Formula II, a pharmaceutically acceptable salt, solvate, hydrate, polymorph, enantiomer, diastereomer, geometric isomer, racemate, tautomer, rotamer, atropisomer, isotopic variation, or N-oxide thereof:

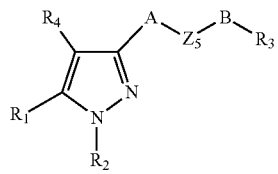

wherein:
A is a direct bond
Z5 is C(=O),
B is N($R_6$),
$R_6$ is hydrogen, —OH, alkyl;
R1 is —$(CH_2)_n$-Z;
n is an integer from 0 to 7;
Z is selected from the group consisting of

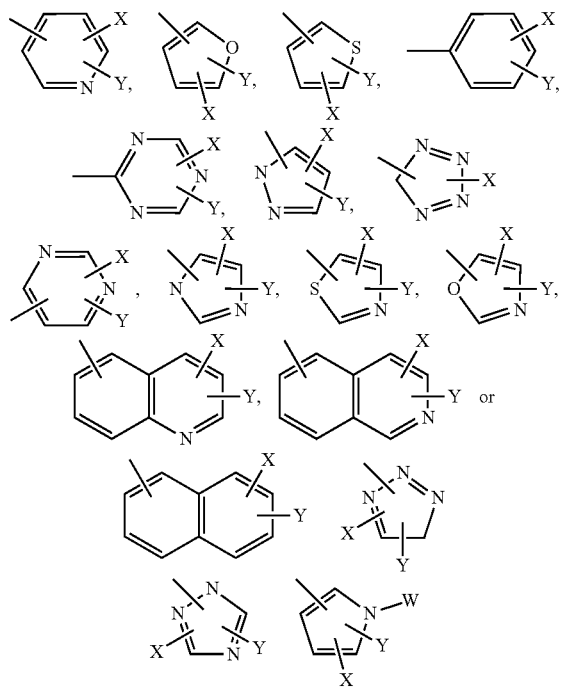

wherein each of X and Y is independently selected from ester, —C(=O)N—O-$X_1$, $SC(CH_3)_2COOX_8$, $OC(CH_3)_2COOX_8$, $C(CH_3)_2COOX_8$;
each of $X_1$, $X_2$, and $X_3$ is independently H or alkyl, alkylamino, di-alkylamino, ammonium salt, quaternary ammonium salt, or a heterocyclic ring having 4 to 7 ring members and optionally one additional heteroatom selected from O, N and S;
$X_1$ and $X_2$ together form part of a heterocyclic ring having 4 to 7 ring members and optionally one additional heteroatom selected from O, N and S, or
$X_1$ and $X_2$ together form part of an imide ring having 5 to 6 members,
$X_3$ is selected from the group consisting of H, alkyl, aryl, $NO_2$, $(CH_2)_mCN$, hydroxyloweralkyl, or alkyl-$NX_1X_2$, $X_8$ is selected from the group consisting of H, alkyl, carbocyclic ring, heterocyclic ring, aromatic ring, heteroaromatic ring, or -$CX_9$=$CHX_{10}$, wherein
$X_9$ and $X_{10}$ are each independently H or alkyl;
wherein m is an integer from 0 to 7;
R1 is -T-$(CH_2)_n$-Z;
n is an integer from 0 to 7;
T is selected from the group consisting of an aromatic ring having 5 to 8 carbon atoms as ring members, a heteroaromatic ring having 5 to 8 ring members,
Z is selected from the group consisting of ester, —C(=O)N—O-$X_1$, $SC(CH_3)_2COOX_8$, $OC(CH_3)_2COOX_8$, $C(CH_3)_2COOX_8$, $COOX_3$;
each of $X_1$, $X_2$, and $X_3$ is independently H or alkyl, alkylamino, di-alkylamino, ammonium salt, quaternary ammonium salt, and a heterocyclic ring having 4 to 7 ring members and optionally one additional heteroatom selected from O, N and S;
$X_1$ and $X_2$ together form part of a heterocyclic ring having 4 to 7 ring members and optionally one additional heteroatom selected from O, N and S, or
$X_1$ and $X_2$ together form part of an imide ring having 5 to 6 members,
$X_3$ is selected from the group consisting of H, alkyl, $NO_2$, NO, $(CH_2)_mCN$, hydroxyloweralkyl, and alkyl-$NX_1X_2$,
$X_8$ is selected from the group consisting of H, alkyl, carbocyclic ring, heterocyclic ring, aromatic ring, heteroaromatic ring, and -$CX_9$=$CHX_{10}$, wherein
each of $X_9$ and $X_{10}$ is independently H or alkyl;
m is an integer from 0 to 7;
-T-$(CH_2)_n$-Z;
n is an integer from 0 to 7;
T is selected from the group consisting of an aromatic ring having 5 to 8 carbon atoms as ring members, a heteroaromatic ring having 5 to 8 ring members;
Z is selected from the group consisting of

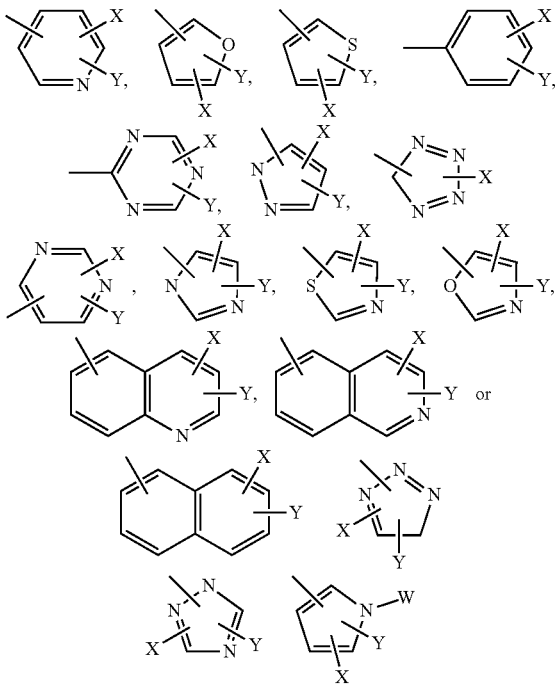

wherein each of X and Y is independently selected from —C(=O)N—O-$X_1$, SC(CH$_3$)$_2$COO$X_8$, OC(CH$_3$)$_2$COO$X_8$, C(CH$_3$)$_2$COO$X_8$;

each of $X_1$, $X_2$, and $X_3$ is independently selected from H or alkyl, alkylamino, di-alkylamino, ammonium salt, quaternary ammonium salt, and a heterocyclic ring having 4 to 7 ring members and optionally one additional heteroatom selected from O, N and S $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, NO$_2$, (CH$_2$)$_m$CN, hydroxyloweralkyl, and alkyl-N$X_1X_2$, $X_8$ is selected from the group consisting of H, alkyl, carbocyclic ring, heterocyclic ring, aromatic ring, heteroaromatic ring, and -C$X_9$=CH$X_{10}$ wherein each of $X_9$ and $X_{10}$ is independently H or alkyl;

m is an integer from 0 to 7;

R1 is -T-(CH$_2$)$_m$-$Q_1$-(CH$_2$)$_n$-Z;

each of m and n is independently an integer from 0 to 7;

T is selected from the group consisting of an aromatic ring having 5 to 8 carbon atoms as ring members, a heteroaromatic ring having 5 to 8 ring members;

$Q_1$ is selected from the group consisting of NH, O, S, CH=CH, C≡C, CO, SO$_2$ and OSO$_2$;

Z is selected from the group consisting of —C(=O)N—O-$X_1$, SC(CH$_3$)$_2$COO$X_8$, OC(CH$_3$)$_2$COO$X_8$, C(CH$_3$)$_2$COO$X_8$, COO$X_3$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, NO$_2$, NO, (CH$_2$)$_m$CN, hydroxyloweralkyl, and alkyl-N$X_1X_2$, $X_8$ is selected from the group consisting of H, alkyl, carbocyclic ring, heterocyclic ring, aromatic ring, heteroaromatic ring, and -C$X_9$=CH$X_{10}$, wherein each of $X_9$ and $X_{10}$ is independently H or alkyl;

m is an integer from 0 to 7;

R1 is -T-(CH$_2$)$_m$-$Q_1$-(CH$_2$)$_n$-Z;

each of m and n is independently an integer from 0 to 7;

T is selected from the group consisting an aromatic ring having 5 to 8 carbon atoms as ring members, a heteroaromatic ring having 5 to 8 ring members;

$Q_1$ is selected from the group consisting of NH, O, S, CH=CH, C≡C, CO, SO$_2$ and OSO$_2$;

Z is selected from the group consisting of

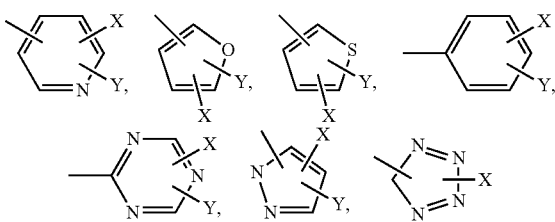

-continued

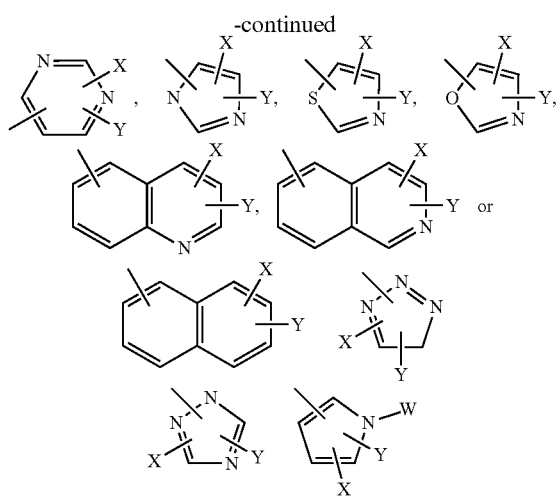

wherein each of X and Y is independently selected from ester, —C(=O)N—O-$X_1$, SC(CH$_3$)$_2$COO$X_8$, OC(CH$_3$)$_2$COO$X_8$, C(CH$_3$)$_2$COO$X_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, NO$_2$, (CH$_2$)$_m$CN, hydroxyloweralkyl, and alkyl-N$X_1X_2$, R2 is —(CH$_2$)$_n$-Z;

n is an integer from 0 to 7;

Z is selected from the group consisting of H, halogen, ester, CF$_3$, CF$_2$H, N$_3$, NCS, CN, NO$_2$, N$X_1X_2$, O$X_3$, S$X_3$, OAc, OSO$_2X_3$, —C(=O)N—O-$X_1$, —C(=N—O-$X_1$)$X_2$, O-acyl, S-acyl, SO$_2$-alkyl, SO-alkyl, SC(CH$_3$)$_2$COO$X_8$, OC(CH$_3$)$_2$COO$X_8$, C(CH$_3$)$_2$COO$X_8$, Si(alkyl)$_3$, O-aroyl, O(CH$_2$)$_j$O$X_3$, O(CH$_2$)$_j$N$X_1X_2$, alkyl-CN, NH-acyl, NH-aroyl, CHO, C(halogen)$_3$, COO$X_3$, SO$_3$H, SO$_2$N$X_1X_2$, CON$X_1X_2$, NHC(O)O-alkyl, NHSO$_2$-alkyl, alkoxy, alkyl, alcohol, alkylmercapto, alkylamino, di-alkylamino, alkylsulfinyl or alkylsulfonyl, C$X_4X_5X_6$, —CH=CH$X_8$, and —C≡C$X_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S, or $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, aryl, NO$_2$, NO, (CH$_2$)$_m$CN, hydroxyloweralkyl, and alkyl-N$X_1X_2$, $X_4$, $X_5$, and $X_6$ are each independently selected from H, alkyl, carbocyclic ring, hydroxyloweralkyl, alkyl-OH, halogen, CN, SNO, S(SO$_2$)alkyl, N$X_1X_2$, COO$X_3$, CON$X_3$, O$X_7$, and O-alkyl-$X_7$, wherein X₇ is selected from the group consisting of H, alkyl, NO₂, NO, P(O)(OX₈)₂, PH(O)(OX₈), S(O)$_K$N(alkyl)₂, S(O)$_k$X₈, S(O)$_k$OX₈, COOX₈, CONX₈, SO₃H, and COX₈, wherein X₈ is selected from the group consisting of H, alkyl, carbocyclic ring, heterocyclic ring, aromatic ring, heteroaromatic ring, or -CX₉=CHX₁₀, wherein X₉ and X₁₀ are each independently H or alkyl;

wherein m is an integer from 0 to 7;

j is an integer from 0 to 6;

k is an integer from 0 to 2; or

R2 is —(CH₂)$_n$-Z; wherein n is an integer from 0 to 7;

Z is selected from the group consisting of carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group and a substituted benzhydryl group; and wherein the connecting point between the —(CH₂)$_n$— group and the Z group can be any available ring carbon atom or any available ring nitrogen atom; or R2 is —(CH₂)$_n$-Z, wherein n is an integer from 0 to 7;

Z is selected from the group consisting of a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —(CH₂)$_n$— group and the Z group can be any available ring carbon atom or any available ring nitrogen atom; or R2 is —(CH₂)$_n$-Z;

n is an integer from 0 to 7;

Z is selected from the group consisting of 1-, 2- or 3-pyrrolidinyl, 1-, 2-, 3- or 4-piperidinyl, 2-3- or 4-morpholinyl, 2-3- or 4-thiomorpholinyl, 1-2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group and a substituted benzhydryl group; and wherein the connecting point between the —(CH₂)$_n$— group and the Z group can be any available ring carbon atom or any available ring nitrogen atom; or R2 is —(CH₂)$_n$-Z;

n is an integer from 0 to 7;

Z is selected from the group consisting of

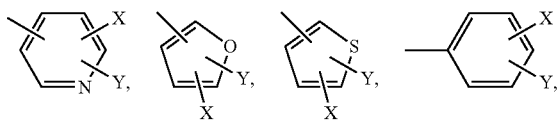

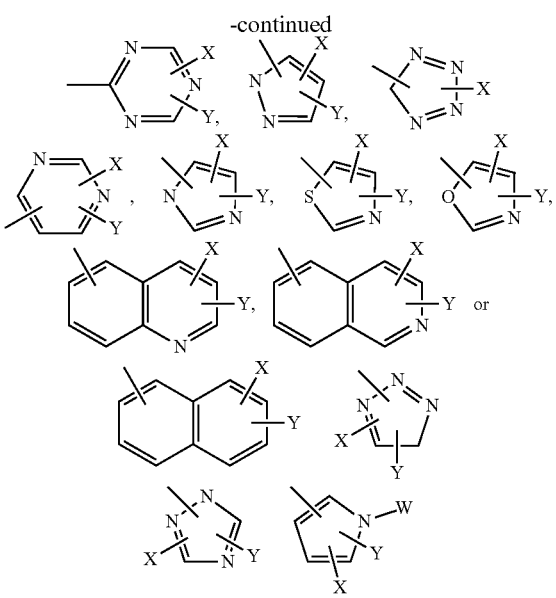

wherein each of X and Y is independently selected from H, halogen, ester, CF₃, CF₂H, N₃, NCS, CN, NO₂, NX₁X₂, —C(=O)N—O-X₁, —C(=N—O-X₁)X₂, OX₃, SX₃, OAc, OSO₂X₃, O-acyl, S-acyl, SO₂-alkyl, SO-alkyl, SC(CH₃)₂COOX₈, OC(CH₃)₂COOX₈, C(CH₃)₂COOX₈, Si(alkyl)₃, alkyl-CN, O-aroyl, O(CH₂)$_j$OX₃, O(CH₂)$_j$NX₁X₂, NH-acyl, NH-aroyl, CHO, C(halogen)₃, COOX₃, SO₃H, SO₂NX₁X₂, CONX₁X₂, NHC(O)O-alkyl, NHSO₂-alkyl, alkoxy, alkyl, alcohol, alkylmercapto alkylamino, di-alkylamino, alkylsulfinyl or alkylsulfonyl, CX₄X₅X₆, —CH=CHX₈, and —C≡CX₈;

each of X₁, X₂, and X₃ is independently H or alkyl, alkylamino, di-alkylamino, ammonium salt, quaternary ammonium salt, or a heterocyclic ring having 4 to 7 ring members and optionally one additional heteroatom selected from O, N and S;

X₁ and X₂ together form part of a heterocyclic ring having 4 to 7 ring members and optionally one additional heteroatom selected from O, N and S, or X₁ and X₂ together form part of an imide ring having 5 to 6 members, X₃ is selected from the group consisting of H, alkyl, aryl, NO₂, (CH₂)$_m$CN, hydroxyloweralkyl, or alkyl-NX₁X₂, X₄, X₅, and X₆ are each independently selected from H, alkyl, carbocyclic ring, hydroxyloweralkyl, alkyl-OH, halogen, CN, SNO, S(SO₂)alkyl, NX₁X₂, COOX₃, CONX₃, OX₇, and O-alkyl-X₇; wherein X₇ is selected from the group consisting of H, alkyl, NO₂, NO, P(O)(OX₈)₂, PH(O)(OX₈), S(O)$_K$N(alkyl)₂, S(O)$_k$X₈, S(O)$_k$OX₈, COOX₈, CONX₈, SO₃H, and COX₈, wherein X₈ is selected from the group consisting of H, alkyl, carbocyclic ring, heterocyclic ring, aromatic ring, heteroaromatic ring, or -CX₉=CHX₁₀, wherein X₉ and X₁₀ are each independently H or alkyl;

wherein m is an integer from 0 to 7;

j is an integer from 0 to 6, or k is an integer from 0 to 2; or

R2 is —(CH₂)$_n$-Z;

n is an integer from 0 to 7;

Z is selected from the group consisting of a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms; or R2 is $-(CH_2)_n$-Z;

n is an integer from 0 to 7;

Z is selected from the group consisting of an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 3 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members; or R2 is $-(CH_2)_m$-$Q_1$-$(CH_2)_n$-Z;

$Q_1$ is selected from the group consisting of NH, O, S, $-CH=CH-$, $-C\equiv C-$, $-CO$, $SO_2$ and $OSO_2$;

m is an integer from 1 to 7;

n is an integer from 0 to 7;

Z is selected from the group consisting of H, halogen, ester, $CF_3$, $CF_2H$, $N_3$, NCS, CN, $NO_2$, $NX_1X_2$, $OX_3$, $SX_3$, OAc, $OSO_2X_3$, $-C(=O)N-O-X_1$, $-C(=N-O-X_1)X_2$, O-acyl, S-acyl, $SO_2$-alkyl, SO-alkyl, $SC(CH_3)_2COOX_8$, $OC(CH_3)_2COOX_8$ $C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, and $-C\equiv CX_8$;

each of $X_1$, $X_2$, and $X_3$ is independently selected from H or alkyl, alkylamino, di-alkylamino, ammonium salt, quaternary ammonium salt, and a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members;

$X_3$ is selected from the group consisting of H, alkyl, $NO_2$, NO, $(CH_2)_mCN$, hydroxyloweralkyl, and alkyl-$NX_1X_2$;

each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_kX_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9=CHX_{10}$, wherein each of $X_9$ and $X_{10}$ is independently H or alkyl;

m is an integer from 0 to 7;

j is an integer from 0 to 6; and k is an integer from 0 to 2; or

R2 is -$Q_2$-$(CH_2)_n$-Z;

$Q_2$ is optionally present and if present is selected from the group consisting of $-CH_2-NH$, $-CH_2-O$, $-CH_2-S$, $-CH_2-SO_2$ and $-CH_2-OSO_2$;

n is an integer from 0 to 7;

Z is selected from the group consisting of H, halogen, ester, $CF_3$, $CF_2H$, $N_3$, NCS, CN, $NO_2$, $NX_1X_2$, $OX_3$, $SX_3$, OAc, $OSO_2X_3$, $-C(=O)N-O-X_1$, $-C(=N-O-X_1)X_2$, O-acyl, S-acyl, $SO_2$-alkyl, SO-alkyl, $SC(CH_3)_2COOX_8$, $OC(CH_3)_2COOX_8$, $C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, and $-C\equiv CX_8$;

each of $X_1$, $X_2$, and $X_3$ is independently selected from H or alkyl, alkylamino, di-alkylamino, ammonium salt, quaternary ammonium salt, and a heterocyclic ring having 4 to 7 ring members and optionally one additional heteroatom selected from O, N and S; or $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, NO, $(CH_2)_mCN$, hydroxyloweralkyl, and alkyl-$NX_1X_2$, each of $X_4$, $X_5$, and $X_6$ is independently selected from the group consisting of H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_kX_8$, $S(O)_kOX_8$, $COOX_8$, $CONX_8$, $SO_3H$ and $COX_8$, wherein $X_8$ is selected from the group consisting of H, alkyl, carbocyclic ring, heterocyclic ring, aromatic ring, heteroaromatic ring, and -$CX_9=CHX_{10}$, wherein each of $X_9$ and $X_{10}$ is independently H or alkyl;

m is an integer from 0 to 7;

j is an integer from 0 to 6; and k is an integer from 0 to 2; or

R2 is $-(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7; and

Z is selected from the group consisting of a bicyclic ring, a heterobicyclic ring, a tricyclic ring, a heterotricyclic ring, a polycyclic ring and a heteropolycyclic ring;

R2 is $-(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7;

Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members; a bicyclic ring, a heterobicyclic ring, a tricyclic ring, a heterotricyclic ring, a polycyclic ring, a heteropolycyclic ring or any above group substituted on at least one available ring atom by an alkyl group or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 is —$(CH_2)_m$-$Q_1$-$(CH_2)_n$-Z;

$Q_1$ is selected from the group consisting of N, O, S, CH=CH, C≡C, CO, $SO_2$ and $OSO_2$;

m is an integer from 1 to 7;

n is an integer from 0 to 7; and

Z is selected from the group consisting of a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$ — group and the Z group can be any available ring carbon atom or any available ring nitrogen atom; or R2 is —$(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7; and

Z is selected from the group consisting of 1-, 2- or 3-pyrrolidinyl, 1-, 2-, 3- or 4-piperidinyl, 2-3- or 4-morpholinyl, 2-3- or 4-thiomorpholinyl, 1-2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group and a substituted benzhydryl group; and wherein the connecting point between the —$(CH_2)_n$ — group and the Z group can be any available ring carbon atom or any available ring nitrogen atom; or R2 is —$(CH_2)_m$-$Q_1$-$(CH_2)_n$-Z;

$Q_1$ is selected from the group consisting of N, O, S, CH=CH, C≡C, CO, $SO_2$ and $OSO_2$;

m is an integer from 1 to 7;

n is an integer from 0 to 7;

Z is selected from the group consisting of

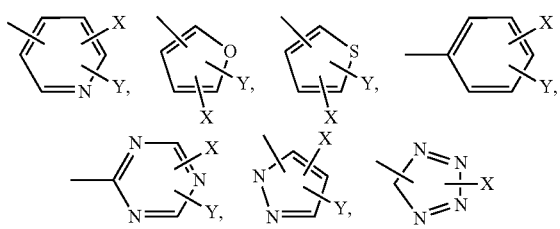

-continued

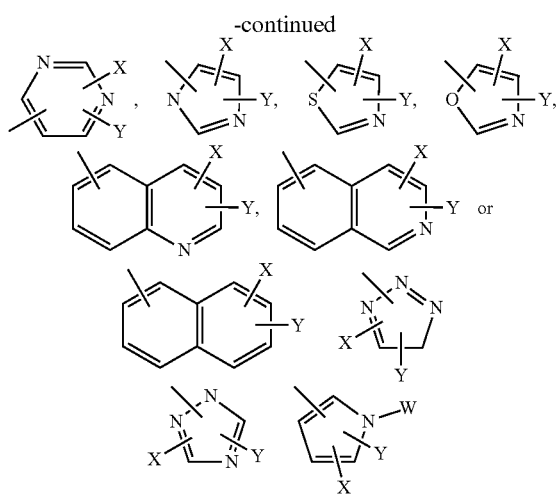

wherein each of X and Y is independently selected from H, halogen, ester, $CF_3$, $CF_2H$, $N_3$, NCS, CN, $NO_2$, —C(=O)N—O-$X_1$, —C(=N—O-$X_1$)$X_2$, $NX_1X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, and O-alkyl-$X_7$, wherein $X_7$ is selected from the group consisting of H, alkyl, $NO_2$, NO, P(O)(O$X_8$)$_2$, PH(O)(O$X_8$), $S(O)_kN(alkyl)_2$, $S(O)_kX_8$, $S(O)_kOX_8$, $COOX_8$, $CONX_8$, $SO_3H$ and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein $X_9$ and $X_{10}$ are each independently H or alkyl;

m is an integer from 0 to 7;

j is an integer from 0 to 6;

k is an integer from 0 to 2; and

R2 is —$(CH_2)_m$-$Q_1$-$(CH_2)_n$-Z;

$Q_1$ is selected from NH, O, S, CH=CH, C C, CO, $SO_2$ and $OSO_2$;

m is an integer from 1 to 7;

n is an integer from 0 to 7; and

Z is selected from the group consisting of an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 4 independently selected heteroatoms as ring members fused to an unsaturated ring having 6 or 7 ring atoms and 0 to 4 independently selected heteroatoms as ring members;

R2 is $-(CH_2)_m-Q_1-(CH_2)_n-Z$;

$Q_1$ is selected from the group consisting of NH, O, S, CH=CH, C≡C, CO, $SO_2$ and $OSO_2$;

m is an integer from 1 to 7;

n is an integer from 0 to 7; and

Z is selected from the group consisting of

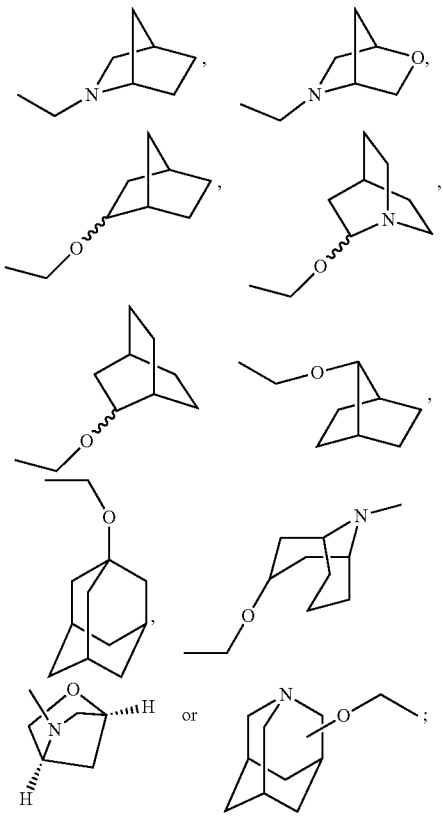

or

R2 is $-T-(CH_2)_n-Z$;

n is an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

Z is selected from the group consisting of H, halogen, ester, $CF_3$, $CF_2H$, $N_3$, NCS, CN, $NO_2$, $NX_1X_2$, $OX_3$, $SX_3$, OAc, $OSO_2X_3$, $-C(=O)N-O-X_1$, $-C(=N-O-X_1)X_2$, O-acyl, S-acyl, $SO_2$-alkyl, SO-alkyl, $SC(CH_3)_2COOX_8$, $OC(CH_3)_2COOX_8C(CH_3)_2COOX_8$, $Si(alkyl)_3$, O-aroyl, $O(CH_2)_jOX_3$, $O(CH_2)_jNX_1X_2$, alkyl-CN, NH-acyl, NH-aroyl, CHO, $C(halogen)_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, $-CH=CHX_8$, and $-C≡CX_8$;

each of $X_1$, $X_2$, and $X_3$ is independently H or alkyl, alkylamino, di-alkylamino, ammonium salt, quaternary ammonium salt, and a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, NO, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_kX_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9=CHX_{10}$, wherein each of $X_9$ and $X_{10}$ is independently H or alkyl;

m is an integer from 0 to 7;

j is an integer from 0 to 6; and k is an integer from 0 to 2; or

R2 is $-T-(CH_2)_n-Z$;

n is an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring; and Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the $-(CH_2)_n-$ group and the Z group can be any available ring carbon atom or any available ring nitrogen atom;

R2 is $-T-(CH_2)_n-Z$;

n is an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring or a heteropolycyclic ring; and Z is selected from the group consisting of 1-, 2- or 3-pyrrolidinyl, 1-, 2-, 3- or 4-piperidinyl, 2-3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 is -T-$(CH_2)_n$-Z;

n is an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring or a heteropolycyclic ring;

Z is selected from the group consisting of

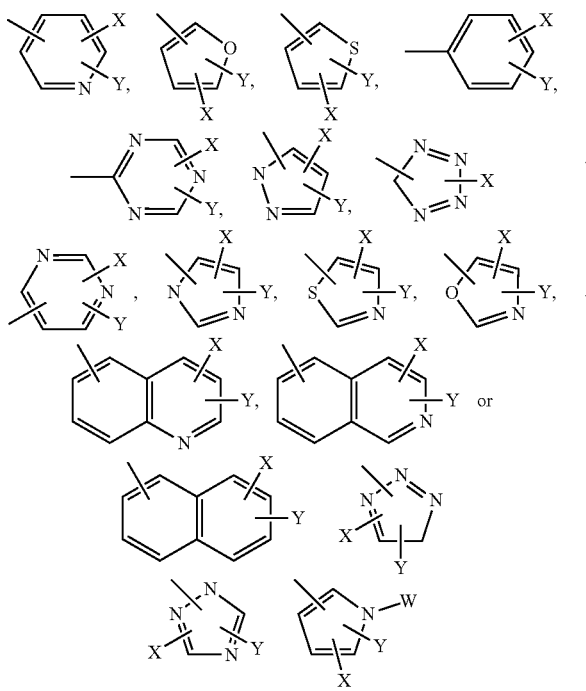

wherein each of X and Y is independently selected from H, halogen, ester, $CF_3$, $CF_2H$, $N_3$, NCS, CN, $NO_2$, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, SC$(CH_3)_2$COO$X_8$, OC$(CH_3)_2$COO$X_8$, C$(CH_3)_2$COO$X_8$, Si(alkyl)$_3$, alkyl-CN, O-aroyl, O$(CH_2)_j$O$X_3$, O$(CH_2)_j$N$X_1X_2$, NH-acyl, NH-aroyl, CHO, C(halogen)$_3$, COO$X_3$, $SO_3H$, $SO_2NX_1X_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$;

each of $X_1$, $X_2$, and $X_3$ is independently selected from H or alkyl, alkylamino, di-alkylamino, ammonium salt, quaternary ammonium salt, and a heterocyclic ring having 4 to 7 ring members and optionally one additional heteroatom selected from O, N and S $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_m$CN, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$ wherein $X_7$ is selected from the group consisting of H, alkyl, $NO_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H and COX$_8$, wherein $X_8$ is selected from the group consisting of H, alkyl, carbocyclic ring, heterocyclic ring, aromatic ring, heteroaromatic ring, and -CX$_9$=CHX$_{10}$ wherein each of $X_9$ and $X_{10}$ is independently H or alkyl;

m is an integer from 0 to 7;

j is an integer from 0 to 6;

k is an integer from 0 to 2; or

R2 is -T-$(CH_2)_n$-Z;

n is an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

Z is selected from the group consisting of an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R2 is -T-$(CH_2)_m$-$Q_1$-$(CH_2)_n$-Z;

each of m and n is independently an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring or a heteropolycyclic ring;

$Q_1$ is selected from the group consisting of NH, O, S, CH=CH, C≡C, CO, $SO_2$ and $OSO_2$;

Z is selected from the group consisting of H, halogen, ester, $CF_3$, $CF_2H$, $N_3$, NCS, CN, $NO_2$, $NX_1X_2$, $OX_3$, $SX_3$, OAc, $OSO_2X_3$, —C(=O)N—O-$X_1$, —C(=N—O-$X_1$)$X_2$, O-acyl, S-acyl, $SO_2$-alkyl, SO-alkyl, $SC(CH_3)_2COOX_8$, $OC(CH_3)_2COOX_8C(CH_3)_2COOX_8$, Si(alkyl)$_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$ and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, NO, $(CH_2)_mCN$, hydroxyloweralkyl, and alkyl-$NX_1X_2$;

each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_kN(alkyl)_2$, $S(O)_k X_8$, $S(O)_kOX_8$, $COOX_8$, $CONX_8$, $SO_3H$ and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6; and k is an integer from 0 to 2; or

R2 is -T-$(CH_2)_m$-$Q_1$-$(CH_2)_n$-Z;

each of m and n is independently an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

$Q_1$ is selected from the group consisting of NH, O, S, CH=CH, C≡C, CO, $SO_2$ and $OSO_2$;

Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 is -T-$(CH_2)_m$-$Q_1$-$(CH_2)_n$-Z;

each of m and n is independently an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

$Q_1$ is selected from the group consisting of NH, O, S, CH=CH, C≡C, CO, $SO_2$ and $OSO_2$;

Z is selected from the group consisting of 1-2- or 3-pyrrolidinyl, 1-, 2-, 3- or 4-piperidinyl, 2-, 3- or 4-morpholinyl, 2-, 3- or 4-thiomorpholinyl, 1-2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or each of R1 and R2 is independently -T-$(CH_2)_m$-$Q_1$-$(CH_2)_n$-Z;

each of m and n is independently an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

$Q_1$ is selected from the group consisting of NH, O, S, CH=CH, C≡C, CO, $SO_2$ and $OSO_2$;

Z is selected from the group consisting of

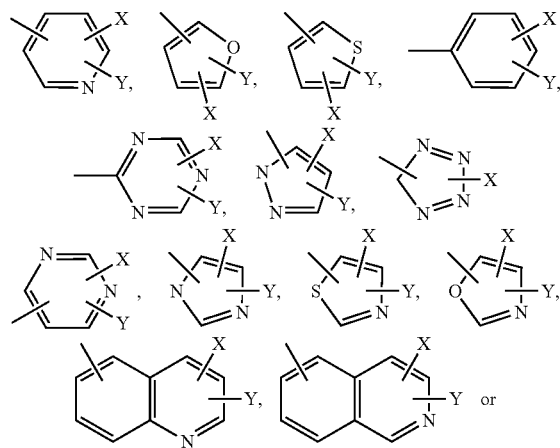

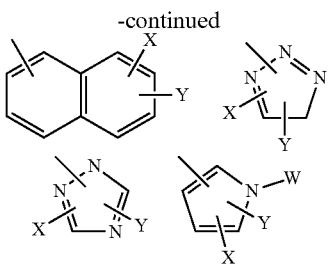

wherein each of X and Y is independently selected from H, halogen, ester, $CF_3$, $CF_2H$, $N_3$, NCS, CN, $NO_2$, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$ and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, S($SO_2$)alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6;

k is an integer from 0 to 2; or

R2 is -T-$(CH_2)_m$-$Q_1$-$(CH_2)_n$-Z;

each of m and n is independently an integer from 0 to 7;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

$Q_1$ is selected from the group consisting of NH, O, S, CH=CH, C≡C, CO, $SO_2$ and $OSO_2$; and Z is selected from the group consisting of an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R2 is -T-$(CH_2)_m$-$Q_1$-$(CH_2)_n$-Z;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

each of m and n is independently an integer from 0 to 7;

$Q_1$ is selected from the group consisting of NH, O, S, CH=CH, C≡C, CO, $SO_2$ and $OSO_2$;

Z is

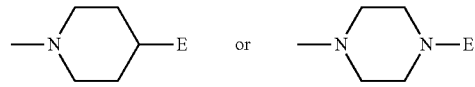

wherein E is selected from the group consisting of a C1 to C4, linear or branched alkyl group, a phenyl group, a substituted phenyl group, a benzyl group or a substituted benzyl group; or R2 is -T-$(CH_2)_m$-$Q_1$-$(CH_2)_n$-Z;

T is selected from the group consisting of a carbocyclic ring having 3 to 8 ring members, an unsaturated ring having 3 to 8 carbon atoms as ring members, an aromatic ring having 5 to 8 carbon atoms as ring members, a heterocyclic ring having 3 to 8 ring members, a heteroaromatic ring having 5 to 8 ring members, a bicyclic ring, a heterobicyclic ring, a tricyclic ring, a heterotricyclic ring, a polycyclic ring and a heteropolycyclic ring;

each of m and n is independently an integer from 0 to 7;

$Q_1$ is selected from the group consisting of NH, O, S, CH=CH, C≡C, CO, $SO_2$ and $OSO_2$;

Z is selected from the group consisting of

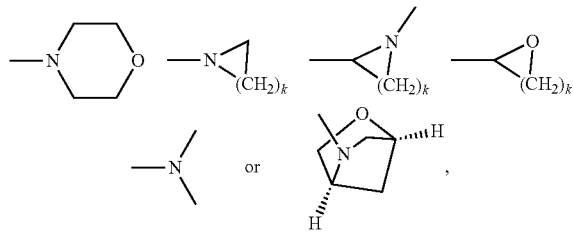

wherein k is an integer from 1 to 5;

each of $A_1$ and $A_2$ is independently selected from a C1 to C4 alkyl group, a phenyl group or a substituted phenyl group;

R3 is selected from the group consisting of a carbocyclic ring having 4 to 7 members, a heterocyclic ring having 4 to 7 members, an aromatic ring having 5 to 7 ring members, a heteroaromatic ring having 5 to 7 members, a bicyclic ring, a heterobicyclic ring, a tricyclic ring, a heterotricyclic ring, a polycyclic ring and a heteropolycyclic ring; or R3 is

wherein G is selected from the group consisting of CH, C(CH$_3$), C(CN) and N;
each of L, K and J is independently selected from (CH$_2$)$_n$, (CH$_3$)$_2$, C═O, O, —CHOH, C(CH$_3$)OM$_1$, C(CH$_2$)$_n$(X)Y, NM$_1$, SO$_2$SO and S;
n is an integer from 0 to 7;
M$_1$ is H, alkyl or C(O)M$_2$, wherein
M$_2$ is selected from the group consisting of H, alkyl, NM$_3$M$_4$, and OM$_5$, and
each of M$_3$, M$_4$ and M$_5$ is independently selected from H, OH and alkyl, and
each of X and Y is independently selected from H, halogen, ester, CF$_3$, CF$_2$H, N$_3$, NCS, CN, NO$_2$, NX$_1$X$_2$, —C(═O)N—O-X$_1$, —C(═N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH═CHX$_8$ and —C≡CX$_8$;
each of X$_1$, X$_2$, and X$_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;
X$_1$ and X$_2$ together form part of a heterocyclic ring having 4 to 7 ring members and optionally one additional heteroatom selected from O, N and S, or
X$_1$ and X$_2$ together form part of an imide ring having 5 to 6 members,
X$_3$ is selected from the group consisting of H, alkyl, NO$_2$, (CH$_2$)$_m$CN, hydroxyloweralkyl, and alkyl-NX$_1$X$_2$,
each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein
X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein
X$_8$ is selected from the group consisting of H, alkyl, carbocyclic ring, heterocyclic ring, aromatic ring, heteroaromatic ring, and -CX$_9$═CHX$_{10}$, wherein
each of X$_9$ and X$_{10}$ is independently H or alkyl;
m is an integer from 0 to 7;
j is an integer from 0 to 6; and
k is an integer from 0 to 2; or
R3 is

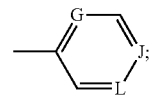

wherein each of G, L and J is independently CH or N; or
R3 is selected from the group consisting of

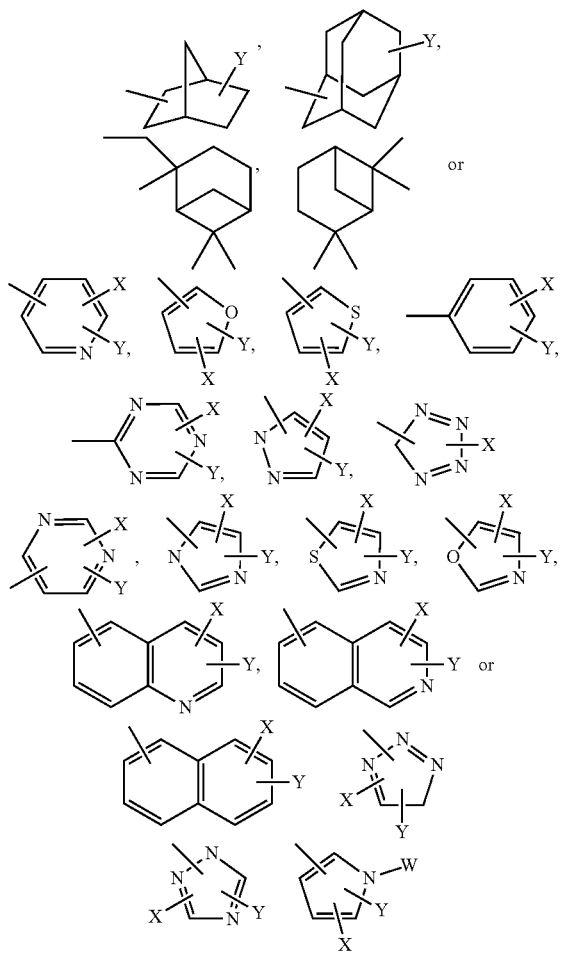

wherein each of X and Y is independently selected from H, halogen, ester, CF$_3$, CF$_2$H, N$_3$, NCS, CN, NO$_2$, NX$_1$X$_2$, —C(═O)N—O-X$_1$, —C(═N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, and —CH═CHX$_8$ and —C≡CX$_8$;
each of X$_1$, X$_2$, and X$_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;
X$_1$ and X$_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_m CN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_kN(\text{alkyl})_2$, $S(O)_k X_8$, $S(O)_k OX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6;

k is an integer from 0 to 2;

R3 is selected from the group consisting of a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, a heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms;

R4 is selected from the group consisting of H, halogen, ester, $CF_3$, $CF_2H$, $N_3$, NCS, CN, $NO_2$, phenyl, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_m CN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_kN(\text{alkyl})_2$, $S(O)_k X_8$, $S(O)_k OX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6; and k is an integer from 0 to 2; or

R4 is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a tricyclic ring, a heterotricyclic ring, a polycyclic ring or a heteropolycyclic ring; or R4 is selected from the group consisting of

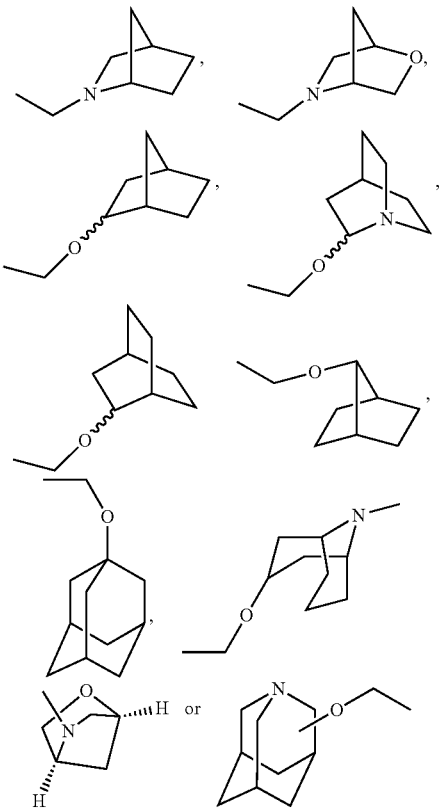

R4 is —$(CH_2)_d$-Z;

d is an integer from 1 to 6;

Z is selected from the group consisting of H, ester, halogen, $CF_3$, $CF_2H$, $N_3$, NCS, CN, $NO_2$, phenyl, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)NX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S; or $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_k X_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6; and k is an integer from 0 to 2; or

R4 is —$CH_2OH$ or -$CH_2O$alkyl; or

R4 is —$(CH_2)_d$-Z;

d is an integer from 1 to 6; and

Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_d$— group and the Z group can be any available ring carbon atom or any available ring nitrogen atom; or R4 is —$(CH_2)_d$-Z;

d is an integer from 1 to 6; and

Z is selected from the group consisting of 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_d$ — group and the Z group can be any available ring carbon atom or any available ring nitrogen atom; or R4 is —$(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7;

Z is selected from the group consisting of H, halogen, ester, $CF_3$, $CF_2H$, $N_3$, NCS, CN, $NO_2$, phenyl, $NX_1X_2$, —C(=N—O-$X_1$) $X_1$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2 COOX_8$, $Si(alkyl)_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=$CHX_8$, and —C≡$CX_8$;

each of $X_1$, $X_2$, and $X_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S; or $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_k X_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$=$CHX_{10}$, wherein each of $X_9$ and $X_{10}$ is independently H or alkyl;

m is an integer from 0 to 7;

j is an integer from 0 to 6; and k is an integer from 0 to 2; or

R4 is —$(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7; and

Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members; a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R4 is —$(CH_2)_m$-$Q_1$-$(CH_2)_n$-Z;

$Q_1$ is selected from the group consisting of NH, O, S, CH=CH, C≡C, CO, $SO_2$ and $OSO_2$;

m is an integer from 1 to 7;

n is an integer from 0 to 7;

Z is selected from the group consisting of 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R4 is —(CH$_2$)$_m$-Q$_1$-(CH$_2$)$_n$-Z;

Q$_1$ is selected from the group consisting of NH, O, S, CH=CH, C≡C, CO, SO$_2$ and OSO$_2$;

m is an integer from 1 to 7;

n is an integer from 0 to 7;

Z is selected from the group consisting of

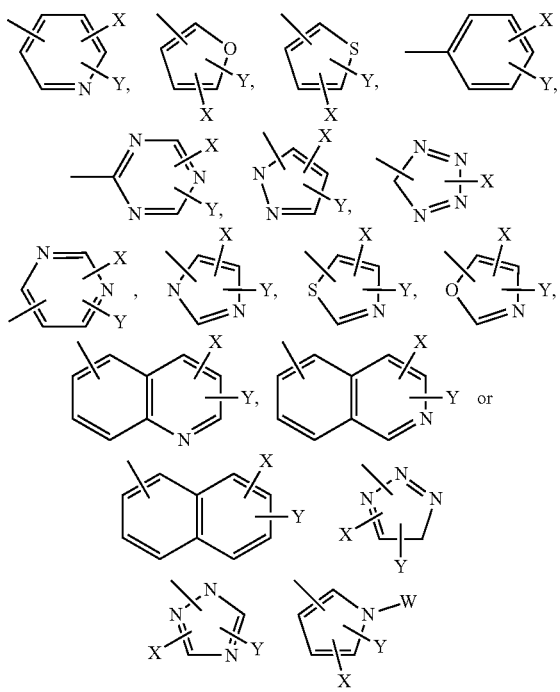

wherein each of X and Y is independently selected from ester, CF$_3$, CF$_2$H, N$_3$, NCS, CN, NO$_2$, NX$_1$X$_2$, —C(=O)N—O-X$_1$, —C(=N—O-X$_1$) X$_1$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl alkoxy, alkyl, alcohol, alkylmercapto, alkylamino, di-alkylamino, alkylsulfinyl or alkylsulfonyl, CX$_4$X$_5$X$_6$, —CH=CHX$_8$, and —C≡CX$_8$;

each of X$_1$, X$_2$, and X$_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

X$_1$ and X$_2$ together form part of a heterocyclic ring having 4 to 7 ring members and optionally one additional heteroatom selected from O, N and S, or X$_1$ and X$_2$ together form part of an imide ring having 5 to 6 members, X$_3$ is selected from the group consisting of H, alkyl, NO$_2$, (CH$_2$)$_m$CN, hydroxyloweralkyl, and alkyl-NX$_1$X$_2$, each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6; and k is an integer from 0 to 2.

2. The method of claim 1, wherein

R2 is —(CH$_2$)$_n$-Z;

n is 0;

Z is selected from the group consisting of an aromatic ring having 5 to 7 ring members, a heteroaromatic ring having 5 to 7 ring members; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group and a substituted benzhydryl group; and wherein the connecting point between the —(CH$_2$)$_n$— group and the Z group can be any available ring carbon atom or any available ring nitrogen atom; or R2 is —(CH$_2$)$_n$-Z, wherein n is 0;

Z is selected from the group consisting of a 6 member aromatic ring having 0 to 5 independently selected heteroatoms as ring members or a substituted 6 member aromatic ring having 0 to 5 independently selected heteroatoms; and wherein the connecting point between the —(CH$_2$)$_n$— group and the Z group can be any available ring carbon atom or any available ring nitrogen atom; or R2 is —(CH$_2$)$_n$-Z;

n is 0;

Z is selected from the group consisting of

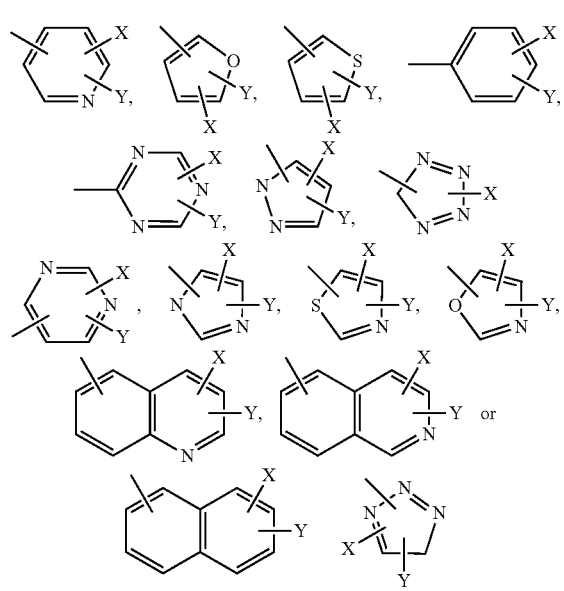

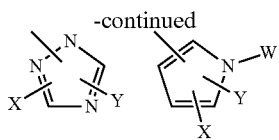

wherein each of X and Y is independently selected from H, halogen, ester, $CF_3$, $CF_2H$, $N_3$, NCS, CN, $NO_2$, $NX_1X_2$, —C(═O)N—O-$X_1$, —C(═N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH═$CHX_8$, and —C≡$CX_8$;

each of $X_1$, $X_2$, and $X_3$ is independently H or alkyl, alkylamino, di-alkylamino, ammonium salt, quaternary ammonium salt, or a heterocyclic ring having 4 to 7 ring members and optionally one additional heteroatom selected from O, N and S;

$X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, aryl, $NO_2$, $(CH_2)_mCN$, hydroxyloweralkyl, and alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$; wherein $X_7$ is selected from the group consisting of H, alkyl, $NO_2$, NO, $P(O)(OX_8)_2$, $PH(O)(OX_8)$, $S(O)_KN(alkyl)_2$, $S(O)_k X_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, or -$CX_9$═$CHX_{10}$, wherein $X_9$ and $X_{10}$ are each independently H or alkyl;

wherein m is an integer from 0 to 7;

j is an integer from 0 to 6, or k is an integer from 0 to 2; or

R2 is -T-$(CH_2)_n$-Z;

n is an integer from 0 to 7;

T is selected from the group consisting of an aromatic ring having 5 to 8 carbon atoms as ring members, a heteroaromatic ring having 5 to 8 ring members;

Z is selected from the group consisting of H, halogen, ester, $CF_3$, $CF_2H$, $N_3$, NCS, CN, $NO_2$, $NX_1X_2$, $OX_3$, $SX_3$, OAc, $OSO_2X_3$, —C(═O)N—O-$X_1$, —C(═N—O-$X_1$)$X_2$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, O-aroyl, $O(CH_2)_jOX_3$, $O(CH_2)_jNX_1X_2$, alkyl-CN, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH═$CHX_8$, and —C≡$CX_8$;

each of $X_1$, $X_2$, and $X_3$ is independently H or alkyl, alkylamino, di-alkylamino, ammonium salt, quaternary ammonium salt, and a heterocyclic ring having 4 to 7 ring members and optionally one additional heteroatom selected from O, N and S $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, $X_3$ is selected from the group consisting of H, alkyl, $NO_2$, NO, $(CH_2)_mCN$, hydroxyloweralkyl, or alkyl-$NX_1X_2$, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$, wherein $X_7$ is selected from the group consisting of H, alkyl, $NO_2$, NO, $P(O)(OX_8)_2$, $PH(O)(OX_8)$, $S(O)_KN(alkyl)_2$, $S(O)_k X_8$, $S(O)_kOX_8$, $COOX_8$, $CONX_8$, $SO_3H$, and $COX_8$, wherein $X_8$ is selected from the group consisting of H, alkyl, carbocyclic ring, heterocyclic ring, aromatic ring, heteroaromatic ring, and -$CX_9$═$CHX_{10}$, wherein $X_9$ and $X_{10}$ are each independently H or alkyl;

m is an integer from 0 to 7;

j is an integer from 0 to 6; and k is an integer from 0 to 2; or

R2 is -T-$(CH_2)_n$-Z;

n is an integer from 0 to 7;

T is selected from the group consisting of an aromatic ring having 5 to 8 carbon atoms as ring members, a heteroaromatic ring having 5 to 8 ring members; and Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom;

R2 is -T-$(CH_2)_n$-Z;

n is an integer from 0 to 7;

T is selected from the group consisting of an aromatic ring having 5 to 8 carbon atoms as ring members, a heteroaromatic ring having 5 to 8 ring members; and Z is selected from the group consisting of 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom; or R2 is -T-$(CH_2)_n$-Z;

n is an integer from 0 to 7;

T is selected from the group consisting of an aromatic ring having 5 to 8 carbon atoms as ring members, a heteroaromatic ring having 5 to 8 ring members;

Z is selected from the group consisting of

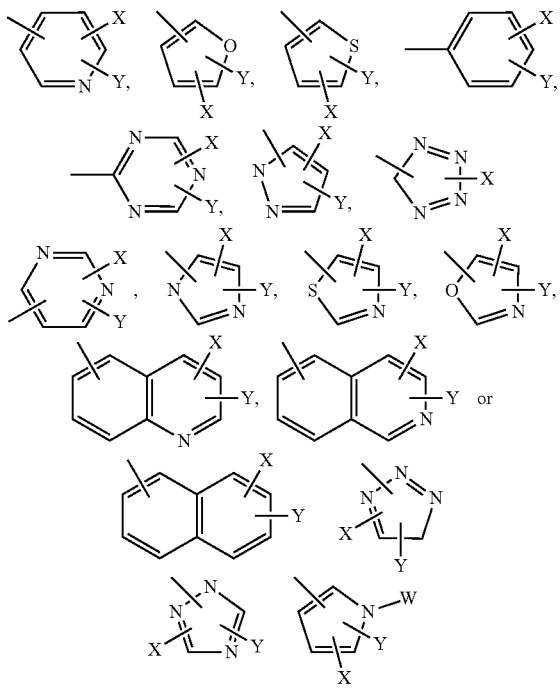

wherein X and Y are each independently selected from H, halogen, ester, CF$_3$, CF$_2$H, N$_3$, NCS, CN, NO$_2$, NX$_1$X$_2$, —C(=O)N—O—X$_1$, —C(=N—O—X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$;

each of X$_1$, X$_2$, and X$_3$ is independently selected from H or alkyl, alkylamino, di-alkylamino, ammonium salt, quaternary ammonium salt, and a heterocyclic ring having 4 to 7 ring members and optionally one additional heteroatom selected from O, N and S;

X$_1$ and X$_2$ together form part of a heterocyclic ring having 4 to 7 ring members and optionally one additional heteroatom selected from O, N and S, or X$_1$ and X$_2$ together form part of an imide ring having 5 to 6 members, X$_3$ is selected from the group consisting of H, alkyl, NO$_2$, (CH$_2$)$_m$CN, hydroxyloweralkyl, and alkyl-NX$_1$X$_2$, each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$ wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6;

k is an integer from 0 to 2; and

R2 is -T-(CH$_2$)$_n$-Z;

n is an integer from 0 to 7;

T is selected from the group consisting of an aromatic ring having 5 to 8 carbon atoms as ring members, a heteroaromatic ring having 5 to 8 ring members;

Z is selected from the group consisting of an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R2 is -T-(CH$_2$)$_m$-Q$_1$-(CH$_2$)$_n$-Z;

m and n are independently an integer from 0 to 7;

T is selected from the group consisting of an aromatic ring having 5 to 8 carbon atoms as ring members a heteroaromatic ring having 5 to 8 ring members;

Q$_1$ is selected from the group consisting of NH, O, S, CH=CH, C≡C, CO, SO$_2$ and OSO$_2$;

Z is selected from the group consisting of H, halogen, ester, CF$_3$, CF$_2$H, N$_3$, NCS, CN, NO$_2$, NX$_1$X$_2$, OX$_3$, SX$_3$, OAc, OSO$_2$X$_3$, —C(=O)N—O—X$_1$, —C(=N—O—X$_1$)X$_2$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, O-aroyl, O(CH$_2$)$_j$OX$_3$, O(CH$_2$)$_j$NX$_1$X$_2$, alkyl-CN, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$;

each of X$_1$, X$_2$, and X$_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

X$_1$ and X$_2$ together form part of a heterocyclic ring having 4 to 7 ring members and optionally one additional heteroatom selected from O, N and S; or X$_1$ and X$_2$ together form part of an imide ring having 5 to 6 members, X$_3$ is selected from the group consisting of H, alkyl, NO$_2$, NO, (CH$_2$)$_m$CN, hydroxyloweralkyl, or alkyl-NX$_1$X$_2$, each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6; and k is an integer from 0 to 2; or

R2 is -T-(CH$_2$)$_m$-Q$_1$-(CH$_2$)$_n$-Z;

each of m and n is independently an integer from 0 to 7;

T is selected from the group consisting of an aromatic ring having 5 to 8 carbon atoms as ring members, a heteroaromatic ring having 5 to 8 ring members;

Q$_1$ is selected from the group consisting of NH, O, S, CH=CH, C≡C, CO, SO$_2$ and OSO$_2$;

Z is selected from the group consisting of a carbocyclic ring having 4 to 7 ring members, a heterocyclic ring having 4 to 7 ring members, an aromatic ring having 5 to 7 ring members, a heteroaromatic ring having 5 to 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 is -T-(CH$_2$)$_m$-Q$_1$-(CH$_2$)$_n$-Z;

each of m and n is independently an integer from 0 to 7;

T is selected from the group consisting of an aromatic ring having 5 to 8 carbon atoms as ring members, a heteroaromatic ring having 5 to 8 ring members;

Q$_1$ is selected from the group consisting of NH, O, S, CH=CH, C≡C, CO, SO$_2$ and OSO$_2$;

Z is selected from the group consisting of 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom; or R2 is -T-(CH$_2$)$_m$-Q$_1$-(CH$_2$)$_n$-Z;

each of m and n is independently an integer from 0 to 7;

T is selected from the group consisting of an aromatic ring having 5 to 8 carbon atoms as ring members, a heteroaromatic ring having 5 to 8 ring members;

Q$_1$ is selected from the group consisting of NH, O, S, CH=CH, C≡C, CO, SO$_2$ and OSO$_2$;

Z is selected from the group consisting of

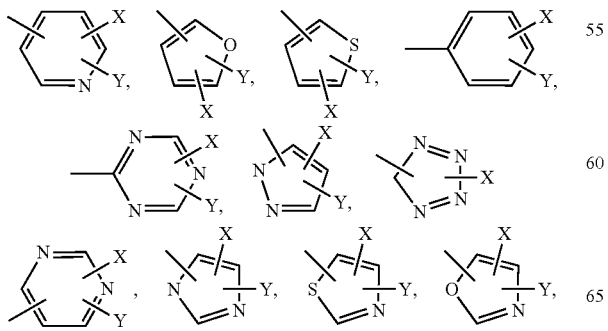

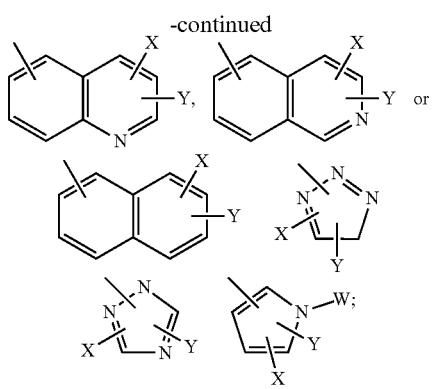

wherein each of X and Y is independently selected from H, halogen, ester, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$;

each of X$_1$, X$_2$, and X$_3$ is independently selected from H or alkyl, alkylamino, di-alkylamino, ammonium salt, quaternary ammonium salt, or a heterocyclic ring having 4 to 7 ring members and optionally one additional heteroatom selected from O, N and S;

X$_1$ and X$_2$ together form part of a heterocyclic ring having 4 to 7 ring members and optionally one additional heteroatom selected from O, N and S, or X$_1$ and X$_2$ together form part of an imide ring having 5 to 6 members, X$_3$ is selected from the group consisting of H, alkyl, NO$_2$, (CH$_2$)$_m$CN, hydroxyloweralkyl, and alkyl-NX$_1$X$_2$, each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6;

k is an integer from 0 to 2;

R2 is -T-(CH$_2$)$_m$-Q$_1$-(CH$_2$)$_n$-Z;

each of m and n is independently an integer from 0 to 7;

T is selected from the group consisting of an aromatic ring having 5 to 8 carbon atoms as ring members, a heteroaromatic ring having 5 to 8 ring members;

Q$_1$ is selected from the group consisting of NH, O, S, CH=CH, C≡C, CO, SO$_2$ and OSO$_2$; and Z is selected from the group consisting of an unsaturated ring having 5 ring atoms and 0 to 2 independently selected heteroatoms as ring members fused to an unsaturated ring having 5 ring atoms and 0 to 2 independently selected heteroatoms as ring members, an unsaturated ring having 5 ring atoms and 0 to 2 independently selected heteroatoms as ring members fused to an unsaturated ring having 6 or 7 ring atoms and 0 to 4 independently selected heteroatoms as ring members or an unsaturated ring having 6 ring atoms and 0 to 3 independently selected heteroatoms as ring members fused to an unsaturated ring having 6 or 7 ring atoms and 0 to 4 independently selected heteroatoms as ring members; or R2 is -T-$(CH_2)_m$-$Q_1$-$(CH_2)_n$-Z;

T is selected from the group consisting of an aromatic ring having 5 to 8 carbon atoms as ring members, a heteroaromatic ring having 5 to 8 ring members;

each of m and n is independently an integer from 0 to 7;

$Q_1$ is selected from the group consisting of NH, O, S, CH=CH, C≡C, CO, $SO_2$ and $OSO_2$;

Z is

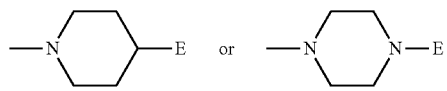

wherein E is selected from the group consisting of a C1 to C4, linear or branched alkyl group, a phenyl group, a substituted phenyl group, a benzyl group and a substituted benzyl group; or R2 is -T-$(CH_2)_m$-$Q_1$-$(CH_2)_n$-Z;

T is selected from the group consisting of an aromatic ring having 5 to 8 carbon atoms as ring members, a heteroaromatic ring having 5 to 8 ring members;

each of m and n is independently an integer from 0 to 7;

$Q_1$ is selected from the group consisting of NH, O, S, CH=CH, C≡C, CO, $SO_2$ and $OSO_2$;

Z is selected from the group consisting of

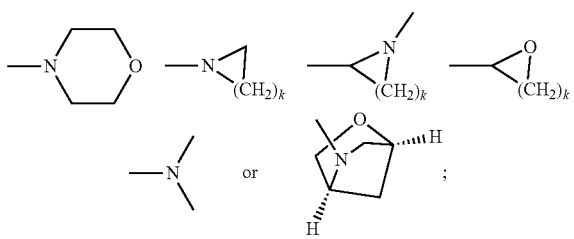

wherein k is an integer from 1 to 5; and each of $A_1$ and $A_2$ is independently selected from a C1 to C4 alkyl group, a phenyl group and a substituted phenyl group.

3. The method of claim 1, wherein

R1 is -T-$(CH_2)_n$-Z;

n is an integer from 0 to 7;

T is selected from the group consisting of an aromatic ring having 5 to 8 carbon atoms as ring members and a heteroaromatic ring having 5 to 8 ring members;

Z is $COOX_3$; and $X_3$ is alkyl;

or

R1 is -T-$(CH_2)_n$-Z;

n is an integer from 0 to 7;

T is selected from the group consisting of an aromatic ring having 5 to 8 carbon atoms as ring members and a heteroaromatic ring having 5 to 8 ring members;

Z is selected from the group consisting of

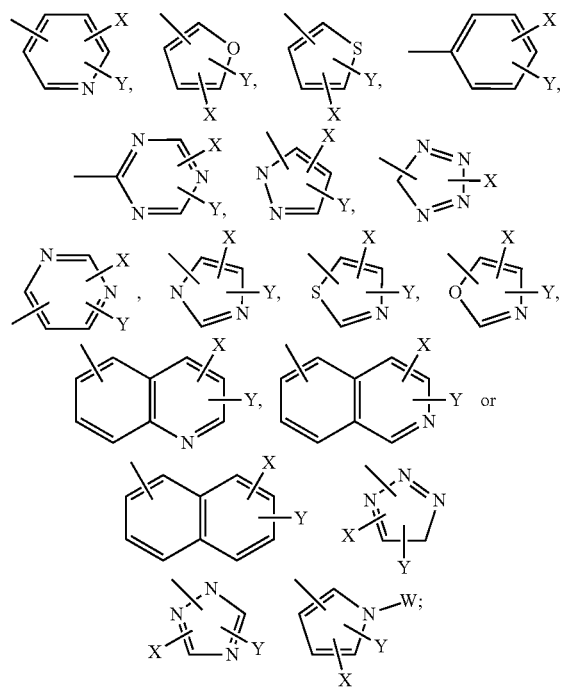

wherein X is selected from H, halogen, ester, $CF_3$, $CF_2H$, $N_3$, NCS, CN, $NO_2$, $NX_1X_2$, —C(=O)N—O-$X_1$, —C(=N—O-$X_1$)$X_2$, $OX_3$, $SX_3$, OAc, $OSO_2X_3$, O-acyl, S-acyl, $SO_2$-alkyl, SO-alkyl, $SC(CH_3)_2COOX_8$, $OC(CH_3)_2COOX_8$, $C(CH_3)_2COOX_8$, Si(alkyl)$_3$, alkyl-CN, O-aroyl, $O(CH_2)_jOX_3$, $O(CH_2)_jNX_1X_2$, NH-acyl, NH-aroyl, CHO, C(halogen)$_3$, $COOX_3$, $SO_3H$, $SO_2NX_1X_2$, $CONX_1X_2$, NHC(O)O-alkyl, $NHSO_2$-alkyl, alkoxy, alkyl, alcohol, alkylmercapto, alkylamino, di-alkylamino, alkylsulfinyl or alkylsulfonyl, $CX_4X_5X_6$, —CH=CH$X_8$ and —C≡C$X_8$; wherein Y is $COOX_3$;

$X_3$ is alkyl; and each of $X_1$ and $X_2$ is independently selected from H or alkyl, alkylamino, di-alkylamino, ammonium salt, quaternary ammonium salt, and a heterocyclic ring having 4 to 7 ring members and optionally one additional heteroatom selected from O, N and S; or $X_1$ and $X_2$ together form part of a heterocyclic ring having 4 to 7 ring members and optionally one additional heteroatom selected from O, N and S, or $X_1$ and $X_2$ together form part of an imide ring having 5 to 6 members, each of $X_4$, $X_5$, and $X_6$ is independently selected from H, alkyl, carbocyclic ring, hydroxyloweralkyl, alkyl-OH, halogen, CN, SNO, $S(SO_2)$alkyl, $NX_1X_2$, $COOX_3$, $CONX_3$, $OX_7$, and O-alkyl-$X_7$; wherein $X_7$ is selected from the group consisting of H, alkyl, $NO_2$, NO, $P(O)(OX_8)_2$, $PH(O)(OX_8)$, $S(O)_kN(alkyl)_2$, $S(O)_kX_8$, $S(O)_kOX_8$, $COOX_8$, $CONX_8$, $SO_3H$ and $COX_8$, wherein $X_8$ is selected from the group consisting of H, alkyl, carbocyclic ring, heterocyclic ring, aromatic ring, heteroaromatic ring, and -$CX_9$=$CHX_{10}$ wherein each of $X_9$ and $X_{10}$ is independently H or alkyl;

m is an integer from 0 to 7;

j is an integer from 0 to 6;

k is an integer from 0 to 2; and
R1 is -T-(CH$_2$)$_m$-Q$_1$-(CH$_2$)$_n$-Z;
each of m and n is independently an integer from 0 to 7;
T is selected from the group consisting of an aromatic ring having 5 to 8 carbon atoms as ring members and a heteroaromatic ring having 5 to 8 ring members;
Q$_1$ is selected from the group consisting of NH, O, S, CH=CH, C≡C, CO, SO$_2$ and OSO$_2$;
Z is COOX$_3$; and
X$_3$ is alkyl;
or
R1 is -T-(CH$_2$)$_m$-Q$_1$-(CH$_2$)$_n$-Z;
each of m and n is independently an integer from 0 to 7;
T is selected from the group consisting of an aromatic ring having 5 to 8 carbon atoms as ring members and a heteroaromatic ring having 5 to 8 ring members;
Q$_1$ is selected from the group consisting of NH, O, S, CH=CH, C≡C, CO, SO$_2$ and OSO$_2$;
Z is selected from the group consisting of

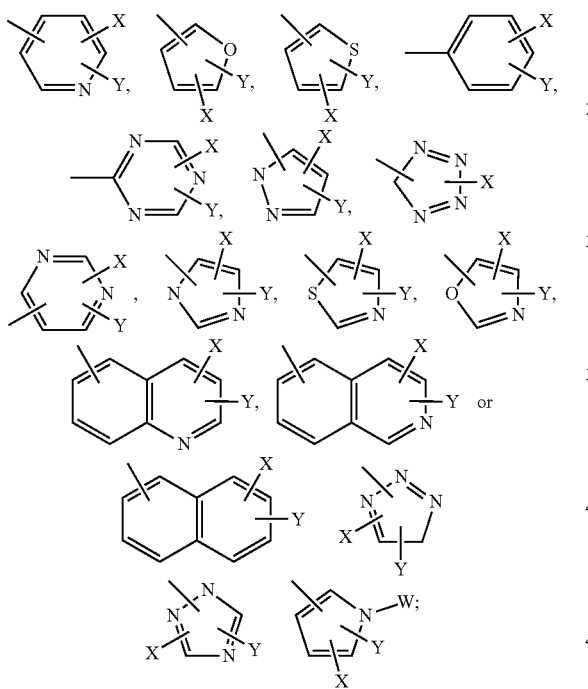

wherein X is selected from H, halogen, ester, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$; wherein
Y is COOX$_3$;
X$_3$ is alkyl; and
each of X$_1$ and X$_2$ is independently selected from H or alkyl, alkylamino, di-alkylamino, ammonium salt, quaternary ammonium salt, or a heterocyclic ring having 4 to 7 ring members and optionally one additional heteroatom selected from O, N and S; or X$_1$ and X$_2$ together form part of a heterocyclic ring having 4 to 7 ring members and optionally one additional heteroatom selected from O, N and S, or
X$_1$ and X$_2$ together form part of an imide ring having 5 to 6 members,
each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein
X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein
X$_8$ is selected from the group consisting of H, alkyl, carbocyclic ring, heterocyclic ring, aromatic ring, heteroaromatic ring, and -CX$_9$=CHX$_{10}$, wherein
each of X$_9$ and X$_{10}$ is independently H or alkyl;
m is an integer from 0 to 7;
j is an integer from 0 to 6;
k is an integer from 0 to 2.
4. The method of claim 1, wherein
R3 is

G is selected from the group consisting of CH, C(CH$_3$), C(CN) and N;
each of L and J is independently selected from (CH$_2$)$_n$, (CH$_3$)$_2$, C=O, O, —CHOH, C(CH$_3$)OM$_1$, C(CH$_2$)$_n$(X)Y, NM$_1$, SO$_2$, and SO;
K is C(CH$_2$)$_n$(X)Y;
n is an integer from 0 to 7;
M$_1$ is H, alkyl or C(O)M$_2$;
M$_2$ is selected from the group consisting of H, alkyl, NM$_3$M$_4$, OM$_5$, and M$_3$, M$_4$ and M$_5$ are independently selected from H, OH or alkyl;
X is selected from H, halogen, ester, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$; wherein
Y is COOX$_3$;
X$_3$ is alkyl; and
each of X$_1$ and X$_2$ is independently selected from H or alkyl, alkylamino, di-alkylamino, ammonium salt, quaternary ammonium salt, or a heterocyclic ring having 4 to 7 ring members and optionally one additional heteroatom selected from O, N and S; or
X$_1$ and X$_2$ together form part of a heterocyclic ring having 4 to 7 ring members and optionally one additional heteroatom selected from O, N and S, or
X$_1$ and X$_2$ together form part of an imide ring having 5 to 6 members,
each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6; and k is an integer from 0 to 2; or

R3 is selected from the group consisting of

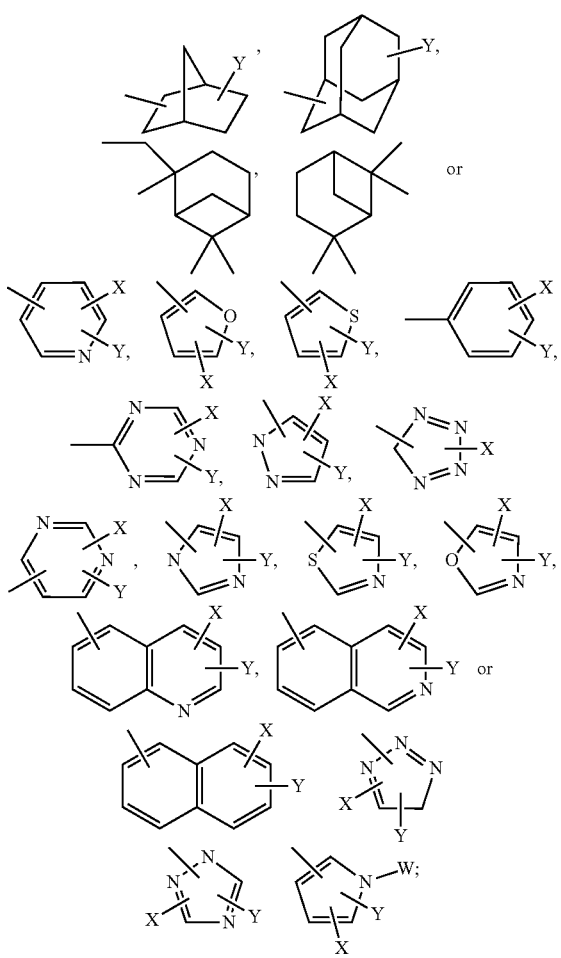

wherein X is selected from H, halogen, ester, CF$_3$, CF$_2$H, N$_3$, NCS, CN, NO$_2$, NX$_1$X$_2$, —C(=O)N—O-X$_1$, —C(=N—O-X$_1$)X$_2$, OX$_3$, SX$_3$, OAc, OSO$_2$X$_3$, O-acyl, S-acyl, SO$_2$-alkyl, SO-alkyl, SC(CH$_3$)$_2$COOX$_8$, OC(CH$_3$)$_2$COOX$_8$, C(CH$_3$)$_2$COOX$_8$, Si(alkyl)$_3$, alkyl-CN, O-aroyl, O(CH$_2$)$_j$OX$_3$, O(CH$_2$)$_j$NX$_1$X$_2$, NH-acyl, NH-aroyl, CHO, C(halogen)$_3$, COOX$_3$, SO$_3$H, SO$_2$NX$_1$X$_2$, CONX$_1$X$_2$, NHC(O)O-alkyl, NHSO$_2$-alkyl, alkoxy, alkyl, alcohol, alkylmercapto, alkylamino, di-alkylamino, alkylsulfinyl or alkylsulfonyl, CX$_4$X$_5$X$_6$, —CH=CHX$_8$ and —C≡CX$_8$; wherein Y is COOX$_3$;

X$_3$ is alkyl; and each of X$_1$ and X$_2$ is independently selected from H or alkyl, alkylamino, di-alkylamino, ammonium salt, quaternary ammonium salt, or a heterocyclic ring having 4 to 7 ring members and optionally one additional heteroatom selected from O, N and S; or X$_1$ and X$_2$ together form part of a heterocyclic ring having 4 to 7 ring members and optionally one additional heteroatom selected from O, N and S, or X$_1$ and X$_2$ together form part of an imide ring having 5 to 6 members, each of X$_4$, X$_5$, and X$_6$ is independently selected from H, alkyl, carbocyclic ring, hydroxyloweralkyl, alkyl-OH, halogen, CN, SNO, S(SO$_2$)alkyl, NX$_1$X$_2$, COOX$_3$, CONX$_3$, OX$_7$, and O-alkyl-X$_7$, wherein X$_7$ is selected from the group consisting of H, alkyl, NO$_2$, NO, P(O)(OX$_8$)$_2$, PH(O)(OX$_8$), S(O)$_K$N(alkyl)$_2$, S(O)$_k$X$_8$, S(O)$_k$OX$_8$, COOX$_8$, CONX$_8$, SO$_3$H, and COX$_8$, wherein X$_8$ is selected from the group consisting of H, alkyl, carbocyclic ring, heterocyclic ring, aromatic ring, heteroaromatic ring, and -CX$_9$=CHX$_{10}$, wherein each of X$_9$ and X$_{10}$ is independently H or alkyl;

m is an integer from 0 to 7;

j is an integer from 0 to 6; and k is an integer from 0 to 2.

5. The method of claim 1, wherein the acute cannabinoid overdose symptoms are caused by a classical cannabinoid comprising Δ$^9$-tetrahydrocannabinol (THC).

6. The method of claim 1, wherein the acute cannabinoid overdose symptoms are caused by a synthetic psychoactive cannabinoid selected from the group consisting of aminoalkylindoles, cyclohexylphenols, naphtholylindoles, tetramethylcyclopropyls, indole carboxamides, and indozole carboxamides.

7. The method of claim 1, wherein the acute cannabinoid overdose symptoms are caused by *cannabis*.

8. The method of claim 1, wherein the acute cannabinoid overdose symptoms are caused by herbal or synthetic Δ$_9$-tetrahydrocannabinol (THC).

9. The method of claim 1, wherein the acute cannabinoid overdose symptoms are caused by one or both of classical cannabinoids and synthetic psychoactive cannabinoids.

10. The method of claim 1, wherein administering the compound, pharmaceutically acceptable salt, solvate, hydrate, enantiomer, diastereomer, geometric isomer, racemate, tautomer, rotamer, atropisomer, isotopic variation, N-oxide, or polymorph thereof induces reduced or no antagonist-elicited withdrawal symptoms in the individual.

11. The method of claim 1, wherein administering the compound, pharmaceutically acceptable salt, solvate, hydrate, enantiomer, diastereomer, geometric isomer, racemate, tautomer, rotamer, atropisomer, isotopic variation, N-oxides, or polymorph thereof induces reduced or no scratching symptoms in the individual.

\* \* \* \* \*

UNITED STATES PATENT AND TRADEMARK OFFICE
CERTIFICATE OF CORRECTION

PATENT NO. : 12,054,480 B2
APPLICATION NO. : 17/392191
DATED : August 6, 2024
INVENTOR(S) : Alexandros Makriyannis and Kiran Vemuri It is certified that error appears in the above-identified patent and that said Letters Patent is hereby corrected as shown below:

In the Claims

Claim 1, Column 102, Line 32:
Before "-T-$(CH_2)_n$-Z" insert --R1 is--

Claim 1, Column 103, Line 2:
Before "-C(=O)N-O-$X_1$" insert --ester,--

Claim 1, Column 103, Line 3:
After "$C(CH_3)_2COOX_8$" insert --,$COOX_3$--

Claim 1, Column 103, Line 29:
After "the group consisting of" insert --ester,--

Claim 1, Column 104, Line 23:
After "$C(CH_3)_2COOX_8$" insert --, $COOX_3$--

Claim 1, Column 107, Line 40:
Delete "$OC(CH_3)_2COOX_8C(CH_3)_2COOX_8$" and insert --$OC(CH_3)_2COOX_8, C(CH_3)_2COOX_8$--

Claim 1, Column 110, Line 61:
Delete "C C" and insert --C≡C--

Claim 1, Column 112, Line 1:
Delete "$OC(CH_3)_2COOX_8C(CH_3)_2COOX_8$" and insert --$OC(CH_3)_2COOX_8, C(CH_3)_2COOX_8$--

Claim 1, Column 115, Line 10:
Delete "$OC(CH_3)_2COOX_8C(CH_3)_2COOX_8$" and insert --$OC(CH_3)_2COOX_8, C(CH_3)_2COOX_8$--

Signed and Sealed this
Eighth Day of April, 2025

Coke Morgan Stewart
*Acting Director of the United States Patent and Trademark Office*

CERTIFICATE OF CORRECTION (continued)
U.S. Pat. No. 12,054,480 B2

Claim 1, Column 120, Lines 15-20:

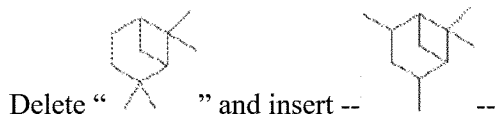

Delete " " and insert -- --

Claim 1, Column 121, Line 19:
After "k is an integer from 0 to 2;" insert --or--

Claim 1, Column 122, Line 59:
Delete "$O(CH_2)NX_1X_2$" and insert --$O(CH_2)_jNX_1X_2$--

Claim 1, Column 125, Line 44:
After "is independently selected from" insert --H, halogen,--

Claim 2, Column 127, Line 47:
Delete "or"

Claim 2, Column 130, Line 4:
Delete "and" and insert --or--

Claim 2, Column 130, Line 27:
After "as ring members" insert --,--

Claim 2, Column 132, Line 55:
After "from 0 to 2;" insert --or--